United States Patent
Solovyev et al.

(10) Patent No.: US 11,840,567 B2
(45) Date of Patent: Dec. 12, 2023

(54) BISPECIFIC ANTIBODIES WITH SPECIFIC BINDING TO CD47 AND PD-L1

(71) Applicant: JOINT STOCK COMPANY "BIOCAD", St.Petersburg (RU)

(72) Inventors: Kirill Vladimirovich Solovyev, St.Petersburg (RU); Andrei Borisovich Ulitin, Puschino (RU); Timofey Aleksandrovich Nemankin, St. Petersburg (RU); Valery Vladimirovich Solovyev, Pushchino (RU); Dmitry Valentinovich Morozov, Saint Petersburg (RU)

(*) Notice: Subject to any disclaimer, the term of this patent is extended or adjusted under 35 U.S.C. 154(b) by 245 days.

(21) Appl. No.: 16/753,587

(22) PCT Filed: Oct. 3, 2018

(86) PCT No.: PCT/EA2018/050001
§ 371 (c)(1),
(2) Date: Apr. 3, 2020

(87) PCT Pub. No.: WO2019/068302
PCT Pub. Date: Apr. 11, 2019

(65) Prior Publication Data
US 2020/0270345 A1    Aug. 27, 2020

(30) Foreign Application Priority Data
Oct. 3, 2017 (EA) .................................. 201791961

(51) Int. Cl.
*C07K 16/28* (2006.01)

(52) U.S. Cl.
CPC ...... *C07K 16/2803* (2013.01); *C07K 16/2827* (2013.01); *C07K 2317/31* (2013.01); *C07K 2317/55* (2013.01); *C07K 2317/565* (2013.01); *C07K 2317/622* (2013.01); *C07K 2317/732* (2013.01); *C07K 2317/734* (2013.01); *C07K 2317/76* (2013.01); *C07K 2317/92* (2013.01)

(58) Field of Classification Search
CPC ............ C07K 16/2827; C07K 2317/31; C07K 2317/565
USPC ........................................... 424/133.1, 135.1
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,634,665 A | 1/1987 | Axel et al. |
| 4,676,980 A | 6/1987 | Segal et al. |
| 4,740,461 A | 4/1988 | Kaufman |
| 4,816,567 A | 3/1989 | Cabilly et al. |
| 4,912,040 A | 3/1990 | Kaufman et al. |
| 4,959,455 A | 9/1990 | Clark et al. |
| 4,968,615 A | 11/1990 | Koszinowski et al. |
| 5,168,062 A | 12/1992 | Stinski |
| 5,179,017 A | 1/1993 | Axel et al. |
| 5,229,275 A | 7/1993 | Goroff |
| 5,500,362 A | 3/1996 | Robinson et al. |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,571,894 A | 11/1996 | Wells et al. |
| 5,587,458 A | 12/1996 | King et al. |
| 5,591,669 A | 1/1997 | Krimpenfort et al. |
| 5,641,870 A | 6/1997 | Rinderknecht et al. |
| 5,731,168 A | 3/1998 | Carter et al. |
| 5,821,337 A | 10/1998 | Carter et al. |
| 6,517,529 B1 | 2/2003 | Quinn |
| 11,236,167 B2 * | 2/2022 | Ulitin ............... A61K 39/39558 |
| 2013/0142786 A1 | 6/2013 | Liu et al. |
| 2016/0108128 A1 | 4/2016 | Banham et al. |
| 2020/0369771 A1 * | 11/2020 | Ulitin ................. C07K 16/2827 |

FOREIGN PATENT DOCUMENTS

| | | |
|---|---|---|
| EP | 0256055 B1 | 8/1991 |
| EP | 0323997 B1 | 4/1993 |
| EP | 0338841 B1 | 3/1995 |
| JP | 2015-536351 A | 12/2015 |
| WO | 91/00360 A1 | 1/1991 |
| WO | 92/00373 A1 | 1/1992 |
| WO | 93/08829 A1 | 5/1993 |
| WO | 93/16185 A2 | 8/1993 |
| WO | 94/04690 A1 | 3/1994 |
| WO | 0216846 B2 | 4/1995 |
| WO | 97/17852 A1 | 5/1997 |
| WO | 99/40940 A1 | 8/1999 |
| WO | 01/14557 A1 | 3/2001 |

(Continued)

OTHER PUBLICATIONS

Kim et al.(Biochimica et Biophysica Acta 1844 (2014) 1983-2001).*
Henry et al. (Frontiers in Immunology 8:1-15 (Dec. 12, 2017).*
Yu et al., Engagement of CD47 Inhibits the Contact Hypersensitivity Response Via the Suppression of Motility and B7 Expression by Langerhans Cells. Journal of Investigative Dermatology. vol. 126, Issue 4, Apr. 2006, pp. 797-807.
Ward et al., Binding activities of a repertoire of single immunoglobulin variable domains secreted from *Escherichia coli*. (1989) Nature 341:544-546.
Bird et al. Single-Chain Antigen-Binding Proteins. (1988) Science 242:423-426.

(Continued)

*Primary Examiner* — Lynn A Bristol

(57) ABSTRACT

The present invention relates to the field of bioengineering, specifically to antibodies or their antigen-binding fragments, and to the use thereof. More particularly, the present invention relates to antibodies that bind specifically to CD47 and PD-L1. The invention also relates to a nucleic acid that codes for the given antibody or for the antigen-binding fragment thereof, to an expression vector, to a method of producing the antibody, and to a use of the aforementioned antibodies and compositions in cancer treatment.

13 Claims, 9 Drawing Sheets

Specification includes a Sequence Listing.

(56) References Cited

FOREIGN PATENT DOCUMENTS

| | | | |
|---|---|---|---|
| WO | 02/086083 | A2 | 10/2002 |
| WO | 2007/005874 | A2 | 1/2007 |
| WO | 2010/036959 | A2 | 4/2010 |
| WO | 2010/077634 | A1 | 7/2010 |
| WO | 2011/066389 | A1 | 6/2011 |
| WO | 2011/143624 | A2 | 11/2011 |
| WO | 2013/119714 | A1 | 8/2013 |
| WO | 2014/087248 | A2 | 6/2014 |
| WO | 2014/093678 | A2 | 6/2014 |
| WO | 2014/123580 | A1 | 8/2014 |
| WO | 2015/191861 | A1 | 12/2015 |
| WO | 2016/023001 | A1 | 2/2016 |
| WO | 2017/053423 | A1 | 3/2017 |

OTHER PUBLICATIONS

Huston et al. Protein engineering of antibody binding sites: recovery of specific activity in an anti-digoxin single-chain Fv analogue produced in *Escherichia coli*. (1988) Proc. Natl. Acad. Sci. USA 85:5879-5883.

Burks et al., In vitro scanning saturation mutagenesis of an antibody binding pocket. Proc Natl Acad Sci USA, 94:412-417 (1997).

Wu et al., Stepwise in vitro affinity maturation of Vitaxin, an αvβ3-specific humanized mAb. Proc Natl Acad Sci USA 95:6037 6042 (1998).

Magdelaine-Beuzelin et al., Structure-function relationships of the variable domains of monoclonal antibodies approved for cancer treatment. Critical Reviews in Oncology/Hematology. vol. 64, Issue 3, Dec. 2007, pp. 210-225.

Lefranc et al., IMGT unique numbering for immunoglobulin and T cell receptor variable domains and Ig superfamily V-like domains. Developmental & Comparative Immunology. vol. 27, Issue 1, Jan. 2003, pp. 55-77.

Smith GP, Filamentous fusion phage: novel expression vectors that display cloned antigens on the virion surface. Science 1985, 228:1315-1317.

Lonberg N, et al.: Antigen-specific human antibodies from mice comprising four distinct genetic modifications. Nature 1994, 368:856-859.

Ravetch and Kinet, Fc Receptors. Annual Review of Immunology. vol. 9:457-492 (Volume publication date Apr. 1991).

Clynes et al. Fc receptors are required in passive and active immunity to melanoma. PNAS (USA) 95: 652-656 (1998).

Daeron, Annu. Fc Receptor Biology. Annual Review of Immunology. vol. 15:203-234 (Volume publication date Apr. 1997).

Gazzano-Santoro et al., A non-radioactive complement-dependent cytotoxicity assay for anti-CD20 monoclonal antibody. Journal of Immunological Methods vol. 202, Issue 2, Mar. 28, 1997, pp. 163-171.

Kohler, et al. Continuous cultures of fused cells secreting antibody of predefined specificity. Nature 256, 1975, p. 495-497.

McCafferty et al., Phage antibodies: filamentous phage displaying antibody variable domains. Nature, 348:552-554 (1990).

Clackson et al., Making antibody fragments using phage display libraries. Nature, 352:624-628 (1991).

Marks et al., By-passing immunization: Human antibodies from V-gene libraries displayed on phage. J. Mol. Biol., 222:581-597 (1991).

Marks et al., By-passing immunization: Building High Affinity Human Antibodies by Chain Shuffling. Bio/Technology, 10:779-783 (1992).

Waterhouse et al., Combinatorial infection and in vivo recombination: a strategy for making large phage antibody repertoires. Nucl. Acids. Res. 21:2265-2266 (1993).

Morrison, et al., Chimeric human antibody molecules: mouse antigen-binding domains with human constant region domains. Proc. Natl. Acad. Sci. USA: 81:6851 (1984).

Jones et al., Replacing the complementarity-determining regions in a human antibody with those from a mouse. Nature, 321:522-525 (1986).

Carter et al., Humanization of an anti-p185HER2 antibody for human cancer therapy. Proc. Natl. Acad. Sci. USA: 89:4285 (1992).

Carter et al., High Level *Escherichia coli* Expression and Production of a Bivalent Humanized Antibody Fragment. Bio/Technology 10:163-167 (1992).

Buresh et al., [17] Bispecific monoclonal antibodies from hybrid hybridomas. Methods in Enzymology 121:210 (1986).

Brennan et al., Preparation of Bispecific Antibodies by Chemical Recombination of Monoclonal Immunoglobulin G1 Fragments. Science 229:81 (1985).

Shalaby et al., Development of humanized bispecific antibodies reactive with cytotoxic lymphocytes and tumor cells overexpressing the HER2 protooncogene. J. Exp. Med. 175:217-225 (1992).

Kostelny et al, Formation of a bispecific antibody by the use of leucine zippers. J. Immunol. 148(5):1547-1553 (1992).

Hollinger et al., "Diabodies": Small bivalent and bispecific antibody fragments. Proc. Natl. Acad. Sci. USA 90:6444-6448 (1993).

Hans et al. A Large Non-immunized Human Fab Fragment Phage Library That Permits Rapid Isolation and Kinetic Analysis of High Affinity Antibodies. J Biol Chem. Jun. 25, 1999; 274(26): 18218-30.

Sachdev S.Sidhu et al., [21] Phage display for selection of novel binding peptides. Methods in Enzymology. vol. 328, 2000, pp. 333-363, IN5.

Friedrich Koch-Nolte et al., Single domain antibodies from llama effectively and specifically block T cell ecto-ADP-ribosyltransferase ART2.2 in vivo. FASEB J. Nov. 2007; 21 (13): 3490-3498.

IA.D. Griffiths et al., solation of high affinity human antibodies directly from large synthetic repertoires. EMBO J. Jul. 15, 1994;13(14):3245-60.

Tristan J. Vaughan et al., Human Antibodies with Sub-nanomolar Affinities Isolated from a Large Non-immunized Phage Display Library. Nat Biotechnol. Mar. 1996;14(3):309-314.

Kozbor, A human hybrid myeloma for production of human monoclonal antibodies. J Immunol Dec. 1, 1984, 133(6) 3001-3005 (Abstract).

Sims et al., A humanized CD18 antibody can block function without cell destruction. J. Immunol. 151:2296 (1993) (Abstract).

Gruber et al., Efficient tumor cell lysis mediated by a bispecific single chain antibody expressed in *Escherichia coli*. J. Immunol., 152:5368-5374 (1994) (Abstract).

International application No. PCT/EA2018/050001 International Search Report dated Feb. 28, 2019.

International application No. PCT/EA2018/050001 Translation of the ISR dated Feb. 28, 2019.

International application No. PCT/EA2018/050001 Written Opinion of the International Searching Authority dated Feb. 28, 2019.

International application No. PCT/EA2018/050001 English Translation of the Written Opinion of the International Searching Authority dated Feb. 28, 2019.

Corresponding European patent application No. 18864490.0 extended European search report dated Oct. 6, 2021.

Corresponding Japanese patent application No. 2020-519341 Notice of reason for refusal dated Jul. 11, 2022 (Translations provided).

Corresponding Japanese patent application No. 2020-519341 Decision of refusal dated Mar. 3, 2023 (Translations provided).

Liu, Boning. "Construction and Anti-tumor Effects of a Novel Bispecific Fusion Protein Targeting PD-L1 and CD47", Doctoral Dissertation, South China University of Technology, CN, (Dec. 27, 2016), pp. 1-121. (Abstract provided).

Jonathan T. Sockolosky et al., "Durable antitumor responses to CD47 blockade require adaptive immune stimulation", Proceedings of the National Academy of Sciences, US, (May 10, 2016), vol. 113, No. 19, doi:10.1073/pnas.1604268113, ISSN 0027-8424, pp. E2646-E2654.

\* cited by examiner

1. Bio-Rad Protein Standard marker
2. anti-CD47 10 µg
3. anti-CD47 40 µg

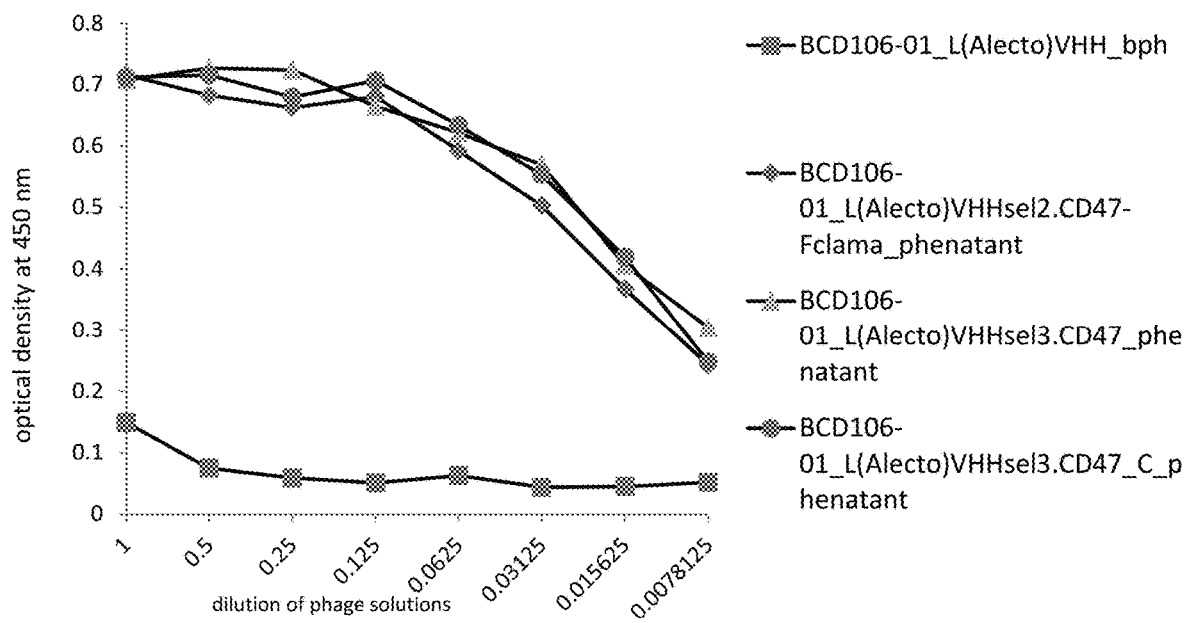
Fig.5
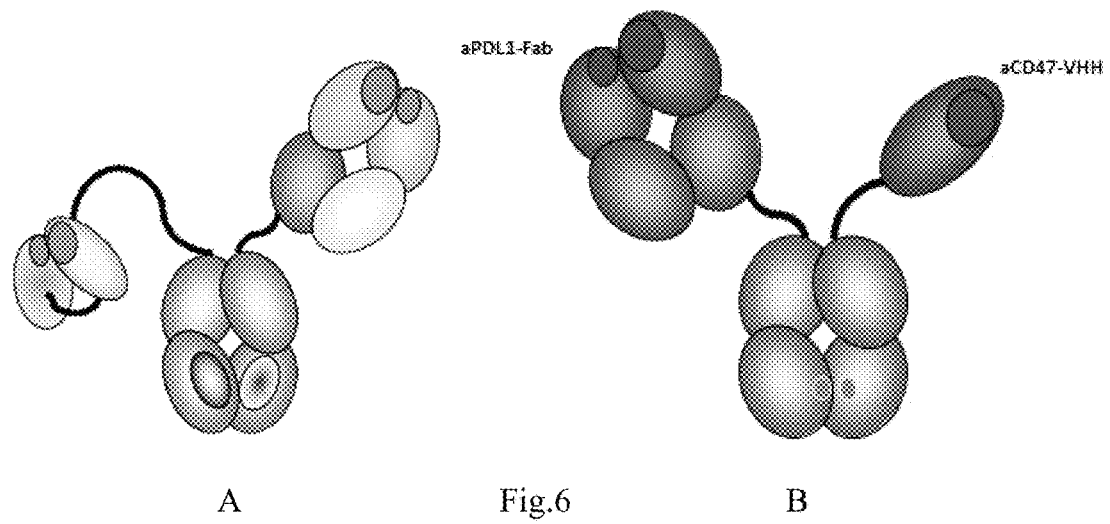
A          Fig.6          B

SEQUENCE LISTING

<160> NUMBER OF SEQ ID NOS: 120

<210> SEQ ID NO 1
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 1

Arg Tyr Trp Met Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 2

Ile Asn Ala Met Asn
1               5

<210> SEQ ID NO 3
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 3

Lys Tyr Trp Met Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 4

Ser Ile Phe Ser Ile Asn Ala Met Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 5

Asp Tyr Ala Met Ser
1               5

<210> SEQ ID NO 6
<211> LENGTH: 23
<212> TYPE: PRT
<213> ORGANISM: Artificial Sequence
<220> FEATURE:
<223> OTHER INFORMATION: Synthesized Sequence

<400> SEQUENCE: 6

Ile Glu Asp Ser Ser Ile Asn Thr Gly Gly Gly Thr Glu Thr Thr Tyr
1               5                   10                  15

Tyr Thr Asp Ser Val Lys Gly
            20

<210> SEQ ID NO 7
<211> LENGTH: 24
<212> TYPE: PRT
<213> ORGANISM: Artificial Sequence
<220> FEATURE:
<223> OTHER INFORMATION: Synthesized Sequence

<400> SEQUENCE: 7

Ser Ile Glu Asp Ser Ser Ile Asn Thr Gly Gly Gly Thr Glu Thr Thr
1               5                   10                  15

Tyr Tyr Thr Asp Ser Val Lys Gly
            20

<210> SEQ ID NO 8
<211> LENGTH: 24
<212> TYPE: PRT
<213> ORGANISM: Artificial Sequence
<220> FEATURE:
<223> OTHER INFORMATION: Synthesized Sequence

<400> SEQUENCE: 8

Asn Ile Lys Gln Asp Gly Ile Asn Thr Gly Gly Gly Thr Ser Glu Lys
1               5                   10                  15

Tyr Tyr Val Asp Ser Val Lys Gly
            20

<210> SEQ ID NO 9
<211> LENGTH: 17
<212> TYPE: PRT
<213> ORGANISM: Artificial Sequence
<220> FEATURE:
<223> OTHER INFORMATION: Synthesized Sequence

<400> SEQUENCE: 9

Ser Ile Glu Asp Ser Ser Glu Thr Thr Tyr Tyr Thr Asp Ser Val Lys
1               5                   10                  15

Gly

<210> SEQ ID NO 10
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 10

Gln Ile Thr Asp Glu Gly Ile Thr Asn Tyr Val Asp Ser Val Lys Gly
1               5                   10                  15

<210> SEQ ID NO 11
<211> LENGTH: 18
<212> TYPE: PRT
<213> ORGANISM: Artificial Sequence
<220> FEATURE:
<223> OTHER INFORMATION: Synthesized Sequence

<400> SEQUENCE: 11

Ser Ile Glu Asp Ser Ser Thr Glu Thr Thr Tyr Tyr Thr Asp Ser Val
1               5                   10                  15

Lys Gly

<210> SEQ ID NO 12
<211> LENGTH: 19
<212> TYPE: PRT
<213> ORGANISM: Artificial Sequence
<220> FEATURE:
<223> OTHER INFORMATION: Synthesized Sequence

<400> SEQUENCE: 12

Ser Ile Glu Asp Ser Ser Ile Thr Glu Thr Thr Tyr Tyr Thr Asp Ser
1               5                   10                  15

Val Lys Gly

<210> SEQ ID NO 13
<211> LENGTH: 18
<212> TYPE: PRT
<213> ORGANISM: Artificial Sequence
<220> FEATURE:
<223> OTHER INFORMATION: Synthesized Sequence

<400> SEQUENCE: 13

Ser Ile Asn Asp Gly Gly Gly Asp Asp Ser Thr Tyr Tyr Ala Asp Ser
1               5                   10                  15

Val Lys

<210> SEQ ID NO 14
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 14

Gly Ile Arg Thr Ser Gly Asp Thr Asp Tyr Ala Asp Ser Val Lys Gly
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 15

Gln Ile Thr Asp Glu Gly Ile Thr Asn Tyr Val Asp Ser Val Lys Gly
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: Synthesized Sequence

<400> SEQUENCE: 16

Asp Ile Ser Trp Ser Gly Ser Asn Thr Asn Tyr Ala Asp Ser Val Lys
1               5                   10                  15

Gly

<210> SEQ ID NO 17
<211> LENGTH: 18
<212> TYPE: PRT
<213> ORGANISM: Artificial Sequence
<220> FEATURE:
<223> OTHER INFORMATION: Synthesized Sequence

```
<400> SEQUENCE: 17

Gly Asp Tyr Tyr Cys Thr Thr Tyr Glu Cys Gln His Tyr Tyr Gly Met
1               5                   10                  15

Asp Tyr

<210> SEQ ID NO 18
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 18

Val Ile Thr Thr Thr Ser Glu Ile Tyr
1               5

<210> SEQ ID NO 19
<211> LENGTH: 18
<212> TYPE: PRT
<213> ORGANISM: Artificial Sequence
<220> FEATURE:
<223> OTHER INFORMATION: Synthesized Sequence

<400> SEQUENCE: 19

Gly Asp Tyr Tyr Cys Thr His Tyr Glu Cys Gln His Tyr Tyr Gly Met
1               5                   10                  15

Asp Tyr

<210> SEQ ID NO 20
<211> LENGTH: 12
<212> TYPE: PRT
<213> ORGANISM: Artificial Sequence
<220> FEATURE:
<223> OTHER INFORMATION: Synthesized Sequence

<400> SEQUENCE: 20

Asn Ala Phe Val Ile Thr Thr Thr Ser Glu Ile Tyr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthesized Sequence

<400> SEQUENCE: 21

Ala Pro Leu Leu Leu Ala Met Thr Phe Gly Val Gly Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 22

Arg Ala Ser Gln Ala Ile Ser Ser Tyr Leu Ala
1               5                   10

<210> SEQ ID NO 23
<211> LENGTH: 11
<212> TYPE: PRT
<213> ORGANISM: Artificial Sequence
```

-continued

<220> FEATURE:
<223> OTHER INFORMATION: Synthesized Sequence

<400> SEQUENCE: 23

Arg Ala Ser Gln Gly Ile Ser Ser Trp Leu Ala
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 24

Arg Ala Ser Gln Ser Ile Ser Ser Tyr Leu Asn
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 25

Arg Ala Ser Gln Asp Ile Gly Ser Trp Leu Ala
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 26

Arg Ala Ser Gln Ser Ile Ser Arg Asn Leu Asn
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 27

Arg Ala Ser Gln His Ile Ser Ser Trp Leu Ala
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 28

Arg Ala Ser Gln Ser Ile Ser His Tyr Leu Asn
1               5                   10

<210> SEQ ID NO 29
<211> LENGTH: 11
<212> TYPE: PRT
<213> ORGANISM: Artificial Sequence
<220> FEATURE:

```
<223> OTHER INFORMATION: Synthesized Sequence

<400> SEQUENCE: 29

Arg Ala Ser Gln Ser Val Ser Ser Tyr Leu Ala
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthesized Sequence

<400> SEQUENCE: 30

Arg Ala Ser Gln Ser Val Ser Ser Asn Tyr Leu Ala
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthesized Sequence

<400> SEQUENCE: 31

Ser Gly Ser Ser Ser Asn Ile Gly Asn Asn Tyr Val Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 32

Gln Gly Asp Arg Ile Glu Asn Tyr Tyr Thr Ser
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthesized Sequence

<400> SEQUENCE: 33

Thr Gly Ser Ser Ser Asn Ile Gly Asp Asn Tyr Val Asn
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 34

Thr Ser Ser Gln Ser Leu Val Tyr Arg Asp Gly Asn Thr Tyr Leu Asn
1               5                   10                  15

<210> SEQ ID NO 35
<211> LENGTH: 14
<212> TYPE: PRT
<213> ORGANISM: Artificial Sequence
<220> FEATURE:
<223> OTHER INFORMATION: Synthesized Sequence
```

```
<400> SEQUENCE: 35

Gly Leu Ser Ser Gly Thr Val Thr Ala Ile Asn Tyr Pro Gly
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 36

Ala Ala Ser Asn Leu Gln Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 37

Ala Ala Ser Ser Leu Gln Ser
1               5

<210> SEQ ID NO 38
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 38

Ala Ala Ser Thr Leu Gln Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 39

Thr Ala Ser Thr Leu Gln Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 40

Ala Ala Thr Arg Leu Gln Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Synthesized Sequence
```

```
<400> SEQUENCE: 41

Asp Thr Ser Asn Arg Ala Thr
1               5

<210> SEQ ID NO 42
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 42

Gly Thr Ser Ser Arg Ala Thr
1               5

<210> SEQ ID NO 43
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 43

Ala Ser Ser Thr Leu Gln Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 44

Asp Asn Tyr Arg Arg Pro Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 45

Gly Asn Ala Asn Arg Pro Ser
1               5

<210> SEQ ID NO 46
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 46

Ser Asn Ser Asn Arg Ala Ser
1               5

<210> SEQ ID NO 47
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 47
```

```
Lys Val Ser Asp Arg Asp Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 48

Gly Ala Ser Ser Arg Ala Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 49

Asn Thr Asn Thr Arg His Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 50

Gln Gln Ala Ala Ser Val Pro Leu Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 51

Gln Gln Ser Tyr Ser Thr Pro Phe Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 52

Gln Gln Ser Tyr Ser Thr Pro Trp Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 53
```

```
Gln Gln Ser His Ser Leu Pro Leu Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 54

Gln Gln Ser Tyr Arg Thr Pro Phe Thr
1               5

<210> SEQ ID NO 55
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 55

Gln Gln Ala Thr Ser Phe Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 56

Gln Gln Ser Tyr Ser Ala Leu Phe Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 57

Gln Gln Arg Ser Asn Trp Pro Pro Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 58

Gln Gln Ser Asp Thr Ser Pro Arg Val
1               5

<210> SEQ ID NO 59
<211> LENGTH: 10
<212> TYPE: PRT
<213> ORGANISM: Artificial Sequence
<220> FEATURE:
<223> OTHER INFORMATION: Synthesized Sequence

<400> SEQUENCE: 59

Gln Gln Ser Leu Ser Ile Pro Gln Val Thr
```

```
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 60

Gly Thr Trp Asp Ser Ser Leu Ser Ala Val Val
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 61

Gln Ser Gly Ser Ser Thr Glu Asn Ile
1               5

<210> SEQ ID NO 62
<211> LENGTH: 10
<212> TYPE: PRT
<213> ORGANISM: Artificial Sequence
<220> FEATURE:
<223> OTHER INFORMATION: Synthesized Sequence

<400> SEQUENCE: 62

Gln Ser Tyr Glu Ile Ser Gly Tyr Pro Val
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 63

Met Gln Gly Thr His Trp Pro Ser Thr
1               5

<210> SEQ ID NO 64
<211> LENGTH: 10
<212> TYPE: PRT
<213> ORGANISM: Artificial Sequence
<220> FEATURE:
<223> OTHER INFORMATION: Synthesized Sequence

<400> SEQUENCE: 64

Gln Gln Tyr Gly Ser Ser Pro Gln Leu Thr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthesized Sequence

<400> SEQUENCE: 65

Ala Leu Tyr Met Gly Asn Gly Gly His Met
1               5                   10
```

<210> SEQ ID NO 66
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 66

Glu Val Gln Leu Val Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
        35                  40                  45

Ser Ser Ile Glu Asp Ser Ser Ile Asn Thr Gly Gly Thr Glu Thr
    50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
        115                 120                 125

Met Val Thr Val Ser Ser
    130

<210> SEQ ID NO 67
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 67

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Tyr Trp Val Arg Gln Ala Pro Gly Lys Gly Leu Glu Trp Val
        35                  40                  45

Ser Ser Ile Glu Asp Ser Ser Ile Asn Thr Gly Gly Thr Glu Thr
    50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Arg Ala Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Gln Gly Thr
        115                 120                 125

Thr Val Thr Val Ser Ser
    130

<210> SEQ ID NO 68
<211> LENGTH: 134
<212> TYPE: PRT

<213> ORGANISM: Artificial Sequence
<220> FEATURE:
<223> OTHER INFORMATION: Synthesized Sequence

<400> SEQUENCE: 68

Glu Val Gln Leu Val Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
        35                  40                  45

Ser Ser Ile Glu Asp Ser Ser Ile Asn Thr Gly Gly Gly Thr Glu Thr
    50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
        115                 120                 125

Thr Val Thr Val Ser Ser
    130

<210> SEQ ID NO 69
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 69

Glu Val Gln Leu Val Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
        35                  40                  45

Ser Ser Ile Glu Asp Ser Ser Ile Asn Thr Gly Gly Gly Thr Glu Thr
    50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
        115                 120                 125

Thr Val Thr Val Ser Ser
    130

<210> SEQ ID NO 70
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 70

Gln Val Gln Leu Val Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
            35                  40                  45

Ser Ser Ile Glu Asp Ser Ser Ile Asn Thr Gly Gly Thr Glu Thr
50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
            115                 120                 125

Leu Val Thr Val Ser Ser
    130

<210> SEQ ID NO 71
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 71

Gln Val Gln Leu Val Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
            35                  40                  45

Ser Ser Ile Glu Asp Ser Ser Ile Asn Thr Gly Gly Thr Glu Thr
50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
            115                 120                 125

Leu Val Thr Val Ser Ser
    130

<210> SEQ ID NO 72
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 72

Glu Val Gln Leu Val Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr

```
                    20                  25                  30

Trp Met Tyr Trp Val Arg Gln Ala Pro Gly Lys Gly Leu Glu Trp Val
            35                  40                  45

Ser Ser Ile Glu Asp Ser Ser Ile Asn Thr Gly Gly Gly Thr Glu Thr
    50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
            115                 120                 125

Leu Val Thr Val Ser Ser
        130

<210> SEQ ID NO 73
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 73

Glu Val Gln Leu Val Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
            35                  40                  45

Ser Ser Ile Glu Asp Ser Ser Ile Asn Thr Gly Gly Gly Thr Glu Thr
    50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
            115                 120                 125

Leu Val Thr Val Ser Ser
        130

<210> SEQ ID NO 74
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 74

Glu Val Gln Leu Val Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
            35                  40                  45
```

Ser Ser Ile Glu Asp Ser Ser Ile Asn Thr Gly Gly Gly Thr Glu Thr
            50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
                100                 105                 110

Tyr Glu Cys Gln His Tyr Tyr Gly Met Asp Tyr Trp Gly Lys Gly Thr
            115                 120                 125

Leu Val Thr Val Ser Ser
            130

<210> SEQ ID NO 75
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 75

Gln Val Gln Leu Gln Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
                20                  25                  30

Trp Met Tyr Trp Val Arg Gln Ala Pro Gly Lys Gly Leu Glu Trp Val
            35                  40                  45

Ser Ser Ile Glu Asp Ser Ser Ile Asn Thr Gly Gly Gly Thr Glu Thr
            50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
                100                 105                 110

Tyr Glu Cys Gln His Tyr Tyr Gly Met Asp Tyr Trp Gly Lys Gly Thr
            115                 120                 125

Met Val Thr Val Ser Ser
            130

<210> SEQ ID NO 76
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 76

Gln Val Gln Leu Gln Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
                20                  25                  30

Trp Met Tyr Trp Val Arg Gln Ala Pro Gly Lys Gly Leu Glu Trp Val
            35                  40                  45

Ser Ser Ile Glu Asp Ser Ser Ile Asn Thr Gly Gly Gly Thr Glu Thr
            50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
        115                 120                 125

Met Val Thr Val Ser Ser
    130

<210> SEQ ID NO 77
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 77

Gln Val Gln Leu Gln Glu Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
        35                  40                  45

Ser Ser Ile Glu Asp Ser Ser Ile Asn Thr Gly Gly Gly Thr Glu Thr
    50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
        115                 120                 125

Leu Val Thr Val Ser Ser
    130

<210> SEQ ID NO 78
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 78

Gln Val Gln Leu Gln Glu Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
        35                  40                  45

Ser Ser Ile Glu Asp Ser Ser Ile Asn Thr Gly Gly Gly Thr Glu Thr
    50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr

```
                100                 105                 110
Tyr Glu Cys Gln His Tyr Tyr Gly Met Asp Tyr Trp Gly Lys Gly Thr
            115                 120                 125

Met Val Thr Val Ser Ser
            130

<210> SEQ ID NO 79
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 79

Glu Val Gln Leu Gln Gln Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
            35                  40                  45

Ser Ser Ile Glu Asp Ser Ser Ile Asn Thr Gly Gly Gly Thr Glu Thr
        50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
            115                 120                 125

Pro Val Thr Val Ser Ser
            130

<210> SEQ ID NO 80
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 80

Gln Val Thr Leu Arg Glu Ser Gly Gly Gly Leu Val Gln Pro Gly Gly
1               5                   10                  15

Ser Leu Thr Leu Ser Cys Ala Ala Ser Gly Phe Thr Phe Arg Arg Tyr
            20                  25                  30

Trp Met Tyr Trp Val Arg Gln Ala Pro Gly Lys Gly Leu Glu Trp Val
            35                  40                  45

Ser Ser Ile Glu Asp Ser Ser Ile Asn Thr Gly Gly Gly Thr Glu Thr
        50                  55                  60

Thr Tyr Tyr Thr Asp Ser Val Lys Gly Arg Phe Thr Ile Ser Arg Asp
65                  70                  75                  80

Asn Ala Lys Asn Thr Leu Tyr Leu Gln Met Asn Ser Leu Lys Ser Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Lys Gly Thr
            115                 120                 125
```

```
Met Val Thr Val Ser Ser
    130

<210> SEQ ID NO 81
<211> LENGTH: 134
<212> TYPE: PRT
<213> ORGANISM: Artificial Sequence
<220> FEATURE:
<223> OTHER INFORMATION: Synthesized Sequence

<400> SEQUENCE: 81

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Tyr Trp Val Arg Gln Ala Pro Gly Lys Gly Leu Glu Trp Val
        35                  40                  45

Ser Asn Ile Lys Gln Asp Gly Ile Asn Thr Gly Gly Thr Ser Glu
    50                  55                  60

Lys Tyr Tyr Val Asp Ser Val Lys Gly Arg Phe Thr Ile Ser Arg Asp
65                  70                  75                  80

Asn Ala Lys Asn Thr Leu Tyr Leu Gln Met Asn Ser Leu Arg Ala Glu
                85                  90                  95

Asp Thr Ala Val Tyr Tyr Cys Ala Lys Gly Asp Tyr Tyr Cys Thr Thr
            100                 105                 110

Tyr Glu Cys Gln His Tyr Tyr Gly Met Asp Tyr Trp Gly Gln Gly Thr
        115                 120                 125

Thr Val Thr Val Ser Ser
    130

<210> SEQ ID NO 82
<211> LENGTH: 127
<212> TYPE: PRT
<213> ORGANISM: Artificial Sequence
<220> FEATURE:
<223> OTHER INFORMATION: Synthesized Sequence

<400> SEQUENCE: 82

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Tyr Trp Val Arg Gln Ala Pro Gly Lys Gly Leu Glu Trp Val
        35                  40                  45

Ser Ser Ile Glu Asp Ser Ser Glu Thr Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Tyr Cys Thr Thr Tyr Glu Cys Gln His Tyr Tyr
            100                 105                 110

Gly Met Asp Tyr Trp Gly Gln Gly Thr Thr Val Thr Val Ser Ser
        115                 120                 125

<210> SEQ ID NO 83
<211> LENGTH: 118
<212> TYPE: PRT
<213> ORGANISM: Artificial Sequence
```

```
<220> FEATURE:
<223> OTHER INFORMATION: Synthesized Sequence

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Phe Ser Ile Asn
            20                  25                  30

Ala Met Asn Trp Tyr Arg Gln Ala Pro Gly Lys Gly Thr Glu Trp Val
        35                  40                  45

Ala Gln Ile Thr Asp Glu Gly Ile Thr Asn Tyr Val Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Phe Val Ile Thr Thr Thr Ser Glu Ile Tyr Trp Gly Gln Gly Thr
            100                 105                 110

Thr Val Thr Val Ser Ser
        115

<210> SEQ ID NO 84
<211> LENGTH: 128
<212> TYPE: PRT
<213> ORGANISM: Artificial Sequence
<220> FEATURE:
<223> OTHER INFORMATION: Synthesized Sequence

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Tyr Trp Val Arg Gln Ala Pro Gly Lys Gly Leu Glu Trp Val
        35                  40                  45

Ser Ser Ile Glu Asp Ser Ser Thr Glu Thr Tyr Tyr Thr Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Asp Tyr Cys Thr Thr Tyr Glu Cys Gln His Tyr
            100                 105                 110

Tyr Gly Met Asp Tyr Trp Gly Gln Gly Thr Thr Val Thr Val Ser Ser
        115                 120                 125

<210> SEQ ID NO 85
<211> LENGTH: 129
<212> TYPE: PRT
<213> ORGANISM: Artificial Sequence
<220> FEATURE:
<223> OTHER INFORMATION: Synthesized Sequence

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

Trp Met Tyr Trp Val Arg Gln Ala Pro Gly Lys Gly Leu Glu Trp Val
            35                  40                  45

Ser Ser Ile Glu Asp Ser Ser Ile Thr Glu Thr Thr Tyr Tyr Thr Asp
 50                  55                  60

Ser Val Lys Gly Arg Phe Thr Ile Ser Arg Asp Asn Ala Lys Asn Thr
65                   70                  75                  80

Leu Tyr Leu Gln Met Asn Ser Leu Arg Ala Glu Asp Thr Ala Val Tyr
                85                  90                  95

Tyr Cys Ala Lys Gly Asp Tyr Tyr Cys Thr Thr Tyr Glu Cys Gln His
            100                 105                 110

Tyr Tyr Gly Met Asp Tyr Trp Gly Gln Gly Thr Thr Val Thr Val Ser
            115                 120                 125

Ser

<210> SEQ ID NO 86
<211> LENGTH: 129
<212> TYPE: PRT
<213> ORGANISM: Artificial Sequence
<220> FEATURE:
<223> OTHER INFORMATION: Synthesized Sequence

<400> SEQUENCE: 86

Gln Val Gln Leu Gln Glu Ser Gly Gly Gly Leu Val Gln Pro Gly Gly
1               5                   10                  15

Ser Leu Arg Leu Ser Cys Gln Ala Ser Gly Phe Thr Phe Arg Arg Tyr
            20                  25                  30

Trp Met Tyr Trp Val Arg Gln Ala Pro Gly Lys Gly Leu Glu Trp Val
            35                  40                  45

Ser Ser Ile Asn Asp Gly Gly Asp Asp Ser Thr Tyr Tyr Ala Asp
 50                  55                  60

Ser Val Lys Gly Arg Phe Thr Ile Ser Arg Asp Asn Ala Lys Asn Thr
65                   70                  75                  80

Leu Tyr Leu Gln Met Asn Ser Val Lys Ser Glu Asp Thr Ala Val Tyr
                85                  90                  95

Tyr Cys Ala Lys Gly Asp Tyr Tyr Cys Thr His Tyr Glu Cys Gln His
            100                 105                 110

Tyr Tyr Gly Met Asp Tyr Trp Gly Lys Gly Thr Leu Val Thr Val Ser
            115                 120                 125

Ser

<210> SEQ ID NO 87
<211> LENGTH: 126
<212> TYPE: PRT
<213> ORGANISM: Artificial Sequence
<220> FEATURE:
<223> OTHER INFORMATION: Synthesized Sequence

<400> SEQUENCE: 87

Glu Val Gln Leu Val Gln Ser Gly Gly Asp Leu Val Gln Pro Gly Gly
1               5                   10                  15

Ser Leu Arg Leu Ser Cys Ala Ala Ser Gly Phe Thr Phe Ser Lys Tyr
            20                  25                  30

Trp Met Tyr Trp Val Arg Gln Thr Pro Gly Lys Gly Leu Glu Trp Val
            35                  40                  45

Ser Gly Ile Arg Thr Ser Gly Asp Thr Asp Tyr Ala Asp Ser Val Lys
 50                  55                  60

Gly Arg Phe Thr Ile Ser Arg Asp Asn Ala Lys Asn Thr Leu Tyr Leu

```
                65                  70                  75                  80
Gln Met Asn Ser Leu Lys Ser Glu Asp Thr Ala Val Tyr Tyr Cys Ala
                    85                  90                  95

Lys Gly Asp Tyr Tyr Cys Thr Thr Tyr Glu Cys Gln His Tyr Tyr Gly
                100                 105                 110

Met Asp Tyr Trp Gly Lys Gly Thr Thr Val Thr Val Ser Ser
            115                 120                 125

<210> SEQ ID NO 88
<211> LENGTH: 118
<212> TYPE: PRT
<213> ORGANISM: Artificial Sequence
<220> FEATURE:
<223> OTHER INFORMATION: Synthesized Sequence

<400> SEQUENCE: 88

Gln Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Phe Ser Ile Asn
            20                  25                  30

Ala Met Asn Trp Tyr Arg Gln Ala Pro Gly Lys Gly Thr Glu Trp Val
        35                  40                  45

Ala Gln Ile Thr Asp Glu Gly Ile Thr Asn Tyr Val Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Phe Val Ile Thr Thr Thr Ser Glu Ile Tyr Trp Gly Gln Gly Thr
                100                 105                 110

Thr Val Thr Val Ser Ser
            115

<210> SEQ ID NO 89
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 89

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Ala Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ala Ser Val Pro Leu
                85                  90                  95

Thr Phe Gly Gly Gly Thr Lys Leu Glu Ile Lys
                100                 105

<210> SEQ ID NO 90
<211> LENGTH: 107
```

<212> TYPE: PRT
<213> ORGANISM: Artificial Sequence
<220> FEATURE:
<223> OTHER INFORMATION: Synthesized Sequence

<400> SEQUENCE: 90

```
Val Ile Trp Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105
```

<210> SEQ ID NO 91
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 91

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105
```

<210> SEQ ID NO 92
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 92

```
Asn Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Gly Ser Trp
            20                  25                  30

Leu Ala Trp Tyr Gln Gln Lys Pro Gly His Ala Pro Lys Leu Leu Ile
        35                  40                  45

Tyr Ala Ala Ser Thr Leu Gln Arg Gly Val Pro Ser Arg Phe Ser Gly
```

-continued

```
                50                  55                  60
Gly Gly Tyr Gly Thr Glu Phe Thr Leu Thr Ile Asp Ser Leu Gln Ser
65                  70                  75                  80

Glu Asp Phe Ala Thr Tyr Phe Cys Gln Gln Ser His Ser Leu Pro Leu
                85                  90                  95

Thr Phe Gly Gly Gly Thr Gln Gly Gly Asn Gln
            100                 105
```

<210> SEQ ID NO 93
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 93

```
Asp Ile Val Met Thr Gln Ser Pro Ser Ser Leu Ser Ala Ser Val Gly
1               5                   10                  15

Asp Thr Val Thr Ile Thr Cys Arg Ala Ser Gln Ser Ile Ser Arg Asn
                20                  25                  30

Leu Asn Trp Tyr Gln Gln Lys Pro Gly Lys Ala Pro Asn Leu Leu Ile
            35                  40                  45

Tyr Thr Ala Ser Thr Leu Gln Ser Gly Val Pro Ser Arg Phe Ser Gly
        50                  55                  60

Ser Gly Ser Gly Thr Asp Phe Thr Leu Thr Ile Ser Thr Leu Gln Pro
65                  70                  75                  80

Glu Asp Phe Ala Ile Tyr His Cys Gln Gln Ser Tyr Arg Thr Pro Phe
                85                  90                  95

Thr Phe Gly Gln Gly Thr Lys Val Glu Ile Lys
            100                 105
```

<210> SEQ ID NO 94
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 94

```
Asp Ile Gln Leu Thr Gln Ser Pro Ser Ala Val Ser Ala Ser Val Gly
1               5                   10                  15

Asp Arg Val Thr Ile Thr Cys Arg Ala Ser Gln His Ile Ser Ser Trp
                20                  25                  30

Leu Ala Trp Phe Gln Gln Lys Pro Gly Lys Ala Pro Lys Leu Leu Ile
            35                  40                  45

Tyr Ala Ala Ser Ser Leu Gln Ser Gly Val Pro Pro Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Thr Ser Phe Pro Leu
                85                  90                  95

Thr Phe Gly Gln Gly Thr Lys Val Glu Ile Lys
            100                 105
```

<210> SEQ ID NO 95
<211> LENGTH: 107
<212> TYPE: PRT
<213> ORGANISM: Artificial Sequence
<220> FEATURE:

<223> OTHER INFORMATION: Synthesized Sequence

<400> SEQUENCE: 95

```
Ala Ile Arg Met Thr Gln Ser Pro Ser Ser Leu Ser Ala Ser Val Gly
1               5                   10                  15
Asp Arg Val Thr Ile Thr Cys Arg Ala Ser Gln Ser Ile Ser His Tyr
            20                  25                  30
Leu Asn Trp Tyr Gln Trp Lys Pro Gly Lys Val Pro Lys Leu Leu Ile
        35                  40                  45
Tyr Ala Ala Thr Arg Leu Gln Ser Gly Val Pro Pro Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Ile Tyr Phe Cys Gln Gln Ser Tyr Ser Ala Leu Phe
                85                  90                  95
Thr Phe Gly Pro Gly Thr Lys Val Asp Ile Lys
            100                 105
```

<210> SEQ ID NO 96
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 96

```
Glu Ile Val Met Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Arg Pro Gly Gln Ala Pro Arg Leu Leu Ile
        35                  40                  45
Tyr Asp Thr Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Pro
                85                  90                  95
Thr Phe Gly Gln Gly Thr Lys Val Glu Ile Lys
            100                 105
```

<210> SEQ ID NO 97
<211> LENGTH: 108
<212> TYPE: PRT
<213> ORGANISM: Artificial Sequence
<220> FEATURE:
<223> OTHER INFORMATION: Synthesized Sequence

<400> SEQUENCE: 97

```
Glu Thr Thr Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln His Lys Pro Gly Gln Ala Pro Arg Leu Leu
        35                  40                  45
Ile Tyr Gly Thr Ser Ser Arg Ala Thr Gly Ile Pro Asp Arg Phe Ser
    50                  55                  60
Gly Ser Gly Ser Gly Thr Asp Phe Thr Leu Thr Ile Asp Arg Leu Glu
```

-continued

```
                65                  70                  75                  80
Pro Glu Asp Phe Ala Val Tyr Tyr Cys Gln Gln Ser Asp Thr Ser Pro
                    85                  90                  95

Arg Val Phe Gly Gly Gly Thr Lys Val Glu Ile Lys
                100                 105

<210> SEQ ID NO 98
<211> LENGTH: 108
<212> TYPE: PRT
<213> ORGANISM: Artificial Sequence
<220> FEATURE:
<223> OTHER INFORMATION: Synthesized Sequence

<400> SEQUENCE: 98

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Leu Ser Ile Pro Gln
                85                  90                  95

Val Thr Phe Gly Gly Gly Thr Lys Val Asp Ile Lys
                100                 105

<210> SEQ ID NO 99
<211> LENGTH: 110
<212> TYPE: PRT
<213> ORGANISM: Artificial Sequence
<220> FEATURE:
<223> OTHER INFORMATION: Synthesized Sequence

<400> SEQUENCE: 99

Gln Ser Val Leu Thr Gln Pro Pro Ser Val Ser Ala Ala Pro Ala Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Val Pro Gly Thr Ala Pro Glu Leu Leu
            35                  40                  45

Ile Tyr Asp Asn Tyr Arg Arg Pro Ser Gly Ile Pro Asp Arg Phe Ser
        50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Gln Leu Thr Val Leu
                100                 105                 110

<210> SEQ ID NO 100
<211> LENGTH: 104
<212> TYPE: PRT
<213> ORGANISM: Artificial Sequence
<220> FEATURE:
<223> OTHER INFORMATION: Synthesized Sequence

<400> SEQUENCE: 100
```

```
Glu Leu Thr Gln Pro Ser Ala Val Ser Val Ser Leu Gly Gln Thr Val
1               5                   10                  15

Arg Ile Thr Cys Gln Gly Asp Arg Ile Glu Asn Tyr Tyr Thr Ser Trp
                20                  25                  30

Tyr Gln Gln Lys Pro Gly Gln Ala Pro Val Leu Val Ile Tyr Gly Asn
            35                  40                  45

Ala Asn Arg Pro Ser Gly Ile Pro Glu Arg Phe Ser Gly Ser Ser Ser
        50                  55                  60

Gly Asn Thr Ala Ser Leu Thr Ile Thr Gly Ala Gln Ala Glu Asp Glu
65                  70                  75                  80

Ala Asp Tyr Tyr Cys Gln Ser Gly Ser Ser Thr Glu Asn Ile Phe Gly
                85                  90                  95

Gly Gly Thr Lys Leu Thr Val Leu
                100
```

<210> SEQ ID NO 101
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 101

```
Leu Pro Val Leu Thr Gln Pro Ser Ala Val Ser Val Ser Leu Gly Gln
1               5                   10                  15

Thr Ala Arg Ile Thr Cys Gln Gly Asp Arg Ile Glu Asn Tyr Tyr Thr
                20                  25                  30

Ser Trp Phe Arg Gln Lys Pro Gly Gln Ala Pro Val Leu Val Ile Tyr
            35                  40                  45

Gly Asn Ala Asn Arg Pro Ser Gly Val Pro Glu Arg Phe Ser Gly Ser
        50                  55                  60

Ser Ser Gly Val Thr Ala Thr Leu Thr Ile Ser Gly Ala Gln Ala Glu
65                  70                  75                  80

Asp Glu Ala Asp Tyr Tyr Cys Gln Ser Gly Ser Ser Thr Glu Asn Ile
                85                  90                  95

Phe Gly Gly Gly Thr Lys Leu Thr Val Leu Gln
                100                 105
```

<210> SEQ ID NO 102
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 102

```
Leu Pro Val Leu Thr Gln Pro Ser Ala Val Ser Val Ser Leu Gly Gln
1               5                   10                  15

Thr Ala Arg Ile Thr Cys Gln Gly Asp Arg Ile Glu Asn Tyr Tyr Thr
                20                  25                  30

Ser Trp Phe Arg Gln Lys Pro Gly Gln Ala Pro Val Leu Val Ile Tyr
            35                  40                  45

Gly Asn Ala Asn Arg Pro Ser Gly Val Pro Glu Arg Phe Ser Gly Ser
        50                  55                  60

Ser Ser Gly Val Thr Ala Thr Leu Thr Ile Ser Gly Ala Gln Ala Glu
65                  70                  75                  80

Asp Glu Ala Asp Tyr Tyr Cys Gln Ser Gly Ser Ser Thr Glu Asn Ile
```

<210> SEQ ID NO 103
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 103

```
Leu Pro Val Leu Thr Gln Pro Ser Ala Val Ser Val Ser Leu Gly Gln
1               5                   10                  15

Thr Ala Arg Ile Thr Cys Gln Gly Asp Arg Ile Glu Asn Tyr Tyr Thr
            20                  25                  30

Ser Trp Phe Arg Gln Lys Pro Gly Gln Ala Pro Val Leu Val Ile Tyr
        35                  40                  45

Gly Asn Ala Asn Arg Pro Ser Gly Val Pro Glu Arg Phe Ser Gly Ser
    50                  55                  60

Ser Ser Gly Val Thr Ala Thr Leu Thr Ile Ser Gly Ala Gln Ala Glu
65                  70                  75                  80

Asp Glu Ala Asp Tyr Tyr Cys Gln Ser Gly Ser Ser Thr Glu Asn Ile
                85                  90                  95

Phe Gly Gly Gly Thr Lys Leu Thr Val Leu Gln
            100                 105
```

<210> SEQ ID NO 104
<211> LENGTH: 110
<212> TYPE: PRT
<213> ORGANISM: Artificial Sequence
<220> FEATURE:
<223> OTHER INFORMATION: Synthesized Sequence

<400> SEQUENCE: 104

```
Asn Phe Met Leu Thr Gln Pro Pro Ser Val Ser Gly Ser Pro Gly Gln
1               5                   10                  15

Lys Phe Thr Ile Ser Cys Thr Gly Ser Ser Ser Asn Ile Gly Asp Asn
            20                  25                  30

Tyr Val Asn Trp Tyr Gln His Leu Pro Gly Thr Ala Pro Lys Leu Leu
        35                  40                  45

Ile Tyr Ser Asn Ser Asn Arg Ala Ser Gly Val Pro Asp Arg Phe Ser
    50                  55                  60

Gly Ser Ser Ser Gly Gly Thr Ala Thr Leu Thr Ile Ser Gly Ala Gln
65                  70                  75                  80

Ala Glu Asp Glu Ala Asp Tyr Tyr Cys Gln Ser Tyr Glu Ile Ser Gly
                85                  90                  95

Tyr Pro Val Phe Gly Gly Gly Thr Lys Leu Thr Val Leu Gln
            100                 105                 110
```

<210> SEQ ID NO 105
<211> LENGTH: 112
<212> TYPE: PRT
<213> ORGANISM: Artificial Sequence
<220> FEATURE:
<223> OTHER INFORMATION: Synthesized Sequence

<400> SEQUENCE: 105

```
Glu Ile Val Leu Thr Gln Ser Pro Leu Ser Leu Pro Val Thr Leu Gly
1               5                   10                  15
```

Gln Pro Ala Ser Ile Ser Cys Thr Ser Ser Gln Ser Leu Val Tyr Arg
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asp Arg Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ser Thr Phe Gly Gln Gly Thr Lys Leu Glu Ile Lys
            100                 105                 110

<210> SEQ ID NO 106
<211> LENGTH: 108
<212> TYPE: PRT
<213> ORGANISM: Artificial Sequence
<220> FEATURE:
<223> OTHER INFORMATION: Synthesized Sequence

<400> SEQUENCE: 106

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Gln
                85                  90                  95

Leu Thr Phe Gly Gly Gly Thr Lys Val Glu Ile Lys
            100                 105

<210> SEQ ID NO 107
<211> LENGTH: 116
<212> TYPE: PRT
<213> ORGANISM: Artificial Sequence
<220> FEATURE:
<223> OTHER INFORMATION: Synthesized Sequence

<400> SEQUENCE: 107

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
 50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys

```
              100                 105                 110

Tyr Arg Val Val
            115

<210> SEQ ID NO 108
<211> LENGTH: 220
<212> TYPE: PRT
<213> ORGANISM: Artificial Sequence
<220> FEATURE:
<223> OTHER INFORMATION: Synthesized Sequence

<400> SEQUENCE: 108

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 109
<211> LENGTH: 118
<212> TYPE: PRT
<213> ORGANISM: Artificial Sequence
<220> FEATURE:
<223> OTHER INFORMATION: BCD106-02_L.Alecto.VHHSel2_MP1_H10_78

<400> SEQUENCE: 109

Gln Val Lys Leu Glu Glu Ser Gly Gly Gly Leu Val Gln Pro Gly Gly
1               5                   10                  15

Ser Leu Arg Leu Ser Cys Ala Ala Ser Arg Ser Ile Ser Ser Ile Asn
            20                  25                  30

Ala Met Asn Trp Tyr Arg Gln Ala Pro Gly Lys Arg Arg Glu Trp Val
        35                  40                  45

Ala Gln Ile Thr Gly Glu Gly Ile Thr Asn Tyr Arg Asp Ser Val Lys
    50                  55                  60
```

```
Gly Arg Phe Thr Ile Thr Ser Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Phe Val Ile His Thr Thr Ser Glu Val Tyr Trp Gly Gln Gly Thr
            100                 105                 110

Leu Val Thr Val Ser Ser
            115
```

<210> SEQ ID NO 110
<211> LENGTH: 118
<212> TYPE: PRT
<213> ORGANISM: Artificial Sequence
<220> FEATURE:
<223> OTHER INFORMATION: BCD106-02_L.Alecto.VHHSel2_MP1_G5_37

<400> SEQUENCE: 110

```
Ala Val Gln Leu Val Asp Ser Gly Gly Gly Leu Val Gln Pro Gly Gly
1               5                   10                  15

Ser Leu Arg Leu Ser Cys Ala Ala Ser Arg Ser Ile Phe Ser Ile Asn
            20                  25                  30

Ala Met Asn Trp Tyr Arg Gln Ala Pro Gly Asn Arg Arg Glu Trp Val
        35                  40                  45

Ala Gln Ile Thr Asp Glu Gly Ile Thr Asn Tyr Val Asp Ser Val Lys
    50                  55                  60

Gly Arg Phe Thr Ile Thr Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Phe Val Ile Thr Thr Thr Ser Glu Ile Tyr Trp Gly Gln Gly Thr
            100                 105                 110

Thr Val Thr Val Ser Ser
            115
```

<210> SEQ ID NO 111
<211> LENGTH: 118
<212> TYPE: PRT
<213> ORGANISM: Artificial Sequence
<220> FEATURE:
<223> OTHER INFORMATION: BCD106-02_L.Alecto.VHHSel2_MP1_G7_53

<400> SEQUENCE: 111

```
Gln Val Lys Leu Glu Glu Ser Gly Gly Gly Leu Val Gln Pro Gly Gly
1               5                   10                  15

Ser Leu Thr Leu Ser Cys Ala Ala Ser Gly Ile Ile Ser Ser Ile Asn
            20                  25                  30

Ala Met Asn Trp Tyr Arg Gln Ala Pro Gly Lys Arg Arg Glu Trp Val
        35                  40                  45

Ala Gln Ile Thr Gly Glu Gly Ile Thr Asn Cys Arg Asp Ser Trp Lys
    50                  55                  60

Gly Arg Phe Ser Ile Thr Ser Asp Ser Ala Asn Asn Thr Met Tyr Leu
65                  70                  75                  80

Gln Met Asn Asn Leu Lys Pro Asp Asp Thr Ala Val Tyr Tyr Cys Asn
                85                  90                  95

Ala Phe Val Ile His Thr Thr Ser Glu Ile Tyr Trp Gly Leu Gly Thr
            100                 105                 110

Thr Val Thr Val Ser Ser
            115
```

<210> SEQ ID NO 112
<211> LENGTH: 118
<212> TYPE: PRT
<213> ORGANISM: Artificial Sequence
<220> FEATURE:
<223> OTHER INFORMATION: BCD106-02_L.Alecto.VHHSel2_MP1_F10_76

<400> SEQUENCE: 112

Asp Val Gln Leu Val Glu Ser Gly Gly Gly Leu Val Gln Pro Gly Gly
1               5                   10                  15

Ser Leu Arg Leu Ser Cys Ala Ala Ser Arg Asn Ile Phe Ser Ile Asn
            20                  25                  30

Ala Met Asn Trp Tyr Arg Gln Ala Pro Gly Lys Arg Arg Glu Trp Val
        35                  40                  45

Ala Gln Ile Thr Ser Glu Gly Ile Thr Asn Tyr Val Asp Ser Val Lys
    50                  55                  60

Gly Arg Phe Thr Ile Thr Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Phe Val Ile Thr Ala Ser Ser Glu Val Tyr Trp Gly Gln Gly Thr
            100                 105                 110

Thr Val Thr Val Ser Ser
        115

<210> SEQ ID NO 113
<211> LENGTH: 118
<212> TYPE: PRT
<213> ORGANISM: Artificial Sequence
<220> FEATURE:
<223> OTHER INFORMATION: BCD106-02_L.Alecto.VHHSel2_MP1_C7_49

<400> SEQUENCE: 113

Ala Val Gln Leu Val Asp Ser Gly Gly Gly Leu Val Gln Pro Gly Gly
1               5                   10                  15

Ser Leu Arg Leu Ser Cys Ala Ala Ser Arg Ser Ile Phe Ser Ile Asn
            20                  25                  30

Ala Met Asn Trp Tyr Arg Gln Ala Pro Gly Asn Arg Arg Glu Trp Val
        35                  40                  45

Ala Gln Ile Thr Asp Glu Gly Ile Thr Asn Tyr Val Asp Ser Val Lys
    50                  55                  60

Gly Arg Phe Thr Ile Thr Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Phe Val Ile Thr Thr Thr Ser Glu Ile Tyr Trp Gly Gln Gly Thr
            100                 105                 110

Thr Val Thr Val Ser Ser
        115

<210> SEQ ID NO 114
<211> LENGTH: 118
<212> TYPE: PRT
<213> ORGANISM: Artificial Sequence
<220> FEATURE:
<223> OTHER INFORMATION: BCD106-02_L.Alecto.VHHSel2_MP1_B9_64

<400> SEQUENCE: 114

-continued

Asp Val Gln Leu Val Glu Ser Gly Gly Gly Leu Val Gln Pro Gly Gly
1               5                   10                  15

Ser Leu Thr Leu Ser Cys Ala Ala Ser Arg Asn Ile Phe Arg Ile Asn
            20                  25                  30

Ala Met Asn Trp Tyr Arg Gln Ala Pro Gly Lys Arg Arg Glu Trp Val
        35                  40                  45

Ala Pro Ile Thr Ser Glu Gly Ile Thr Asn Tyr Val Asp Ser Val Lys
    50                  55                  60

Gly Arg Phe Thr Ile Thr Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Cys Leu Ile Thr Ala Ser Ser Glu Val Tyr Trp Gly Gln Gly Thr
            100                 105                 110

Leu Val Thr Val Ser Ser
            115

<210> SEQ ID NO 115
<211> LENGTH: 118
<212> TYPE: PRT
<213> ORGANISM: Unknown
<220> FEATURE:
<223> OTHER INFORMATION: Wild VHH47

<400> SEQUENCE: 115

Ala Val Gln Leu Val Asp Ser Gly Gly Gly Leu Val Gln Pro Gly Gly
1               5                   10                  15

Ser Leu Arg Leu Ser Cys Ala Ala Ser Arg Ser Ile Phe Ser Ile Asn
            20                  25                  30

Ala Met Asn Trp Tyr Arg Gln Pro Pro Gly Asn Arg Arg Glu Trp Val
        35                  40                  45

Ala Gln Ile Thr Asp Glu Gly Ile Thr Asn Tyr Val Asp Ser Val Lys
    50                  55                  60

Gly Arg Phe Thr Ile Thr Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Phe Val Ile Thr Thr Thr Ser Glu Ile Tyr Trp Gly Gln Gly Thr
            100                 105                 110

Thr Val Thr Val Ser Ser
            115

<210> SEQ ID NO 116
<211> LENGTH: 118
<212> TYPE: PRT
<213> ORGANISM: Artificial Sequence
<220> FEATURE:
<223> OTHER INFORMATION: VHH47Opt1

<400> SEQUENCE: 116

Ala Val Gln Leu Val Asp Ser Gly Gly Gly Leu Val Gln Pro Gly Gly
1               5                   10                  15

Ser Leu Arg Leu Ser Cys Ala Ala Ser Arg Ser Ile Phe Ser Ile Asn
            20                  25                  30

Ala Met Asn Trp Tyr Arg Gln Ala Pro Gly Lys Gly Thr Glu Trp Val
        35                  40                  45

Ala Gln Ile Thr Asp Glu Gly Ile Thr Asn Tyr Val Asp Ser Val Lys
    50                  55                  60

Gly Arg Phe Thr Ile Thr Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Phe Val Ile Thr Thr Thr Ser Glu Ile Tyr Trp Gly Gln Gly Thr
            100                 105                 110

Thr Val Thr Val Ser Ser
        115

<210> SEQ ID NO 117
<211> LENGTH: 118
<212> TYPE: PRT
<213> ORGANISM: Artificial Sequence
<220> FEATURE:
<223> OTHER INFORMATION: VHH47Opt2

<400> SEQUENCE: 117

Gln Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Phe Ser Ile Asn
            20                  25                  30

Ala Met Asn Trp Tyr Arg Gln Ala Pro Gly Lys Gly Thr Glu Trp Val
        35                  40                  45

Ala Gln Ile Thr Asp Glu Gly Ile Thr Asn Tyr Val Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Phe Val Ile Thr Thr Thr Ser Glu Ile Tyr Trp Gly Gln Gly Thr
            100                 105                 110

Thr Val Thr Val Ser Ser
        115

<210> SEQ ID NO 118
<211> LENGTH: 118
<212> TYPE: PRT
<213> ORGANISM: Artificial Sequence
<220> FEATURE:
<223> OTHER INFORMATION: VHH47Opt3

<400> SEQUENCE: 118

Gln Val Gln Leu Val Glu Ser Asp Gly Gly Leu Val Gln Pro Gly Gly
1               5                   10                  15

Ser Leu Arg Leu Ser Cys Ala Ala Ser Arg Phe Thr Phe Ser Ile Asn
            20                  25                  30

Ala Met Asn Trp Val Arg Gln Ala Pro Gly Lys Gly Leu Glu Trp Val
        35                  40                  45

Ser Gln Ile Thr Asp Glu Gly Ile Thr Asn Tyr Val Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Phe Val Ile Thr Thr Thr Ser Glu Ile Tyr Trp Gly Gln Gly Thr
            100                 105                 110

Leu Val Thr Val Ser Ser

```
<210> SEQ ID NO 119
<211> LENGTH: 122
<212> TYPE: PRT
<213> ORGANISM: Artificial Sequence
<220> FEATURE:
<223> OTHER INFORMATION: VH(BCD135)

<400> SEQUENCE: 119

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Asp Ile Ser Trp Ser Gly Ser Asn Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Ala Pro Leu Leu Leu Ala Met Thr Phe Gly Val Gly Ser Trp
            100                 105                 110

Gly Gln Gly Thr Leu Val Thr Val Ser Ser
            115                 120

<210> SEQ ID NO 120
<211> LENGTH: 110
<212> TYPE: PRT
<213> ORGANISM: Artificial Sequence
<220> FEATURE:
<223> OTHER INFORMATION: VL(BCD135)

<400> SEQUENCE: 120

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Thr Val Thr Ala Ile
            20                  25                  30

Asn Tyr Pro Gly Trp Tyr Gln Gln Thr Pro Gly Gln Ala Pro Arg Thr
        35                  40                  45

Leu Ile Tyr Asn Thr Asn Thr Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Ala Glu Asp Glu Ala Asp Tyr Tyr Cys Ala Leu Tyr Met Gly Asn
                85                  90                  95

Gly Gly His Met Phe Gly Gly Gly Thr Lys Leu Thr Val Leu
            100                 105                 110
```

BISPECIFIC ANTIBODIES WITH SPECIFIC BINDING TO CD47 AND PD-L1

FIELD OF INVENTION

The present invention relates to the field of biotechnology, in particular to antibodies or antigen-binding fragments thereof, and to use thereof. More particularly, the present invention relates to antibodies that specifically bind to CD47 and PD-L1. The invention also relates to a nucleic acid encoding said antibody or antigen-binding fragment thereof, an expression vector, a method for obtaining the antibody, and use of said antibodies and compositions in cancer therapies.

BACKGROUND OF THE INVENTION

Providing two separate signals to T-cells is a widespread model of lymphocytic activation of the remaining T-lymphocytes with antigen-presenting cells (APC). This model fully provides for the discrimination of self from non-self and immune tolerance. The primary signal, or antigen-specific signal, is transmitted through the T cell receptor (TCR) following recognition of foreign antigen peptide presented in the context of the major histocompatibility-complex (MHC). The second or co-stimulatory signal is delivered to T cells by co-stimulatory molecules expressed on antigen-presenting cells (APCs), and induces T cells to stimulate clonal expansion, cytokine secretion and effector function. In the absence of co-stimulation, T cells may become immune to antigen stimulation, they cause an effective immune response, and this may further lead to depletion or resistance to foreign antigens.

In the two-signal model, T cells receive both signals: positive and negative secondary co-stimulatory signals. The regulation of such positive and negative signals is critical to maximize the host's protective immune responses, while maintaining immune tolerance and preventing autoimmunity. Negative secondary signals seem necessary for inducing T cell tolerance, while positive signals stimulate T cell activation. While the simple two-signal model still provides a valid explanation for naive lymphocytes, the immune response is a dynamic process, and co-stimulatory signals to antigen-exposed T cells can also be provided. The mechanism of co-stimulation is of interest from a therapeutic point of view since it has been shown that manipulating the co-stimulatory signals provides a means of either enhancing or terminating the immune response. Recently, T-cell dysfunction or anergy has been found to occur simultaneously with the induced and persistent expression of the inhibitory receptor, polypeptide 1 programmed cell death (PD-1). As a result, therapeutic targeting of PD-1 and other molecules transmitting a signal through interaction with PD-1, such as programmed death-ligand 1 (PD-L1) or programmed death-ligand 2 (PD-L2) is an area of intense interest.

PD-L1 is overexpressed in a plurality of malignancies and is often associated with poor prognosis. Interestingly, the majority of tumor infiltrating T lymphocytes predominantly express PD-1, in contrast to T lymphocytes in normal tissues and peripheral blood T lymphocytes indicating that positive regulation of PD-1 on tumor-reactive T cells can contribute to impaired immune response. This may be due to exploitation of PD-L1 signaling pathway mediated by tumor cells expressing PD-L1 and interacting with T-cells expressing PD-1, with a total weakening of T-cell activation and evasion of immune surveillance. Therefore, inhibition of the PD-L1/PD-1 interaction can enhance CD8+ T cell-mediated killing of tumors.

Therapeutic targeting of PD-1, and other molecules transmitting a signal through interaction with PD-1, such as PD-L1 and PD-L2 is an area of intense interest Inhibition of PD-L1 signals has been suggested as a means to increase T cell immunity (for example, antitumor immunity) for the treatment of cancer and infection, including both acute and chronic infection. Inhibitors that block the PD-L1/PD-1 interaction are known, inter alia, from WO2001014557, WO2002086083, WO2007005874, WO2010036959, WO2010077634 and WO2011066389. However, no optimal therapeutic agent targeting this pathway has yet been commercialized, and this is a significant unmet medical need.

CD47 is a cell surface glycoprotein which binds to SIRPα (alias SHPS-1) and SIRPγ on corresponding cells. This interaction leads to negative regulation of immune cell function or can mediate cellular adhesion and migration. The use of CD47 as a biological agent in the treatment of autoimmune disorders (WO 1999/040940) has been proposed. In contrast, is very little data on the possible use of CD47 ligands, such as SIRPα for similar therapeutic purposes. One explanation is the ubiquitous expression of CD47, which may interfere with the use of CD47 binding polypeptides as potential drugs. Data published by Yu et all (J. Invest. Dermatol., 126:797-807 (2006) suggest that a fusion protein consisting of the extracellular domains of SIRPα fused to an immunoglobulin Fc domain can prevent migration from skin derived dendritic cells (DCs) to draining lymph nodes in mice, and thereby attenuate (at least partially) contact hypersensitivity response in mice. Migration and function of DCs are important for immune or inflammatory responses. In a painful condition, these exacerbated DC responses can lead to the maintenance of the disease. Interfering with migration of pathogenic DCs from tissue to lymphoid organs would be an attractive opportunity to stop the vicious cycle driving autoimmune or inflammatory diseases.

CD47, also known as integrin-associated protein (TAP), ovarian cancer antigen OA3, Rh-related antigen and MER6, is a transmembrane receptor that penetrates the membrane several times and belongs to the immunoglobulin superfamily. CD47 expression and/or activity have been observed in a number of diseases and disorders. Accordingly, there exists a need for therapies that target CD47. In addition, due to expression of CD47 on platelets, there is also a need for CD47-targeting therapies (e.g., antibodies) that do not cause significant levels of platelet depletion, hemagglutination, red blood cell depletion, and/or anemia when administered to a subject.

Known antibodies inhibiting the interaction between CD47 and SIRPα ligand have been described in the following sources: applications WO2014123580, WO2013119714, WO2015191861, WO2011143624, WO/2014/093678, WO2017053423.

Also known are various sources describing multispecific antibodies, for example, WO/2014/087248 describes a bispecific antibody that is specific for CD47 and CD19, and WO2016023001 describes a bispecific antibody that is specific for CD47 and PD1. However, no possibility of production and efficient use of a multispecific antibody that specifically binds to CD47 and PD-L1 has been described.

In connection with the foregoing, the creation of new antibodies that effectively bind to CD47 and PD-L1 is relevant.

BRIEF SUMMARY OF INVENTION

The present invention related to binding molecule, for example, antibodies directed to binding to CD47 and PD-L1. Such antibodies can be used to treat a disease or disorder mediated by CD47 and PD-L1.

In one aspect, the present invention relates to a monoclonal antibody that specifically binds to CD47 and PD-L1 and comprises one binding site for CD47, and at least one binding site for PD-L1.

In some embodiments, an antibody of the present invention is a full-length antibody or antigen-binding fragment thereof.

In some embodiments, an antibody of the present invention includes one or two binding sites for PD-L1.

In some embodiments, a binding site for CD47 of an antibody of the present invention inhibits the interaction between CD47 receptor and SIRPα ligand, and/or a binding site for PD-L1 inhibits the interaction of PD-L1 with PD-1 receptor.

In some embodiments, a binding site for CD47 of an antibody of the present invention comprises a heavy chain variable domain that comprises CDR1, CDR2, CDR3 sequences, wherein CDR1 is a sequence that is at least 80% homologous to the sequence selected from the following group of SEQ ID NO: 1-4, i.e. CDR1 is a sequence selected from the group comprising SEQ ID NOs: 1-4 or a sequence selected from the group comprising SEQ ID NOs: 1-4 with 1 or 2 substitutions, wherein CDR2 is a sequence that is at least 80% homologous to the sequence selected from the following group of SEQ ID NOs: 6-15, i.e. CDR2 is a sequence selected from the group comprising SEQ ID NOs: 6-15 or a sequence selected from the group comprising SEQ ID NOs: 6-15 with 1, 2, 3, 4 or 5 substitutions, wherein CDR3 is a sequence that is at least 80% homologous to the sequence selected from the following group of SEQ ID NOs: 17-20, i.e. CDR3 is a sequence selected from the group comprising SEQ ID NOs: 17-20 or a sequence selected from the group comprising SEQ ID NOs: 17-20 with 1, 2 or 3 substitutions.

In some embodiments, the CD47 binding site for of an antibody of the present invention comprises a heavy chain variable domain that comprises CDR1, CDR2, CDR3 sequences, wherein CDR1 is a sequence selected from the following group of SEQ ID NOs: 1-4, wherein CDR2 is a sequence selected from the following group of SEQ ID NOs: 6-15, wherein CDR3 is a sequence selected from the following group of SEQ ID NOs: 17-20.

In some embodiments, the CD47 binding site of an antibody of the present invention comprises a heavy chain variable domain of claim 4, and a light chain variable domain that comprises CDR1, CDR2, CDR3 sequences, wherein CDR1 is a sequence that is at least 80% homologous to the sequence selected from the following group of SEQ ID NOs: 22-34, i.e. CDR1 is a sequence selected from the following group of SEQ ID NOs: 22-34 or a sequence selected from the following group of SEQ ID NOs: 22-34 with 1 or 2 substitutions, wherein CDR2 is a sequence that is at least 80% homologous to the sequence selected from the following group of SEQ ID NOs: 36-48, i.e. CDR2 is a sequence selected from the group comprising SEQ ID NOs: 36-48 or a sequence selected the following group of SEQ ID NOs: 36-48 with 1, 2 or 3 substitutions, wherein CDR3 is a sequence that is at least 80% homologous to the sequence selected from the following group of SEQ ID NOs: 50-64, i.e. CDR3 is the sequence of SEQ ID NOs: 50-64 or a sequence selected the following group of SEQ ID NOs: 50-64 with 1 or 2 substitutions.

In some embodiments, a binding site for CD47 of an antibody of the present invention includes a heavy chain variable domain of claim 4, and a light chain variable domain that comprises CDR1, CDR2, CDR3 sequences, wherein CDR1 is a sequence selected from the following group of SEQ ID NOs: 22-34, CDR2 is a sequence selected from the following group of SEQ ID NOs: 36-48, CDR3 is a sequence selected from the following group of SEQ ID NOs: 50-64.

In some embodiments, a binding site for CD47 of an antibody of the present invention includes a heavy chain variable domain that comprises sequences that are at least 90% homologous to the sequences selected from the following group of SEQ ID NOs: 66-88, and a light chain variable domain that comprises sequences that are at least 90% homologous to the sequences selected from the following group of SEQ ID NOs: 89-106.

In some embodiments, a binding site for CD47 of an antibody of the present invention includes a heavy chain variable domain that comprises sequences selected from the following group of SEQ ID NOs: 66-88, and a light chain variable domain that comprises sequences selected from the following group of SEQ ID NOs: 89-106.

In some embodiments, a binding site for PD-L1 of an antibody of the present invention includes a heavy chain variable domain that comprises sequences that are at least 80% homologous of the following sequences: SEQ ID NO: 5, SEQ ID NO: 16 and SEQ ID NO: 21, i.e. comprises amino acid sequences of SEQ ID NOs: 5, 16 and 21 or SEQ ID NO: 5 with 1 substitution, SEQ ID NO: 16 with 1, 2 or 3 substitutions, SEQ ID NO: 21 with 1, 2 or 3 substitutions, and a light chain variable domain that comprises sequences that are at least 80% homologous of the following sequences: SEQ ID NO: 35, SEQ ID NO: 49 and SEQ ID NO: 65, i.e. comprises amino acid sequences of SEQ ID NOs: 35, 49 and 65 or SEQ ID NO: 35 with 1, 2 or 3 substitutions, SEQ ID NO: 49 with 1 substitution, SEQ ID NO: 65 with 1 or 2 substitutions.

In some embodiments, a binding site to PD-L1 of an antibody of the present invention includes a heavy chain variable domain that comprises the following sequences: SEQ ID NO: 5, SEQ ID NO: 16 and SEQ ID NO: 21, and a light chain variable domain that comprises the following sequences: SEQ ID NO: 35, SEQ ID NO: 49 and SEQ ID NO: 65.

In some embodiments, a binding site to CD47 of an antibody of the present invention is Fab, scFv, scFab or isolated VH or VHH mono-domains.

In some embodiments, a binding site to PD-L1 of an antibody of the present invention is Fab, scFv, scFab or isolated VH or VHH mono-domains.

In some embodiments, an antibody of the present invention is characterized in that it stimulates antibody-dependent cellular cytotoxicity, macrophage-mediated phagocytosis, and/or T cell-mediated cytotoxicity the ratio of cells bearing CD47 and/or PD-L1 antigens on the surface.

In some embodiments, an antibody of the present invention is characterized in that it comprises an Fc portion comprising at least one mutation or modification that increases the antibody-dependent cellular cytotoxicity (ADCC), as compared to the same antibody without mutation or modification.

In some embodiments, an antibody of the present invention is intended to be used as a medicine for the treatment of cancer.

In one aspect, the present invention relates to a nucleic acid that encodes any of the above antibodies.

In some embodiments, a nucleic acid of the present invention is DNA.

In one aspect, the present invention relates to an expression vector that comprises the above nucleic acid.

In one aspect, the present invention relates to a method for obtaining a host cell for preparing any of the above antibodies, which including transformation of the cell with the vector of the present invention.

In one aspect, the present invention relates to a host cell for obtaining any of the above antibodies, which contains the nucleic acid described above.

In one aspect, the present invention relates to a method for obtaining any of the above antibodies, which consisting in the cultivation of the host cell in culture medium under conditions sufficient to obtain the specified antibody, if necessary, followed by isolation and purification of the obtained antibody.

In one aspect, the present invention relates to a pharmaceutical composition for the prevention or treatment a disease or disorder mediated by PD-L1 and CD47, comprising any of the above antibodies, in combination with one or several pharmaceutically acceptable excipients.

In some embodiments, a pharmaceutical composition of the invention intended for the prevention or treatment a disease or disorder mediated by PD-L1 and CD47, selected from the group of (HNSCC) head and neck squamous cell carcinoma, cervical cancer, cancer of unknown primary, glioblastoma, esophageal cancer, bladder cancer, TNBC (triple-negative breast cancer), CRC (colorectal cancer), hepatocellular carcinoma, melanoma, NSCLC (non-small cell lung cancer), kidney cancer, ovarian cancer, MSI CRC (colorectal cancer with with microsatellite instability), leukemia (acute leukemia or myeloblastic leukemia), lymphoma, multiple myeloma, breast cancer, prostate cancer, sarcoma, hepatocellular carcinoma, Hodgkin's lymphoma, T- and B-cell acute lymphoblastic leukemia, small cell lung cancer, acute myeloblastic leukemia, refractory non-Hodgkin's B-cell lymphoma, follicular lymphoma, marginal zone B-cell lymphoma, diffuse large B-cell lymphoma, pancreatic cancer, ovarian cancer, and higher-risk myelodysplastic syndrome.

In one aspect, the present invention relates to a method for treating a disease or disorder mediated by PD-L1 and CD47, comprising administering to the subject in need of such treatment any of the above antibodies, or the pharmaceutical composition of the present invention to a subject in need of such treatment, in a therapeutically effective amount.

In some embodiments of the method for treatment according to the present invention, where the adisease or disorder is selected from the group of (HNSCC) head and neck squamous cell carcinoma, cervical cancer, cancer of unknown primary, glioblastoma, esophageal cancer, bladder cancer, TNBC (triple-negative breast cancer), CRC (colorectal cancer), hepatocellular carcinoma, melanoma, NSCLC (non-small cell lung cancer), kidney cancer, ovarian cancer, MSI CRC (colorectal cancer with with microsatellite instability), leukemia (acute leukemia or myeloblastic leukemia), lymphoma, multiple myeloma, breast cancer, prostate cancer, bladder cancer, sarcoma, hepatocellular carcinoma, glioblastoma, Hodgkin's lymphoma, T- and B-cell acute lymphoblastic leukemia, small cell lung cancer, acute myeloblastic leukemia, refractory non-Hodgkin's B-cell lymphoma, follicular lymphoma, marginal zone B-cell lymphoma, diffuse large B-cell lymphoma, pancreatic cancer, ovarian cancer, and higher-risk myelodysplastic syndrome.

In one aspect, the present invention relates to a method for inhibiting the biological activity of PD-L1 and/or CD47 in a subject in need of such inhibition, which comprises administering an effective amount of any of the above antibodies.

In one aspect, the present invention relates to the use of any of the above antibodies or the above pharmaceutical composition for treatment of a subject in need of such treatment, of a disease or disorder mediated by PD-L1 and CD47.

In some embodiments of the use of an antibody according to the present invention, a disease or disorder is selected from the group of (HNSCC) head and neck squamous cell carcinoma, cervical cancer, cancer of unknown primary, glioblastoma, esophageal cancer, bladder cancer, TNBC (triple-negative breast cancer), CRC (colorectal cancer), hepatocellular carcinoma, melanoma, NSCLC (non-small cell lung cancer), kidney cancer, ovarian cancer, MSI CRC (colorectal cancer with with microsatellite instability), leukemia (acute leukemia or myeloblastic leukemia), lymphoma, multiple myeloma, breast cancer, prostate cancer, bladder cancer, sarcoma, hepatocellular carcinoma, glioblastoma, Hodgkin's lymphoma, T- and B-cell acute lymphoblastic leukemia, small cell lung cancer, acute myeloblastic leukemia, refractory non-Hodgkin's B-cell lymphoma, follicular lymphoma, marginal zone B-cell lymphoma, diffuse large B-cell lymphoma, pancreatic cancer, ovarian cancer, and higher-risk myelodysplastic syndrome.

BRIEF DESCRIPTION OF DRAWINGS

FIG. 5. Diagram of ELISA of polyclonal phage carrying VHH antibody fragments specifically interacting with human CD47 antigen.

FIG. 6. Schematic representation of the domain structure of anti-PD-L1/anti-CD47 bispecific antibodies, where A is based on anti-CD47 scFv fragments and B on anti-CD47 VHH fragments. At the same time, the PD-L1 binding part is represented by the Fab fragment.

DISCLOSURE OF THE INVENTION

Definitions and General Methods

Figure 1:
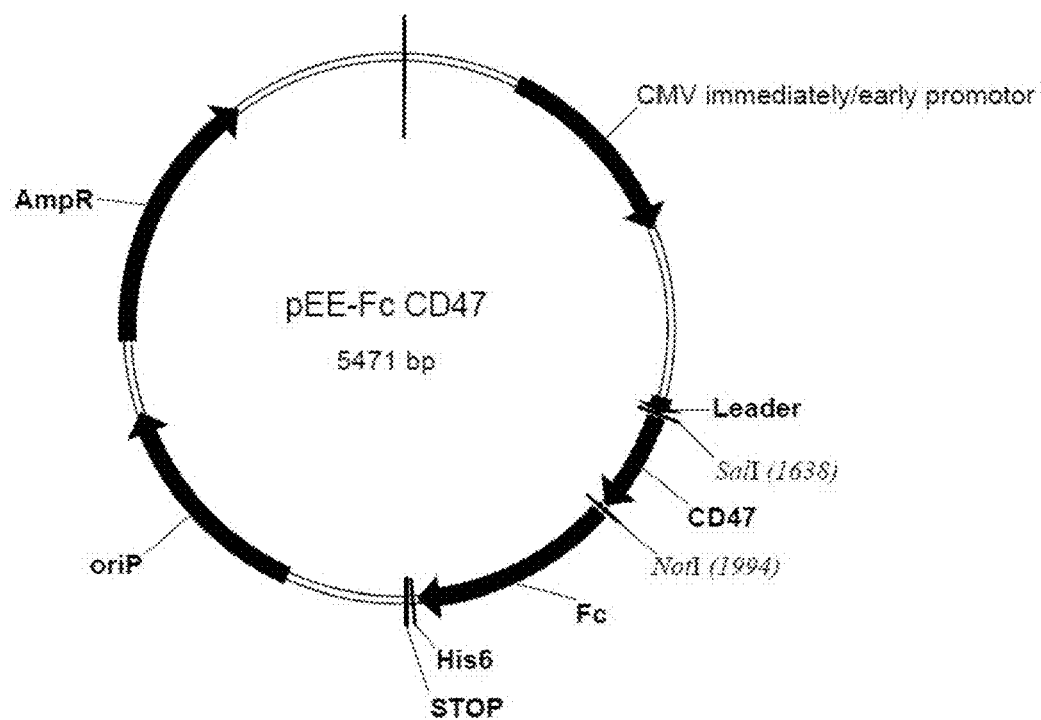
FIG. 1. Plasmid map for transient production of human CD47-Fc in CHO—K1 culture of mammalian cell.

Unless otherwise defined herein, scientific and technical terms used in connection with the present invention will have the meanings commonly understood by those skilled in the art.

Further, unless otherwise required by context, singular terms shall include pluralities and plural terms shall include the singular. Typically, the classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's instructions, as is common in the art, or as described herein.

Definitions Related to Antibody

PD-L1 (Programmed death-ligand 1) also known as cluster of differentiation 274 (CD274) or B7 homolog 1 (B7-H1) is a 40 kDa type 1 transmembrane protein. PD-L1 consists of 3 domains as follows: extracellular domain, represented by Ig V- and C-type domains (220), transmembrane domain (21) and intracellular domain (31). It plays an important role in suppressing the immune system during pregnancy, during the transplantation of foreign tissue, and in certain diseases, such as hepatitis. Under normal conditions, in response to self-antigens, a certain amount of antigen-specific CD8+ T effector cells accumulates in the lymph nodes and spleen, in order to prevent an autoimmune process, PD-1/PD-L1 or B7-1/PD-L1 complexes are formed, resulting in the transmission of an inhibitory signal reducing the proliferation of these CD8+ T cells in the lymph nodes. Thus, PD-1/PD-L interaction is one of the key factors in the development of immune tolerance.

CD47, is a multi-spanning transmembrane receptor belonging to the immunoglobulin superfamily, interacts with SIRPα (signal regulatory protein a) on macrophages thereby suppressing phagocytosis. Cancer cells, in which this pathway is active, avoid phagocytosis. Therefore, a therapeutic effect on CD47 is widely used in various cancers. Antibodies to CD47 may have the ability to block the interaction between CD47 and SIRPα, but they may not have this ability.

The term "binding molecule" includes antibodies and immunoglobulins.

The term "antibody" or "immunoglobulin" or "monoclonal antibody" or "bispecific antibody" or "multispecific antibody" (Ig), as used herein, includes a whole/full-length antibody and any antigen binding fragment (i.e., "antigen-binding portion"). Furthermore, for example, the terms "antibody" or "immunoglobulin" or "monoclonal antibody" include any combination of antigen-binding fragments, having one or more valencies and one or more specificities, and constant regions of immunoglobulins, and may have an analogous meaning to the terms "bispecific antibody" or "multispecific antibody". Furthermore, for example, the terms "antibody" or "immunoglobulin" or "monoclonal antibody" include any combination of antigen-binding fragments and constant regions of immunoglobulins, covalently or noncovalently bound to any polypeptide of any nature. Furthermore, the term "antibody", for example, refers to a glycoprotein comprising at least two heavy (H) chains and two light (L) chains interconnected by disulfide bonds, or an antigen-binding portion. Each heavy chain comprises a heavy chain variable region (abbreviated referred to herein as VH) and the constant region of the heavy chain. Known are five types of mammalian Ig heavy chain denoted by Greek letters: α, δ, ε, γ and μ. The type of a heavy chain present defines the class of an antibody; these chains are found in IgA, IgD, IgE, IgG, and IgM antibodies, respectively. Different heavy chains vary in size and composition; α and γ contain approximately 450 amino acids, while μ and ε consist approximately 550 amino acids. Each heavy chain contains two regions, i.e. constant region and the variable region. The constant region is identical in all antibodies of the same isotype but differs in antibodies of different isotypes. The heavy chains γ, α and δ contain a constant region composed of three constant domains CH1, CH2 and CH3 (in a line), and a hinge region for added flexibility (Woof J., Burton D., Nat. Rev. Immunol. 4, 2004, cc.89-99); heavy chains μ and ε have a constant region composed of four constant domains CH1, CH2, CH3 and CH4. In mammals, known are only two types of light chain denoted by lambda (λ) and kappa (κ). Each light chain consists of a light chain variable region (abbreviated referred to herein as VL) and constant region of the light chain. The approximate length of a light chain is 211 to 217 amino acids. Preferably the light chain is a kappa (κ) light chain, and the constant domain CL is preferably a C kappa (κ).

"Antibodies" according to the invention can be of any class (e.g., IgA, IgD, IgE, IgG, and IgM, preferably IgG), or subclass (e.g., IgG1, IgG2, IgG3, IgG4, IgA1 and IgA2, preferably IgG1).

The VL and VH regions can be further subdivided into hyper-variability regions called complementarity determining regions (CDRs), interspersed between regions that are more conserved, termed framework regions (FR). Each VH and VL is composed of three CDR and four FRs, located from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding portion" of an antibody or "antigen-binding fragment" (or simply "antibody portion" or "antibody fragment"), as used herein, refers to one or more fragments of an antibody that retain the ability to specifically bind to an antigen. It has been shown that the antigen-binding function of an antibody can be performed by fragments of a full length antibody Examples of binding fragments included within the term "antigen-binding portion" of an antibody include (i) Fab-fragment monovalent fragment consisting of the VL, VH, CL and CH 1 domains; (ii) F(ab') 2 fragment, a bivalent fragment comprising two Fab-fragments linked by a disulfide bridge at the hinge region; (iii) Fd-fragment consisting of the VH and CH1 domains; (iv) Fv-fragment consisting of the VL and VH domains of a single arm of an antibody; (v) dAb-fragment (Ward et al., (1989) Nature 341:544-546), which consists of a VH/VHH domain; and (vi) extracted complementarity determining region (CDR). In addition, two regions of the Fv-fragment, VL and VH, are encoded by different genes, they can be joined using recombinant methods using a synthetic linker that enables them to receive a single protein chain in which the VL and VH region are paired to form monovalent molecules (known as single chain Fv (scFv); see e.g., Bird et al. (1988) Science 242:423-426; 14 Huston et al. (1988) Proc. Natl. Acad. Sci. USA 85:5879-5883). It is assumed that such single-stranded molecules are also included within the term "antigen-binding portion" of an antibody. Such antibody fragments are obtained using conventional methods known to those skilled in the art, and these fragments are screened in the same manner as are intact antibodies.

Preferably, the CDR of antigen-binding region or the whole antibody antigen binding region of the invention is derived from mouse, lama or human donor library or is essentially human in origin with certain amino acid residues altered, e.g., substituted with different amino acid residues in order to optimize the properties of the specific antibodies, e.g., KD, koff, IC50, EC50, ED50. Preferably the framework regions of antibodies of the invention are of human origin or substantially of human origin (at least 80, 85, 90, 95, 96, 97, 98 or 99% of human origin).

In other embodiments, the antigen binding portion of the invention may be derived from other non-human species including mouse, lama, rabbit, rat or hamster, but not limited to. Alternatively, the antigen-binding region can be derived from the human species.

The term "variable domain" refers to the fact that certain regions of the variable domains greatly differ in sequence among antibodies. The V domain mediates antigen binding and determines specificity of a particular antibody for its particular antigen. However, the variability is unevenly distributed on the site of the variable domains of 110 amino acids. Instead, the V regions consist of invariant fragments called framework regions (FRs) of 15-30 amino acids separated by shorter regions of extreme variability called "hypervariable regions" or CDRs. Each variable domains of native heavy and light chains each comprise four FRs, mainly taking a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of the antibodies. The constant domains are not directly involved in binding an antibody to an antigen, but exhibit various effector functions, such as participation of the antibody in the antibody-dependent cellular cytotoxicity (ADCC).

The term "hypervariable region" as used herein refers to the amino acid residues of an antibody which are responsible for antigen binding. The hypervariable region generally comprises amino acid residues from a "complementarity determining region" or "CDR" and/or those residues from a "hypervariable loop".

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., Proc. Natl. Acad. Sci. USA, 94:412-417 (1997) and the step-by-step in vitro affinity maturation proposed by Wu et al., Proc. Natl. Acad. Sci. USA 95:6037 6042 (1998).

"Framework regions" (FR) are residues of the variable domain that are different from the CDR residues. Each variable domain typically has four FRs identified as FR1, FR2, FR3 and FR4. If the CDRs are defined according to Kabat, the FR light chain residues are localized approximately at residues 1-23 (LCFR1), 35-49 (LCFR2), 57-88 (LCFR3), and 98-107 (LCFR4) and the FR residues of the heavy chain are localized approximately in the region of residues 1-30 (HCFR1), 36-49 (HCFR2), 66-94 (HCFR3), and 103-113 (HCFR4) in the heavy chain. If the CDRs comprise amino acid residues from hypervariable loops, the FR light chain residues are localized approximately at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the he FR1 residues of the heavy chain are at positions 1-25 and the FR2 residues are at positions 36-49.

The antibody of this invention, "which binds" the target antigen, is an antibody that binds the antigen with sufficient affinity so that the antibody can be used as a diagnostic and/or therapeutic agent when targeting a protein or cell, or tissue expressing an antigen, and slightly cross-reacts with other proteins. According to analytical methods: fluorescence-activated cell sorting (FACS), radioimmunoassay (RIA) or ELISA, in such embodiments, the degree of antibody binding to a non-target protein is less than 10% of antibody binding to a specific target protein. With regard to the binding of an antibody to a target molecule, the term "specific binding" or "specifically binds to" or is "specific for" a particular polypeptide or an epitope on a particular polypeptide target means binding that is noticeably (measurably) different from a non-specific interaction (for example, in the case of bH1-44 or bH1-81, a non-specific interaction is binding to bovine serum albumin, casein, fetal bovine serum or neutravidin).

Specific binding can be measured, for example, by determining the binding of the molecule compared to the binding of the control molecule. For example, specific binding can be determined by competition with another molecule similar to the target, for example, with an excess of unlabeled target. In this case, thw specific binding is indicated if the binding of the labeled target to the probe is competitively inhibited by excess unlabeled target. As used herein, the term "specific binding" or "specifically binds to" or is "specific for" a particular polypeptide or an epitope on a particular polypeptide target can be characterized by a molecule having a Kd for the target of at least about 200 nM, or at least about 150 nM, or at least about 100 nM, or at least about 60 nM, or at least about 50 nM, or at least about 40 nM, or at least about 30 nM, or at least about 20 nM, or at least about 10 nM, or at least about 8 nM, or at least about 6 nM, or at least about 4 nM, or at least about 2 nM, or at least about 1 nM, or greater. In one embodiment, the term "specific binding" refers to binding where a molecule binds to a particular polypeptide or epitope on a particular polypeptide without substantially binding to any other polypeptide or epitope on a polypeptide.

The term "Ka", as used herein, refers to the association rate of a particular antibody-antigen interaction, while the term "Kd" is intended to refer to the dissociation rate of a particular antibody-antigen interaction.

"Binding affinity" generally refers to the strength of the cumulative non-covalent interactions between a single binding site of a molecule (e.g., an antibody) and its binding partner (e.g., an antigen). Unless indicated otherwise, "binding affinity" refers to intrinsic (characteristic, true) binding affinity which reflects a 1:1 interaction between members of a binding pair (e.g., antibody and antigen). The affinity of the molecule X for its binding partner Y can usually be represented by the dissociation constant (Kd). Preferably, the Kd value is approximately 200 nM, 150 nM, 100 nM, 60 nM, 50 nM, 40 nM, 30 nM, 20 nM, 10 nM, 8 nM, 6 nM, 4 nM, 2 nM, 1 nM, or less. Affinity can be measured by common methods known in the art, including those described herein. Low-affinity antibodies generally bind an antigen slowly and tend to dissociate readily, whereas high-affinity antibodies generally bind an antigen faster and tend to remain bound longer. A variety of methods of measuring binding affinity are known in the art, any of these methods can be used for purposes of the present invention.

In one embodiment of the invention, the "Kd" or "Kd value" is measured by surface plasmon resonance assays using BIAcore™-2000 or BIAcore®-3000 (BIAcore, Inc., Piscataway, N.J.) at 25° C. with immobilized chips CM5 antigen at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. The antigen is diluted with 10 mM sodium acetate, pH 4.8, to a concentration of 5 µg/ml (~0.2 µM) and then injected at a flow rate of 5 µl/minute to achieve approximately 10 relative units (RU) of the bound protein. After administration of the antigen, a 1M ethanolamine solution is injected to block unreacted groups. For kinetics measurements, double serial dilutions of Fab (e.g., from 0.78 nM to 500 nM) are injected in PBS with 0.05% Tween™ 20 (PBST) at 25° C. at a flow rate of approximately 25 µl/min. On-rates (kon) and off-rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol. Biol. 293: 865-881. If, according to the above surface plasmon resonance method, the association rate exceeds $10^6$ $M^{-1}$ $s^{-1}$, then it can be determined by fluorescence quenching, which measures the increase or decrease in the intensity of fluorescence emission (excitation=295 nm; emission (radiation)=340 nm, 16 nm band) at 25° C. Antibody antigen solution (Fab form) with a concentration of 20 nM in PBS, pH 7.2, in the presence of increasing concentrations of antigen measured using a spectrometer, such as a stopped flow spectrophotometer (Aviv Instruments) or spectrometer SLM-Aminco (Thermo Spectronie) Series 8000 with a cuvette with stirring.

The term "koff" refers to the dissociation rate constant of a particular interaction of a binding molecule and an antigen. The koff dissociation rate constant can be measured by biolayer interferometry, for example, using the Octet™ system The "association rate" ("on-rate") or "kon" according to the present invention can be also measured by using the above surface plasmon resonance assays using BIAcore™-2000 or BIAcore®-3000 (BIAcore, Inc., Piscataway, N.J.) at 25° C., using chips with immobilized CM5 antigen at ~10 relative units (response units, RU)). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. The antigen is diluted with 10 mM sodium acetate, pH 4.8, to a concentration of 5 µg/ml (~0.2 µM) and then injected at a flow rate of 5 µl/minute to achieve approximately 10 relative units (RU) bound protein. After administration of the antigen, a 1 M ethanolamine solution is injected to block unreacted groups.

Unless specified otherwise, the term "biologically active" and "biological activity" and "biological characteristics" in relation to the polypeptide of the present invention means having the ability to bind to a biological molecule.

The expression "biological molecule" refers to a nucleic acid, a protein, a carbohydrate, a lipid, and combinations thereof. In one embodiment of the invention, the biological molecule exists in nature.

Antibody fragments, such as Fab and F(ab')2 fragments, can be obtained from whole antibodies using conventional methods, such as papain or pepsin hydrolysis of whole antibodies. Moreover, antibodies, parts of antibodies and immunoadhesion molecules can be obtained using standard recombinant DNA methods, for example, as described herein.

The term "recombinant antibody" is intended to refer to an antibody that is expressed in a cell or cell line comprising a nucleotide sequence(s) encoding antibodies, wherein said nucleotide sequence(s) is not naturally associated with the cell.

The term "variant antibody", as used herein, refers to an antibody having an amino acid sequence that differs from the amino acid sequence of its "parental" antibody thereof by virtue of adding, deleting and/or substituting one or more amino acid residues as compared to the sequence of a parental antibody. In a preferred embodiment of the invention, the variant antibody comprises at least one or more (e.g., one to twelve, e.g., two, three, four, five, six, seven, eight or nine, ten, eleven or twelve; in some embodiments, a variant antibody comprises from one to about ten) additions, deletions, and/or substitutions of amino acids as compared to a parental antibody. In some embodiments, such additions, deletions and/or substitutions are made in the CDRs of a variant antibody. Identity or homology with respect to the sequence of a variant antibody is defined herein as the percentage of amino acid residues in the variant antibody sequence that are identical to those of the parental antibody, after aligning the sequences and introducing gaps, if necessary, to achieve the maximum percent of sequence identity. A variant antibody retains the ability to bind to the same antigen, and preferably to an epytope, to which the parental antibody binds; and in some embodiments, at least one property or biological activity are superior to those of a parental antibody. For example, a variant antibody may have, e.g., a a more pronounced binding affinity, longer half-life, lower IC50, or enhanced ability to inhibit antigen biological activity as compared to the parental antibody. Of particular interest in this document is a variant antibody showing a biological activity greater than at least 2 times (preferably at least 5 times, 10 times or 20 times) the biological activity of the parent antibody.

The term "bispecific antibody" means an antibody contining an antigen-binding domain(s) that are capable of specific binding with two different epitopes on one biological molecule or capable of specific binding with epitopes on two different biological molecules. The bispecific antibody is also referred to herein as having "dual specificity" or as being a "dual specificity" antibody.

In a broad sense, the term "chimeric antibody" refers to an antibody that comprises one or more regions of one antibody, and one or more regions of one or several other antibodies, typically, a partially human and partially non-human antibody, i.e. derived partially from a non-human animal, such as mice, rats, or the like vermin, or the Camelidae such as llama and alpaca. Chimeric antibodies are generally preferred over non-human antibodies in order to reduce the risk of a human anti-antibody immune response, e.g. a human anti-mouse antibody immune response in the case of a murine antibody. An example of a typical chimeric antibody is that in which the variable region sequences are murine sequences, while the constant region sequences are human. In the case of a chimeric antibody, the non-human parts may be further modified to humanize the antibody.

The term "humanization" refers to the fact that when an antibody has a fully or partially non-human origin, for example, a mouse or llma antibody obtained by immunizing mice or lamas, respectively, with an antigen of interest, or is a chimeric antibody based on such an antibody of a mouse or llama, it is possible to substitute certain amino acids, in particular in the framework regions and constant domains of heavy and light chains, in order to avoid or minimize the immune response in humans. The specificity of the antibodies interaction with target antigens predominantly through amino acid residues that are located in the six heavy and light chain CDRs. For this reason, amino acid sequences within CDRs are far more variable between individual antibodies than those outside of CDRs. Since the CDR sequences of the sites are responsible for the majority of antibody-antigen interactions, recombinant antibodies can be expressed that mimic the properties of a specific natural antibody, or more generally, a specific antibody with a given amino acid sequence, for example, by constructing expression vectors that express CDR sequences—plots of specific antibodies and framework sequences of another antibody. As a result, it is possible to "humanize" a non-human antibody and, to a large extent, preserve binding specificity and affinity of the initial antibody. Although it is not possible to accurately predict the immunogenicity and thereby the human anti-antibody response of a particular antibody, non-human antibodies are typically more immunogenic than human antibodies. Chimeric antibodies, where the foreign (e.g. vermin or Camelidae) constant regions have been substituted with sequences of human origin showed a generally lower immunogenicity than antibodies of completely foreign origin, and there is a tendency to use humanized or fully human antibodies in therapeutic antibodies. Therefore, chimeric antibodies or other antibodies of non-human origin can be humanized to reduce the risk of a human anti-antibody response.

For chimeric antibodies, humanization typically involves modification of the framework regions of variable region sequences. Amino acid residues that are part of complementarity determining regions (CDRs) will be most often not modified by virtue of humanization, although in some cases it may be desirable in order to modify individual amino acid residues of a CDR, for example, in order to remove a glycosylation site, a deamidation site, an aspartate isomerization site, or undesired cysteine or methionine residues. N-linked glycosylation occurs by attaching an oligosaccharide chain to an asparagine residue in the tripeptide sequence Asn-X-Ser or Asn-X-Thr, where X can be any amino acid other than Pro. Removal of an N-glycosylation site may be achieved by mutating either the Asn or Ser/Thr residue with another residue, preferably by conservative substitution. Deamidation of asparagine and glutamine residues can occur depending on such factors as pH and surface exposure. Asparagine residues are particularly susceptible to deamidation, especially if they are present in the Asn-Gly sequence, and to a lesser extent in other dipeptide sequences, such as Asn-Ala. In the presence of such a deamidated region, for example, Asn-Gly in the sequence of a CDR region, it may be preferable to remove this region, as a rule, by a conservative replacement to remove one of the residues involved.

Numerous methods for humanization of an antibody sequence are known in the art. One commonly used method is CDR site transplantation. CDR grafting may be based on Kabat CDR definitions, althogh the last edition (Magdelaine-Beuzelin et al., Crit. Rev. Oncol. Hematol. 64:210 225 (2007)) suggests that the IMGT® (the international ImMunoGeneTics information system®, www.imgt.org) definition may improve humanization results (see Lefranc et al., Dev. Comp. Immunol. 27:55-77 (2003)). In some cases, CDR grafting may reduce the binding specificity and affinity, and thus the biological activity, of a CDR grafted non-human antibody, as compared to a parental antibody from which the CDRs were obtained. Reverse mutations (which are sometimes referred to as "framework region repair" can be used in selected positions of a CDR grafted antibody, typically in framework regions, in order to restore the binding specificity and affinity of a parental antibody. Determenation of positions for possible reverse mutations can be performed using information available in the literature and in antibody databases. Amino acid residues that are candidates for reverse mutations are usually located on the surface of an antibody molecule, whereas residues that are buried or that have a low degree of surface exposure will not normally be altered. The humanization method, alternative to CDR-site transplantation and reverse mutation, is a surface change in which non-exposed remains of non-human origin are preserved, while remains exposed on the surface change to human remains.

There are two technologies for producing fully human antibodies: using in vitro collected phage libraries or in vivo by immunizing humanized animals (mice, rats, etc.).

Phage display is the first and most widely used in vitro antibody search technology. In 1985, Smith found that foreign DNA sequences could be cloned into filamentous bacteriophage M13 and that such cloned sequence can be expressed on the surface of phage particles as fusion proteins (Smith G P: Filamentous fusion phage: novel expression vectors that display cloned antigens on the virion surface. Science 1985, 228:1315-1317.). Thus, it is possible to select the fusion proteins of interest based on their ability to bind other proteins. This discovery was combined with PCR amplification methods, which made it possible to clone the cDNA repertoire of immunoglobulin genes to create a variety of phage libraries containing variable domains that can be used to quickly search for target-specific monoclonal antibodies. Phage library repertoire reflects repertoire of B-cell antibody of each person or animal whose blood was used to create the library. In 1995, two articles reported the creation of genetically engineered mice that expressed fully human antibody repertoires that could be comparable to those produced by the hybridoma technology (Lonberg N, Taylor L D, Harding F A, Trounstine M, Higgins K M, Schramm S R, Kuo C C, Mashayekh R, Wymore K, McCabe J G et al.: Antigen-specific human antibodies from mice comprising four distinct genetic modifications. Nature 1994, 368:856-859). In these animals, their own endogenous heavy and k light immunoglobulin chain genes were deliberately destroyed, followed by introduction of transgenes, which are the segments of human heavy and k light chain genes. It turned out that human gene repertoire can be used by the mouse immune system to produce high specificity and high affinity antibodies against a greater variety of antigens. Althought transgenic mice express B-cell receptors that are essentially hybrids of mouse and human components (human immunoglobulin, mouse Iga, Ig(3, and other signaling molecules), their B-cells develop and mature normally.

In certain cases, it may also be preferable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., Proc. Natl. Acad. Sci. USA, 94:412-417 (1997) and the stepwise in vitro affinity maturation method by Wu et al., Proc. Natl. Acad. Sci. USA 95:6037 6042 (1998).

The term "monoclonal antibody" or "mAb" refers to an antibody that is synthesized and isolated by a separate clonal population of cells. The clonal population can be a clonal population of immortalized cells. In some embodiments, the immortalized cells in a clonal population are hybrid cells-hybridomas—typically produced by the fusion of individual B lymphocytes from immunized animals with individual cells from a lymphocytic tumour. Hybridomas are a type of constructed cells and do not exist in nature.

"Native antibodies" are usually heterotetrameric glycoproteins with a molecular weight of approximately 150,000 daltons, consisting of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Specific amino acid residues are believed to form an interface between the light chain and heavy chain variable domains.

The term "isolated" used to describe the various antibodies in this description refers to an antibody which has been identified and separated and/or regenerated from a cell or cell culture, in which the antibody is expressed. Impurities (contaminant components) from the natural environment are materials which would interfere with diagnostic or therapeutic uses of the polypeptide, and may include enzymes, hormones, and other proteinaceous or non-proteinaceous solutes. In preferred embodiments, the antibody is purified (1) to a degree sufficient to obtain at least 15 residues of N-terminal or internal amino acid sequence by use of a spinning cup sequenator (Edman sequenator), or (2) to homogeneity by SDS-PAGE under nonreducing or reducing conditions using Coomassie Brilliant Blue, or preferably silver stain. Isolated antibody includes the antibody in situ within recombinant cells since at least one component of the polypeptide's natural environment will not be present. Isolated polypeptide is typically obtained by at least one purification step.

An "isolated" nucleic acid molecule is one which is identified and separated from at least one nucleic acid molecule-impurity, which the former is bound to in the natural source of antibody nucleic acid. An isolated nucleic acid molecule is different from the form or set in which it is found under natural conditions. Thus, the isolated nucleic acid molecule is different from a nucleic acid molecule that exists in cells under natural conditions. However, an isolated nucleic acid molecule however includes a nucleic acid molecule located in cells in which the antibody is normally expressed, for example, if the nucleic acid molecule has a chromosomal localization that is different from its localization in cells under natural conditions.

The term "epitope" as used herein refers to a portion (determinant) of an antigen that specifically binds to a binding molecule (for example, an antibody or a related molecule, such as a bispecific binding molecule). Epitope determinants usually consist of chemically active surface groupings of molecules such as amino acids or carbohydrates or sugar side chains and tipically comprise specific three dimensional structural characteristics, as well as specific charge characteristics. The epitope can be either "linear" or "conformational". In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. When the desired epitope of an antigen is determined, antibodies to this epitope can be generated using techniques well known in the art. In addition, the generation and characterization of antibodies or other binding molecules may elucidate information about desirable epitopes. Based on this information, you can then competitively screen binding molecules to bind to the same or similar epitopes, for example, by conducting competition studies to find binding molecules that compete for binding to an antigen.

The term "peptide linker" as used herein is intended to mean any peptide having the ability to connect domains, with a length depending on the domains which it binds to each other and comprising any amino acid sequence. Preferably, the peptide linker has a length of more than 5 amino acids and consists of any set of amino acids selected from G, A, S, P, E, T, D, K.

The term "in vitro" refers to a biological object, a biological process, or a biological reaction outside the body, modeled in artificial conditions. For example, a cell grown in vitro is to be understood as a cell grown in an environment outside the body, e.g., in a test tube, a culture vial, or a microtiter plate.

The term "IC$_{50}$" (inhibitory concentration 50%) refers to drug concentrations, at which a measurable activity or response, for example, growth/proliferation of cells such as tumor cells, is inhibited by 50%. The IC$_{50}$ value can be calculated using appropriate dose-response curves, using special statistical software for curve fitting.

The term GI 50 (growth inhibition 50%) refers to drug concentrations, at which proliferation of cells, such as tumor cells, is inhibited by 50%.

The term "ED50" (EC50) (50% effective dose/concentration) refers to drug concentration to produce a 50% biological effect (which may include cytoxicity).

The term antibody "effector function" refers to biological activities attributable to the Fc-region (native Fc-region sequence or Fc-region amino acid variants) of an antibody or vary with the antibody isotype. Examples of antibody effector functions include: Cl$_q$ binding and complement dependent cytotoxicity; Fc receptor binding; antibody-dependent cell-mediated cytotoxicity (ADCC); phagocytosis; down regulation of cell surface receptors (e.g., B-cell receptor, BCR), and B-cell activation.

"Antibody-dependent cellular cytotoxicity" or "ADCC" refers to a cell-mediated response, in which non-specific cytotoxic cells that express Fc receptors (FcR) (for example, natural killer (NK) cells, neutrophils, and macrophages) recognize bound antibody on a target cell and subsequently cause lysisof the target cell. The primary cells for mediating ADCC, NK cells, express FcγRJII only, whereas monocytes express FcγRI, FcγRII and FcγRIII. FcR expression on hematopoietic cells is summarized in Table 3 on page 464 of Ravetch and Kinet, Annu. Rev. Immunol 9: 457-92 (1991). To assess ADCC activity of a molecule of interest, an in vitro ADCC assay, such as that described in U.S. Pat. Nos. 5,500,362 or 5,821,337 may be performed. Applicable effector cells for such assays include peripheral blood mononuclear cells (PBMC) and natural killer (NK) cells. Alternatively, or additionally, the ADCC activity of the molecule of interest may be assessed in vivo, e.g., in an animal model such as that disclosed in Clynes et al. PNAS (USA) 95: 652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII (FcγRIIa and FcγRIIb), and FcγRIII (FcγRIIIa и FcγRIIIb) subclasses, including allelic variants and alternatively spliced forms of these receptors. FcγRI exhibits high affinity to IgG, whereas FcγRII and FcγRIII exhibit low affinities. FcγRIIa and FcγRIIIa are activating FcγRs that are expressed on monocytes/macrophages and monocytes/macrophages/natural killer cells, respectively, and are capable of triggering cytotoxicity of human target cells. The activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daëron, Annu. Rev. Immunol. 15: 203-234 (1997)). FcRs are reviewed in Ravetch and Kinet, Annu. Rev. Immunol 9: 457-92 (1991). Other FcRs, including those to be identified in the future, are encompassed by the term "FcR" herein. The term also includes the neonatal receptor, FcRn, which is responsible for the transfer of maternal IgGs to the fetus.

"Complement-dependent cytotoxicity" or "CDC" refers to the ability of a molecule to lyse a target in the presence of complement. The complement activation pathway is initiated by the binding of the first component of the complement system (Clq) to a molecule (e.g., an antibody) complexed with a cognate antigen. To assess complement activation, a CDC assay, e.g., as described in Gazzano-Santoro et al., J. Immunol. Methods 202: 163 (1996) may be performed.

The term "identity" or "homology" is construed to mean the percentage of amino acid residues in the candidate sequence that are identical to the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, WI 53705). This software matches similar sequences by assigning a degree of homology to various substitutions, deletions (eliminations), and other modifications.

The term "homologous" with regard to a polypeptide sequence of an antibody should be construed as an antibody exhibiting at least 70%, preferably 80%, more preferably 90% and most preferably 95% sequence identity relative to a polypeptide sequence. The term in relation to a nucleic acid sequence should be construed as a sequence of nucleotides exhibiting at least 85%, preferably 90%, more preferably 95% and most preferably 97% sequence identity relative to a nucleic acid sequence.

The proposed modification (s) of the amino acid sequences of the antibodies described in this publication. For example, it may be desirable to improve the binding affinity and/or other biological properties of the antibody. Amino acid sequence variants of antibody are prepared by introducing appropriate nucleotide changes into the antibody nucleic acid, or by peptide synthesis. Such modifications include, for example, deletions, and/or insertions and/or substitutions of residues within the amino acid sequences of antibody. Any combination of deletion, insertion, and substitution is made to arrive at the final construct, provided that the final construct possesses the desired characteristics. The amino acid changes also may alter post-translational processes in the antibody, such as changing the number or position of glycosylation sites.

A variant of modification of amino acid sequences of antibodies using amino acid substitutions. Such a variant is substitution of at least one amino acid residue in the antibody molecule with a different residue. The sites of greatest interest for substitutional mutagenesis include hypervariable regions or CDRs, but FR or Fc alterations are also contemplated. Conservative substitutions are shown in Table A under "preferred substitutions". If such substitutions lead to a change in biological activity, then additional significant changes may be introduced, called "examples substitution"

in table A, or changes, further described below in describing classes of amino acids, and can be screened products.

TABLE A

| Original residue | Exemplary substitutions | Preferred substitutions |
|---|---|---|
| Ala (A) | Val; Leu; Ile | Val |
| Arg(R) | Lys; Gin; Asn | Lys |
| Asn(N) | Gin; His; Asp, Lys; Arg | Gin |
| Asp (D) | Glu; Asn | Glu |
| Cys (C) | Ser; Ala | Ser |
| Gln(Q) | Asn; Glu | Asn |
| Glu (E) | Asp; Gin | Asp |
| Gly(G) | Ala | Ala |
| His (H) | Asn; Gin; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gin; Asn | Arg |
| Met (M) | Leu; Phe; Ile | Leu |
| Phe(F) | Trp; Leu; Val; Ile; Ala; Tyr | Tyr |
| Pro (P) | Ala | Ala |
| Ser(S) | Thr | Thr |
| Thr (T) | Val; Ser | Ser |
| Trp(W) | Tyr; Phe | Tyr |
| Tyr(Y) | Trp; Phe; Thr; Ser | Phe |
| Val (V) | Ile; Leu; Met; Phe; Ala; Norleucine | Leu |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-strand DNA or RNA, a single-strand DNA or RNA, or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Thus, isolated nucleic acids obtained by recombinant genetics, by means, for example, of host cells, or obtained by chemical synthesis should also be mentioned here.

The reference to the nucleotide sequence covers the complement thereof unless otherwise specified. Thus, a reference to a nucleic acid having a particular sequence should be understood as one which encompasses the complementary strand thereof with the complementary sequence thereof.

The expression "control sequences" refers to DNA sequences necessary for the expression of a functionally related coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, the DNA for a pre-sequence or secretory leader sequence is operably linked to DNA for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

The term "vector" as used herein means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, vectors are capable of autonomous replication in a host cell into which they are introduced (e.g., bacterial vectors having a bacterial origin site of replication and episomal mammalian vectors). In further embodiments, vectors (e.g., non-episomal mammalian vectors) can be integrated into the genome of a host cell upon introduction into a host cell, and thereby are replicated along with the host gene. Moreover, certain vectors are capable of directing the expression of genes to which they are operatively linked. Such vectors are referred to herein as "recombinant expression vectors" (or simply, "expression vectors").

The term "recombinant host cell" (or simply "host cell") as used herein is intended to refer to a cell into which a recombinant expression vector has been introduced. The present invention relates to host cells, which may include, for example, a vector according to the invention described above. The present invention also relates to host cells that comprise, for example, a nucleotide sequence encoding a heavy chain or antigen-binding portions thereof, a light chain-encoding nucleotide sequence or antigen-binding portions thereof, or both, of the first binding domain and/or second binding domain of a binding molecule of the invention. It should be understood that "recombinant host cell" and "host cell" are intended to refer not only to a particular subject cell but to the progeny of such a cell as well. Since modifications may occur in succeeding generations due to either mutation or environmental influences, such progeny may not, in fact, be identical to a parental cell, however, such cells are still included within the scope of the term "host cell" as used herein.

The term "excipient" is used herein to describe any ingredient that is different from the compound (s) of this invention.

"Pharmaceutical composition" refers to a composition comprising an antibody of the present invention and at least one of components selected from the group comprising pharmaceutically acceptable and pharmacologically compatible fillers, solvents, diluents, carriers, auxiliary, distributing and sensing agents, delivery agents, such as preservatives, stabilizers, filler, disintegrators, moisteners, emulsifiers, suspending agents, thickeners, sweeteners, flavouring agents, aromatizing agents, antibacterial agents, fungicides, lubricants, and prolonged delivery controllers, the choice and suitable proportions of which depend on the type and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar and tragacant and their mixtures as well. Protection against action of microorganisms can be provided by various antibacterial and antifungal agents, such as, for example, parabens, chlorobutanole, sorbic acid, and similar compounds. Composition may also contain isotonic agents, such as, for example, sugars, polyols, sodium chloride, and the like. Prolonged action of composition may be achieved by agents slowing down absorption of active ingredient, for example, aluminum monostearate and gelatine. Examples of suitable carriers, solvents, diluents and delivery agents include water, ethanol, polyalcohols and their mixtures, natural oils (such as olive oil) and organic esters (such as ethyl oleate) for injections. Examples of fillers are lactose, milk-sugar, sodium citrate, calcium carbonate, calcium phosphate and the like. Examples of disintegrators and distributors are starch, alginic acid and its salts, silicates. Examples of suitable lubricants are magnesium stearate, sodium lauryl sulfate, talc and polyethylene glycol of high molecular weight. Pharmaceutical composition for peroral, sublingual, transdermal, intraocular, intramuscular, intravenous, subcutaneous, local or rectal administration of active ingredient, alone or in combination with another active compound may be administered to human and animals in a standard administration form, in a mixture with traditional pharmaceutical carriers. Suitable standard administration forms include peroral forms such as tablets, gelatin capsules, pills, powders, granules, chewing-gums and peroral solutions or suspensions; sublingual and transbuccal administration forms; aerosols; implants; local, transdermal, subcutaneous, intramuscular, intravenous, intranasal or intraocular forms and rectal administration forms.

"Medicament"—is a compound (or a mixture of compounds as a pharmaceutical composition) in the form of tablets, capsules, solutions, ointments and other ready forms intended for restoration, improvement or modification of physiological functions in humans and animals, and for treatment and prophylaxis of diseases, for diagnostics, anesthesia, contraception, cosmetology and others.

The term "disease or disorder mediated by CD47 and PD-L1" means all disease or disorder that is either directly, or indirectly associated with CD47 and PD-L1, including etiology, development, progression, persistence or pathology of a disease or disorder. "Treat", "treating" and "treatment" refer to a method of alleviating or abrogating a biological disorder and/or at least one of attendant symptoms thereof. As used herein, to "alleviate" a disease, disorder or condition means reducing the severity and/or occurrence frequency of the symptoms of a disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

The term "disorder" means any condition that would benefit from treatment with the compound of the present invention. The definition of this term includes chronic and acute disorders or diseases, including pathological conditions that cause the predisposition of a mammal to the occurrence of this violation. The preferred disorder to be treated according to the invention is cancer.

The terms "cancer" and "cancerous" refer to a physiological condition or describe a physiological condition in mammals that is typically characterized by unregulated growth/proliferation of cells. The definition encompasses both benign and malignant cancerous diseases. Examples of cancerous diseases include, but are not limited to, carcinoma, lymphoma, blastoma, sarcoma, and leukemia. More particular examples of such cancerous diseases include squamous cell cancer, small-cell lung cancer, non-small cell lung cancer, adenocarcinoma of the lung and squamous carcinoma of the lung, peritoneal cancer, hepatocellular cancer, stomach cancer including gastrointestinal cancer, pancreatic cancer, glioblastoma, glioma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, and various head and neck cancers.

The terms "immune response", "autoimmune response" and "autoimmune inflammation" refer, for example, to the action of lymphocytes, antigen-presenting cells, phagocytic cells, granulocytes and soluble macromolecules produced by said cells or liver cells (including antibodies, cytokines and complement produced in the result of selective damage, destruction or elimination of invasive pathogens, cells or tissues infected with pathogens, cancer cells or, in cases of autoimmunity or pathological inflammation, normal cells or tissues from the human body).

A "therapeutically effective amount" is intended to refer to that amount of the therapeutic agent being administered which will relieve to some extent one or more of the symptoms of the disorder being treated.

The term "chronic" use refers to the continuous (continuous) use of the agent (s) as opposed to the acute (short-term) route of administration, so as to maintain the initial therapeutic effect (activity) for a long period of time.

"Intermittent" use refers to treatment that is not carried out consistently without interruptions, but which is rather periodic in nature.

As used herein, the words "comprise," "have," "include," or variations such as "comprises," "comprising," "has," "having," "includes" or "including", and all grammatical variations thereof will be understood to imply the inclusion of a stated integer or group of integers but not the exclusion of any other integer or group of integers.

DETAILED DESCRIPTION OF THE INVENTION

Antibody

The present invention relates to antibodies that bind to CD47 and PD-L1.

In one embodiment of the present invention, the antibody is a full-length antibody or its antigen-binding fragment thereof.

In one embodiment of the present invention, an antibody of the present invention includes one or two binding sites to PD-L1.

In one embodiment of the present invention, the binding binding site to CD47 inhibits the interaction of the CD47 receptor and SIRPα ligand, and/or binding site to PD-L1 inhibits the interaction of PD-L1 with PD-1 receptor.

In one of the embodiments of the present invention relates to an antibody that binds CD47 and PD-L1, and the binding site to CD47 which includes the variable region of the heavy chain, containing:
  (a) CDR1 comprising an amino acid sequence that is at least 80% or 90% homologous or identical to the sequence selected from the the following group of SEQ ID NOs: 1-4, i.e. CDR1 is a sequence selected from the following group of SEQ ID NOs: 1-4 or a sequence selected from the following group of SEQ ID NOs: 1-4 with 1 or 2 substitutions;
  (b) CDR2 comprising an amino acid sequence that is at least 80%, 84%, 86%, 88%, 92% or 96% homologous or identical to a sequence selected to the sequence selected from the following group of SEQ ID NOs: 6-15, i.e. CDR2 is the sequence of SEQ ID NOs: 6-15 or a sequence selected from the following group of SEQ ID NOs: 6-15 with 1, 2, 3, 4 or 5 substitutions;
(c) CDR3 comprising an amino acid sequence that is at least 80%, 85%, 86% 90%, 93% or 95% homologous or identical to a sequence selected from the the following group of SEQ ID NOs: 17-20, i.e. CDR3 is a sequence selected from the following group of SEQ ID NOs: 17-20 or a sequence selected from the following group of SEQ ID NOs: 17-20 with 1, 2 or 3 substitutions.

In one of the embodiments of the present invention relates to an antibody that binds CD47 and PD-L1, and the binding site to CD47 which includes the variable region of the heavy chain, containing:
(d) CDR1 comprising an amino acid sequence that is an identical to a sequence selected from the following group of SEQ ID NOs: 1-4;
(e) CDR2 comprising an amino acid sequence that is an identical to a sequence selected from the following group of SEQ ID NOs: 6-15;
(f) CDR3 comprising an amino acid sequence that is an identical to a sequence selected from the following group of SEQ ID NOs: 17-20.

In one embodiment, the present invention relates to an antibody that binds CD47 and PD-L1, and comprises a binding site to CD47 comprising:
(a) a heavy chain variable region, comprising:
(i) CDR1 comprising an amino acid sequence that is at least 80% or 90% homologous or identical to a sequence selected from the group of SEQ ID NOs: 1-4, i.e. CDR1 is a sequence selected from the group of SEQ ID NOs: 1-4 or a sequence selected from the group of SEQ ID NOs: 1-4 with 1 or 2 substitutions;
(ii) CDR2 comprising an amino acid sequence that is at least 80%, 84%, 86%, 88%, 92% or 96% homologous or identical to a sequence selected from the group of SEQ ID NOs: 6-15, i.e. CDR2 is the sequence of SEQ ID NOs: 6-15 or a sequence selected from the group of SEQ ID NOs: 6-15 with 1, 2, 3, 4 or 5 substitutions,
(iii) CDR3 comprising an amino acid sequence that is at least 80%, 85%, 86% 90%, 93% or 95% homologous or identical to a sequence selected from the group of SEQ ID NOs: 17-20, i.e. CDR3 is a sequence selected from the group of SEQ ID NOs: 17-20 or a sequence selected from the group of SEQ ID NOs: 17-20 with 1, 2 or 3 substitutions, and
(b) a light chain variable region comprising:
(i) CDR1 comprising an amino acid sequence that is at least 80% or 90% homologous or identical to a sequence selected from the group of SEQ ID NOs: 22-34, i.e. CDR1 is a sequence selected from the group of SEQ ID NOs: 22-34 or a sequence selected from the group of SEQ ID NOs: 22-34 with 1 or 2 substitutions,
(ii) CDR2 comprising an amino acid sequence that is at least 80%, 87% or 94% homologous or identical to a sequence selected from the group of SEQ ID NOs: 36-48, i.e. CDR2 is a sequence selected from the group of SEQ ID NOs: 36-48 or a sequence selected from the group of SEQ ID NOs: 36-48 with 1, 2 or 3 substitutions,
(iii) CDR3 comprising an amino acid sequence that is at least 80% or 90% homologous or identical to a sequence selected from the group of SEQ ID NOs: 50-64, i.e. CDR3 is a sequence selected from the group of SEQ ID NOs: 50-64 or a sequence selected from the group of SEQ ID NOs: 50-64 with 1 or 2 substitutions.

In one embodiment, the present invention relates to an antibody that binds CD47 and PD-L1, and comprises a binding site to CD47 comprising:
(a) the variable region of the heavy chain comprising:
(i) CDR1 comprising an amino acid sequence selected from the group of SEQ ID NOs: 1-4,
(ii) CDR2 comprising an amino acid sequence selected from the group of SEQ ID NOs: 6-15,
(iii) CDR3 comprising an amino acid sequence selected from the group of SEQ ID NOs: 17-20, and
(b) the variable region of the light chain comprising:
(i) CDR1 comprising an amino acid sequence selected from the group of SEQ ID NOs: 22-34,
(ii) CDR2 comprising an amino acid sequence selected from the group of SEQ ID NOs: 36-48,
(iii) CDR3 comprising an amino acid sequence selected from the group of SEQ ID NOs: 50-64.

In one embodiment, the present invention relates to an antibody that binds CD47 and PD-L1, and comprises a binding site for CD47 comprising:
(a) a heavy chain variable region comprising an amino acid sequence that is at least 90%, 91%, 92%, 93%, 94%, 95%, 96%, 97%, 98% or 99% homologous or identical to a sequence selected from the group of SEQ ID NOs: 66-88, and
(b) a light chain variable region comprising an amino acid sequence that is at least 90%, 91%, 92%, 93%, 94%, 95%, 96%, 97%, 98% or 99% homologous or identical to a sequence selected from the group of SEQ ID NOs: 89-106.

In one embodiment, the present invention relates to an antibody that binds CD47 and PD-L1, and comprises a binding site for CD47 comprising:
(a) a heavy chain variable region comprising an amino acid sequence selected from the group of SEQ ID NOs: 66-88, and
(b) a light chain variable region comprising an amino acid sequence selected from the group of SEQ ID NOs: 89-106.

In one embodiment, the present invention relates to an antibody that binds CD47 and PD-L1, and comprises a binding site for PD-L1 comprising:
(a) the variable region of the light chain comprising:
(i) CDR1 comprising an amino acid sequence that is at least 80% homologous or identical to the sequence of SEQ ID NO: 5, i.e. CDR1 is the sequence of SEQ ID NO: 5 or the sequence of SEQ ID NO: 5 with 1 substitution;
(ii) CDR2 comprising an amino acid sequence that is at least 80%, 86%, or 92% homologous or identical to the sequence of SEQ ID NO: 16, i.e. CDR2 is the sequence of SEQ ID NO: 16 or the sequence of SEQ ID NO: 16 with 1, 2 or 3 substitutions; (iii) CDR3 comprising an amino acid sequence that is at least 80% or 90% homologous or identical to the sequence of SEQ ID NO: 21, i.e. CDR3 is the sequence of SEQ ID NO: 21 or the sequence of SEQ ID NO: 21 with 1 or 2 substitutions, and
(b) the variable region of the comprising:
(i) CDR1 comprising an amino acid sequence that is at least 80%, 86%, or 83% homologous or identical to the sequence of SEQ ID NO: 35, i.e. CDR1 is the sequence of SEQ ID NO: 35 or the sequence of SEQ ID NO: 35 with 1, 2 or 3 substitutions;
(ii) CDR2 comprising an amino acid sequence that is at least 80% homologous or identical to the sequence of SEQ ID NO: 49, i.e. CDR2 is the sequence of SEQ ID NO: 49 or the sequence of SEQ ID NO: 49 with 1 substitution; (iii) CDR3 comprising an amino acid sequence that is at least 80% or 90% homologous or identical to the sequence of SEQ ID NO: 65, i.e. CDR3 is the sequence of SEQ ID NO: 65 or the sequence of SEQ ID NO: 65 with 1 or 2 substitutions.

In one embodiment, the present invention relates to an antibody that binds CD47 and PD-L1, and comprises a binding site for PD-L1 comprising:
(a) the variable region of the heavy chain comprising:
  (i) CDR1 comprising the amino acid sequence of SEQ ID NO: 5,
  (ii) CDR2 comprising the amino acid sequence of SEQ ID NO: 16,
  (iii) CDR3 comprising the amino acid sequence of SEQ ID NO: 21, and
(b) the variable region of the light chain comprising:
  (i) CDR1 comprising the amino acid sequence of SEQ ID NO: 35,
  (ii) CDR2 comprising the amino acid sequence of SEQ ID NO: 49,
  (iii) CDR3 comprising the amino acid sequence of SEQ ID NO: 65.

In one embodiment, the present invention relates to an antibody that binds CD47 and PD-L1, and is characterized in that a binding site to CD47 is Fab, scFv, scFab, or isolated VH or VHH mono-domains.

In one embodiment, the present invention relates to an antibody that binds CD47 and PD-L1, and is characterized in that a binding site to PD-L1 is Fab, scFv, scFab, or isolated VH or VHH mono-domains.

In one embodiment, the present invention relates to an antibody that binds CD47 and PD-L1, and is characterized in that it stimulates antibody-dependent cellular cytotoxicity, macrophage-mediated phagocytosis, complement-dependent cytotoxicity, and/or T cell-mediated cytotoxicity towards cells covered with CD47 and/or PD-L1 antigens.

In one embodiment, the present invention relates to an antibody that binds CD47 and PD-L1, and is characterized in that it comprises an Fc fragment with at least one mutation or modification that increases antibody-dependent cell-mediated cytotoxicity (ADCC) and/or complement dependent cytotoxicity (CDC) compared with the same antibody without mutation or modification.

Nucleic Acid Molecules

The present invention also relates to nucleic acid molecules, and sequences encoding an anti-CD47/PD-L1 antibody of the invention described herein. In some embodiments, various nucleic acid molecules encode the first domain and second domain of the amino acid sequence of an anti-CD47/PD-L1 antibody. In some embodiments, wherein a first domain and/or second domain comprises a heavy chain and light chain, different nucleic acids encode a heavy chain, and light chain amino acid sequences. In other embodiments, the same nucleic acid molecule encodes heavy chain and light chain sequences. In certain embodiments, a nucleic acid molecule can encode any combination of amino acid sequences (e.g., heavy and light chain sequences) of first and second domains. In certain embodiment, a nucleic acid molecule can encode the amino acid sequence of a first binding domain and the light chain amino acid sequence of a second binding domain, optionally including any sequence of a peptide linker connecting them. The reference to a nucleotide sequence encompasses the complement thereof unless otherwise indicated. Thus, a reference to the nucleic acid having a specific sequence should be understood as one which encompasses the complementary strand thereof with the complementary sequence thereof. The term "polynucleotide" as used herein means a polymeric form of either nucleotides that are at least 10 bases in length, or ribonucleotides, or deoxyribonucleotides or a modified form of either type of nucleotide. The term includes single and double stranded forms.

In any of the above embodiments, nucleic acid molecules can be isolated.

A nucleic acid molecule of the invention can be isolated from any source that produces an anti-CD47/PD-L1 antibody. In certain embodiments, a nucleic acid molecule of the invention can be synthesized, rather than isolated.

In some embodiments, a nucleic acid molecule of the invention can comprise a nucleotide sequence encoding a VH domain from the first or second domain of an antibody of the invention, joined in-frame to a nucleotide sequence encoding a heavy chain constant domain from any source. Similarly, a nucleic acid molecule of the invention can comprise a nucleotide sequence encoding a VL domain from the first or second region of an antibody of the invention, joined in-frame to a nucleotide sequence encoding a light chain constant domain from any source.

In a further aspect of the present invention, nucleic acid molecules encoding the variable domain of heavy (VH) and/or light (VL) chains of a first or second binding domain may be "converted" throughout the length of antibody genes. In one embodiment, nucleic acid molecules encoding VH or VL domains are converted to antibody genes throughout the length by virtue of insertion into an expression vector already encoding heavy chain constant (CH) or light chain constant (CL) domains, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into antibody genes throughout the length by virtue of linking, e.g., ligating, a nucleic acid molecule encoding VH and/or VL domains to a nucleic acid molecule encoding CH and/or CL domains using standard molecular biological techniques. Nucleic acid molecules encoding heavy and/or light chains throughout the length may then be expressed in a cell into which they have been introduced.

Nucleic acid molecules may be used to express large quantities of recombinant anti-CD47/PD-L1 antibodies. Nucleic acid molecules may also be used to produce human antibodies, humanized antibodies, chimeric antibodies, bispecific antibodies, single chain antibodies, immunoadhesins, diabodies, mutated antibodies and antibody derivatives, as described herein.

Vector

In another aspect, the present invention relates to a vector suitable for the expression of any of nucleotide sequences described herein.

The present invention relates to vectors comprising nucleic acid molecules that encode any of the amino acid sequences of anti-CD47/PD-L1 antibodies or parts thereof (e.g., heavy chain sequences of a first binding domain and/or heavy and/or light chain sequences of a second binding domain), as described herein. The invention further provides vectors comprising nucleic acid molecules encoding fusion proteins, modified antibodies, antibody fragments.

In another embodiment, nucleic acid molecules and vectors may be used to make mutated anti-CD47/PD-L1 antibodies. Antibodies may be mutated in the variable domains of the heavy and/or light chains of a first binding domain and/or heavy and/or light chains of a second binding domain, e.g., to alter a binding property of the antibodies.

For example, a mutation may be made in one or more CDRs to increase or decrease the $K_D$ of antibodies, to increase or decrease $k_{off}$, or to alter the binding specificity of an antibody with respect to FcRn. In another embodiment, one or more mutations are made at an amino acid residue that is known to be changed compared to the germinal line in an antibody corresponding to the first or second binding domain of anti-CD47/PD-L1 antibodies of the invention. Such mutations may be made in the CDR or framework region of a variable domain, or in a constant domain. In a preferred embodiment, mutations are made in a variable domain. In another embodiment, one or more mutations are made at an amino acid residue that is known to be altered compared to the germinal line in the CDR or framework region of a variable domain of an antibody of the invention.

In some embodiments, the anti-CD47/PD-L1 antibodies of the invention are expressed by inserting a DNA partially or fully encoding the sequence of a first or second binding domain (e.g., light and heavy chain sequences where a binding domain comprises light and heavy chain sequences), obtained as described above, in expression vectors such that the genes are operatively linked to necessary expression control sequences, such as transcriptional and translational control sequences. Expression vectors include plasmids, retroviruses, adenoviruses, adeno-associated viruses (AAV), plant viruses, such as cauliflower mosaic virus, tobacco mosaic virus, cosmids, YACs, EBV derived episomes, and the like. DNA molecules may be ligated into a vector such that transcriptional and translational control sequences within the vector serve their intended function of regulating the transcription and translation of the DNA. An expression vector and expression control sequences may be chosen to be compatible with the expression host cell used. DNA molecules partially or fully encoding the sequences of first and second binding domains (for example, heavy and light chain sequences where a binding domain comprises a heavy and light chain sequence) can be introduced into individual vectors. In one embodiment, any combination of said DNA molecules is introduced into the same expression vector. DNA molecules can be introduced into an expression vector by standard methods (e.g., ligation of complementary restriction sites on an antibody gene fragment and vector, or blunt end ligation if no restriction sites are present).

A suitable vector is one that encodes functionally complete human CH or CL immunoglobulin sequences, with appropriate restriction site engineering so that any VH or VL sequence can easily be inserted and expressed, as described above. HC- and LC-encoding genes in such vectors may contain intron sequences that results in enhanced overall antibody protein yields by stabilizing the corresponding mRNA. The intron sequences are flanked by splice donor and splice acceptor sites, which determine where RNA splicing will occur. Location of intron sequences can be either in variable or constant regions of antibody chains, or in both variable and constant regions when multiple introns are used. Polyadenylation and transcription termination may occur at a native chromosomal site downstream of coding regions. The recombinant expression vector can also encode a signal peptide that facilitates secretion of an antibody chain from a host cell. The antibody chain gene may be cloned into a vector such that the signal peptide is linked in-frame to the amino terminus of an immunoglobulin chain. The signal peptide can be an immunoglobulin signal peptide or a heterologous signal peptide (i.e., a signal peptide from a non-immunoglobulin protein).

In addition to chain genes of antibodies, the recombinant vector expression of the invention can carry regulatory sequences that control the expression of chain genes of antibodies in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g., the major late promoter adenovirus (AdMLP)), polyomavirus and strong mammalian promoters such as native immunoglobulin promoter or actin promoter. For further description of viral regulatory elements and sequences thereof, see, e.g., U.S. Pat. Nos. 5,168,062, 4,510,245 and 4,968,615. Methods for expressing binding molecules, such as antibodies in plants, including a description of promoters and vectors, as well as transformation of plants are known in the art. See, e.g., U. S. Pat. No. 6,517,529. Methods for expressing polypeptides in bacterial cells or fungal cells, e.g., yeast cells, are also well known in the art.

In addition to antibody chain genes and regulatory sequences, the recombinant expression vectors of the invention may carry additional sequences, such as sequences that regulate replication of a vector in host cells (e.g., origins of replication) and selectable marker genes. The selectable marker gene facilitates the selection of host cells into which a vector has been introduced (see e.g., U.S. Pat. Nos. 4,399,216, 4,634,665 and 5,179,017). For example, typically the selectable marker gene confers resistance to medicinal agents, such as G418, hygromycin or methotrexate, on a host cell into which a vector has been introduced. For example, selectable marker genes include a dihydrofolate reductase (DHFR) gene (for use in dhfr-host cells during methotrexate selection/amplification), a neo gene (for G418 selection), and a glutamate synthetase gene.

The term "expression control sequence" as used herein is intended to refer to polynucleotide sequences that are necessary to influence the expression and processing of the coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "control sequences" includes at least all components, the presence of which is essential for expression and processing, and can also include additional components whose presence is beneficial, for example, the leading sequences and the sequence of fused cells.

Host Cells

A further aspect of the invention relates to methods for producing antibodies to CD47 and PD-L1 of the invention. One embodiment of the invention relates to a method for producing antibodies as defined herein, comprising introducing/preparing a recombinant host cell capable of expressing antibodies, culturing said host cells under conditions suitable for expression/production of the antibodies, and isolating the obtained antibody. Antibodies to CD47 and PD-L1 obtained by such expression in such recombinant host cells is referred to herein as "recombinant antibodies." The invention also relates to the progeny of cells from such host cells and antibodies to CD47 and PD-L1 obtained analogously.

Nucleic acid molecules encoding anti-CD47/PD-L1 antibodies of the invention and vectors comprising these nucleic acid molecules can be used for transfection of a suitable mammalian or cell thereof, plant or cell thereof, bacterial or yeast host cell. Transformation can be by any known technique for introducing polynucleotides into a host-cell. Methods for introduction of heterologous polynucleotides into mammalian cells are well known in the art and include dextran—mediated transfection, cationic polymer-nucleic acid complex transfection, calcium phosphate precipitation, polybrene—mediated transfection, protoplast fusion, encapsulation of the polynucleotide(s) in liposomes, and direct microinjection of DNA into nuclei. In addition, nucleic acid molecules may be introduced into mammalian cells by viral vectors. Methods for transfecting cells are well known in the art. See, e.g., U.S. Pat. Nos. 4,399,216, 4,912,040, 4,740,461 and 4,959,455. Methods for transforming plant cells are well known in the art, including, e.g., Agrobacterium-mediated transformation, biolistic transformation, direct injection, electroporation and viral transformation. Methods of transforming bacterial and yeast cells are also well known in the art.

Mammalian cell lines used as hosts for transformation are well known in the art and include a plurality of immortalized cell lines available. These include, e.g., Chinese hamster ovary (CHO) cells, NS0 cells, SP2 cells, HEK-293T cells, FreeStyle 293 cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines are selected by determining which cell lines have high expression levels and provide for necessary characteristics of protein produced. Other cell lines that may be used are insect cell lines, such as Sf9 or Sf21 cells. When recombinant expression vectors encoding antibodies to CD47 and PD-L1 are introduced into mammalian host cells, the antibodies are produced by culturing the host cells for a period of time sufficient to allow for expression of the antibodies in host cells or, more preferably, secretion of the antibodies into the culture medium in which the host cells are grown. Antibodies to CD47 and PD-L1 can be isolated from the nutrient medium using standard protein purification methods Plant host cells include, e.g., *Nicotiana, Arabidopsis*, duckweed, corn, wheat, potato, etc. Bacterial host cells include *E. coli and Streptomyces* species. Yeast host cells include *Schizosaccharomyces pombe, Saccharomyces cerevisiae* and *Pichia pastoris*.

Furthermore, level of production of antibodies to CD47 and PD-L1 of the invention from production cell lines can be enhanced using a number of known techniques. For example, the glutamine synthetase gene expression system (the GS system) is a common approach for enhancing expression under certain conditions. The GS system is discussed in whole or part in connection with EP Nos. 0216846, 0256055, 0323997 and 0338841.

It is likely that antibodies to CD47 and PD-L1 expressed by different cell lines or in transgenic animals will have a different glycosylation profile as compared to each other. However, all antibodies to CD47 and PD-L1 encoded by the nucleic acid molecules described herein or comprising the amino acid sequences provided herein are part of the present invention, regardless of the glycosylation of the binding molecules, and, in general, regardless of the presence or absence of post-translational modifications.

Preparation of Antibodies

The invention also relates to methods and processes for producing antibodies to CD47 and PD-L1 and antigen-binding fragments thereof.

Monoclonal Antibodies

Monoclonal antibodies may be prepared using the hybridoma method first described by Kohler, et al. Nature 256,1975, p. 495, or may using recombinant DNA methods (U.S. Pat. No. 4,816,567).

When using a hybridoma-based method, a mouse or other suitable host animal, such as a hamster, is immunized according to the method described above, in order to cause the formation of lymphocytes that produce or can produce antibodies that are capable of specifically binding to the protein used for immunization. According to another embodiment, lymphocytes can be produced by in vitro immunization. After immunization, the lymphocytes are fused with a myeloma cell line using a suitable fusing agent, such as polyethylene glycol, to produce a hybridoma cell.

The hybridoma cells thus obtained are seeded and grown in a suitable culture medium, which preferably contains one or more substances that inhibit the growth or survival of unfused parent myeloma cells. For example, if the parent myeloma cells do not contain the enzyme hypoxanting guanine phosphoribosyl transferase (HGPRT or HPRT), then the culture medium for hybridomas should usually include hypoxanthine, aminopterin and thymidine (HAT medium), i.e. substances that inhibit the growth of cells deficient in HGPRT.

Preferred myeloma cell lines are mouse myeloma lines, such as those based on murine tumor cell lines MORS-21 and MPC-11, which can be obtained from the Salk Institite Cell Disrtibution Center, San Diego, pc. California, USA, and lines SP-2 or X63-Ag8-653, which can be obtained from the American Type Culture Collection, Rockville, ea. Maryland, USA. The use of human mouse myeloma and mouse-human heteromyeloma cell lines for the production of monoclonal antibodies has also been described (Kozbor, J. Immunol, 133, 1984, p. 3001).

Preferably, the binding specificity of monoclonal antibodies obtained by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

After identifying hybridoma cells that produce antibodies of the desired specificity, affinity, and/or activity, the clones can be subcloned using the limiting dilution method and grown by standard methods. Suitable culture media for this purpose include, for example, D-MEM or RPMI-1640 medium. In addition, the hybridoma cells may be grown in vivo as ascites tumors in an animal e.g, by intraperitoneal (i.p.) injection of the cells into mice.

The monoclonal antibodies secreted by the subclones can be separated from the culture medium, ascites fluid, or serum by conventional antibody purification techniques such as, for example, affinity chromatography (e.g., using protein A- or protein G-Sepharose™) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of specific binding to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not produce antibody protein without being transfected, to obtain the synthesis of monoclonal antibodies in the recombinant host cells. A review of articles on recombinant expression in bacteria of DNA encoding the antibody.

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992), as well as combinatorial infection and in vivo recombination as a strategy for constructing very large phage libraries (Waterhouse et al., Nucl. Acids. Res. 21:2265-2266 (1993). Thus, these techniques are viable alternatives to traditional monoclonal antibody hybridoma techniques for isolation of monoclonal antibodies.

The DNA that encodes the antibody may be modified, for example, so as to produce chimeric or fusion antibody polypeptides, for example, by substituting heavy chain and light chain (CH and CL) constant region sequences for the homologous murine sequences (U.S. Pat. No. 4,816,567 and Morrison, et al., Proc. Natl. Acad. Sci. USA: 81:6851 (1984), or by covalently linking the immunoglobulin coding sequence to all or part of the coding sequence of a non-immunoglobulin polypeptide (heterologous polypeptide. The non-immunoglobulin polypeptide sequences can be substituted for the constant regions of an antibody, or they can be substituted for the variable domains of the antigen-binding center of an antibody to create a chimeric bivalent antibody comprising one antigen-binding site having specificity for an antigen and another antigen-binding site having specificity for a different antigen.

Humanized Antibodies

Methods for producing "humanized" non-human animal antibodies are well known in the art. Preferably, the humanized antibody has one or more integral amino acid residues introduced into it from a source which is non-human. These non-human amino acid residues are often referred to as "import" residues because they are typically taken from an "import" variable region. Humanization can be essentially performed following the method of Winter and co-authors (Jones et al., Nature, 321:522-525 (1986) by replacing the hypervariable region sequences with the corresponding sequences of a human antibody. Accordingly, such "humanized" antibodies are chimeric antibodies (U.S. Pat. No. 4,816,567) in which a region, which is substantially less than an intact human variable region, has been substituted by the corresponding sequence from a non-human species. In practice, humanized antibodies are typically human antibodies in which some hypervariable region residues and possibly some FR residues are substituted by residues from analogous regions in rodent antibodies.

The choice of human variable regions, both light and heavy, to be used in producing the humanized antibodies is very important to reduce antigenicity and HAMA response (human anti-mouse antibody) when the antibody is intended for human therapeutic use. According to the so-called "best-fit" method, the sequence of the variable region of a rodent antibody is screened against the entire library of known human variable domain sequences. The human V domain sequence which is closest to that of the rodent is identified and the human framework region (FR) within it is selected, which is suitable for use in the humanized antibody (Sims et al., J. Immunol. 151:2296 (1993). In another method, a specific framework region is used, obtained from a consensus sequence of a certain subgroup of light or heavy chains of all human antibodies. The same framework may be used for several different humanized antibodies (Carter et al., Proc. Natl. Acad. Sci. USA: 89:4285 (1992).

It is also important that antibodies be humanized with retention of high binding affinity for the antigen and other significant biological properties. To this end, according to a preferred method, humanized antibodies are prepared by analysis of the parental sequences and various humanized products using conceptual three-dimensional models of the parental and humanized sequences. Three-dimensional immunoglobulin models are commonly available and are familiar to those skilled in the art. Computer programs are available which illustrate and display possible three-dimensional conformational structures of selected candidate immunoglobulin sequences. Inspection of these images permits analysis of the possible role of the residues in the functioning of the candidate immunoglobulin sequence, i.e., the analysis of residues that influence the ability of the candidate immunoglobulin to bind to antigen. In this fashion, FR residues can be selected and combined with recipient and import sequences to achieve the desired antibody characteristics, such as increased affinity for the target antigen(s). In general, the hypervariable region residues are directly and most substantially involved in influencing antigen binding.

The humanized antibody may be an antibody fragment, such as Fab, which is optionally conjugated with one or more cytotoxic agent(s) in order to generate an immunoconjugate. Alternatively, the humanized antibody may be a full-length antibody, such as a full-length IgG1 antibody.

Human Antibodies and Methodology Based on Phage Display Library

As an alternative to humanization, human antibodies can be generated. For example, it is now possible to produce transgenic animals (e.g., mice) that are capable, after immunization, of producing a full range of human antibodies without endogenous immunoglobulin production. For example, it has been described that the homozygous deletion of the antibody heavy-chain joining region (JH) gene in chimeric and germ-line mutant mice results in complete inhibition of endogenous antibody production. The transfer of the human germ-line immunoglobulin gene array into such germ-line mutant mice results in the production of human antibodies after antigen challenge (U.S. Pat. Nos. 5,545,806, 5,569,825, 5,591,669 (all of GenPharm); U.S. Pat. No. 5,545,807; and WO 97/17852).

Alternatively, phage display technology (McCafferty et al., Nature, 348:552-554 (1990) can be used to produce human antibodies and antibody fragments in vitro from immunoglobulin variable (V) region gene repertoire from immunized donor bodies. According to this technique, antibody V-region genes are cloned in-frame with either a major or minor coat protein gene of a filamentous bacteriophage, such as M13 or fd, and displayed as functional antibody fragments on the surface of a phage particle. Since the filamentous particle contains a single-stranded DNA copy of the phage genome, selections based on the functional properties of the antibody also result in selection of a gene encoding an antibody exhibiting said properties. Thus, the phage mimics some of B-cell properties. Phage display can be performed in a variety of formats. Several sources of V-gene segments can be used for phage display. Clackson et al., Nature, 352:624-628 (1991) isolated various arrays of anti-oxazolone antibodies from a small random combinatorial library of V genes derived from the spleen of immunized mice. A repertoire of V genes from unimmunized human donors can be constructed and antibodies against a diverse array of antigens (including self-antigens) can be isolated essentially following the techniques described by Marks et al., J. Mol. Biol. 222:581-597 (1991).

As described above, human antibodies may also be generated by in vitro activated B cells (see U.S. Pat. Nos. 5,567,610 and 5,229,275).

Antibody Fragments

In certain circumstances, it is advisable to use antibody fragments rather than whole antibodies. The small sizes of the fragments contributes to rapid clearance thereof and may contribute to better penetration into dense tumors.

Various techniques have been developed for the production of antibody fragments. Traditionally, these fragments were derived via proteolytic digestion of intact antibodies. However, these fragments can now be obtained directly by recombinant host cells. Fab, Fv and ScFv antibody fragments can be expressed in and secreted from E. coli, thus allowing to facilitate the production of large amounts of these fragments. Antibody fragments can be isolated from the antibody phage libraries described above. According to another embodiment, Fab'-SH fragments can be directly isolated from E. coli and chemically coupled to form F(ab')2 fragments (Carter et al., Bio/Technology 10:163-167 (1992). According to another approach, F(ab')$_2$ fragments can be isolated directly from recombinant host cell culture. Fab and F(ab')$_2$ with increased in vivo half-life retaining epitope binding receptor residues are described in U.S. Pat. No. 5,869,046. Other techniques for the obtaining antibody fragments should be apparent to those skilled in the art. In other embodiments, the antibody of choice is a single chain Fv fragment (scFv) (see WO 93/16185; U.S. Pat. Nos. 5,571,894 and 5,587,458). Fv and scFv are the only species with intact binding sites that are devoid of constant regions; as a result, they are suitable for reduced nonspecific binding during in vivo use. Fusion proteins carrying scFv can be designed to produce fusion of the effector protein either at the N- or at the C-terminus of the scFv. The antibody fragment may also be a "linear antibody", e.g., as described in U.S. Pat. No. 5,641,870. Such linear antibody fragments may be monospecific or bispecific.

Multispecific Antibodies

Multispecific antibodies are antibodies that have binding specificity for at least two different epitopes. For example, bispecific antibodies may bind to two different epitopes of protein. Other multispecific antibodies may combine a binding site for CD47 and PD-L1 in combination with a binding site for another protein. Bispecific antibodies can be obtained as full-length antibodies or antibody fragments (e.g., F(ab')$_2$ fragments of bispecific antibodies).

Methods for producing multiispecific antibodies are known in the art. For example, traditional production of full-length bispecific antibodies is based on the co-expression of two immunoglobulin heavy chain/light chain pairs, where the two chains have different specificities. Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography in several steps, is rather cumbersome, and the product yield is low. Similar processes are described in WO 93/08829.

According to a different approach, antibody variable domains with the desired binding specificity (antigen-binding sites of an binding) are fused to immunoglobulin constant domain sequences. Preferably, the fusion is made with an Ig heavy chain constant region, comprising at least a portion of the hinge, $C_H2$, and $C_H3$ regions. Preferably, the first heavy chain constant region ($C_H1$) containing the site necessary for light chain binding is present in at least one of the fusions. DNAs encoding the immunoglobulin heavy chain fusions and, if desired, the immunoglobulin light chain, are inserted into various expression vectors, and are co-transfected into a suitable host cell. This provides for greater flexibility in selecting mutual proportions of the three polypeptide fragments in embodiments when unequal ratios of the three polypeptide chains are used in the construction to provide optimum yields. It is, however, possible to insert the coding sequences into two or all three polypeptide chains in a single expression vector when the expression of at least two polypeptide chains in equal ratios results in high yields, or when the ratios have no significant affect.

In a preferred embodiment of this approach, the bispecific antibodies are a hybrid immunoglobulin heavy chain providing for a first binding specificity in a first arm, and a hybrid immunoglobulin heavy chain/light chain pair (providing for a second binding specificity) in a second arm. It was found that this asymmetric structure facilitates the separation of the desired bispecific molecule from unwanted immunoglobulin chain combinations, as the presence of an immunoglobulin light chain in only one half of the bispecific molecule facilitates separation. This approach is disclosed in WO 94/04690. For more details regarding producing bispecific antibodies see, for example, Suresh et al., Methods in Enzymology 121:210 (1986).

According to another approach described in U.S. Pat. No. 5,731,168, the interface between a pair of antibody molecules can be constructed to maximize the percentage of heterodimers which are obtained from recombinant cell culture. The preferred interface comprises at least a portion of the CH3 region. According to this method, one or more small amino acids with side chains from the interface of the first antibody molecule are replaced with larger side chains (e.g., tyrosine or tryptophan). Compensatory "cavities" of identical or similar size to the large side chain(s) are created on the interface of the second antibody molecule by replacing amino acids containing large side chains with amino acids containing smaller side chains (e.g., alanine or threonine). This provides a mechanism for increasing the yield of heterodimer as compared to other unwanted end-products.

Bispecific antibodies include cross-linked or "heteroconjugate" antibodies. For example, one of the antibodies in the heteroconjugate can be coupled to avidin, and the other to biotin. Such antibodies can, for example, be used to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with various cross-linking techniques.

Methods of obtaining bispecific antibodies from antibody fragments have also been described in the literature. For example, bispecific antibodies can be obtained by chemical binding. Brennan et al., Science 229:81 (1985) have described a procedure, according to which intact antibodies are proteolytically cleaved to produce F(ab')$_2$. These fragments are reduced in the presence of the dithiol complexing agent, such as sodium arsenite, to stabilize vicinal dithiols and prevent formation of intermolecular disulfide bonds. The Fab' fragments produced are then converted to thionitrobenzoate (TNB) derivative. One of the Fab'-TNB derivatives is then reconverted to Fab'-thiol by reduction with mercaptoethylamine and is mixed with an equimolar amount of another Fab'-TNB derivative to obtain the bispecific antibody. The bispecific antibodies produced can be used as agents for selective immobilization of enzymes.

Recent progress has facilitated the direct recovery of Fab'-SH fragments from E. coli, which can be chemically coupled to produce bispecific antibodies. Shalaby et al., J. Exp. Med. 175:217-225 (1992) describe the production of F(ab')$_2$ of a fully humanized bispecific antibody molecule. Each Fab' was separately secreted from E. coli and subjected to direct chemical coupling in vitro to form the bispecific antibody. The bispecific antibody thus obtained was able to bind to cells overexpressing the ErbB2 receptor and normal human T cells, as well as trigger the lytic activity of human cytotoxic lymphocytes against human breast tumor targets.

Various techniques for obtaining and isolating bispecific antibody fragments directly from recombinant cell culture have also been described. For example, bispecific antibodies have been produced using leucine zippers (Kostelny et al, J. Immunol. 148(5):1547-1553 (1992). The leucine zipper peptides from Fos and Jun proteins were linked to the Fab' of two different antibodies by gene fusion. Antibody homodimers were reduced at the hinge region to form monomers and then re-oxidized to obtain the antibody heterodimers. This method can also be used to obtain homodimeric antibodies. The "double antibody" technology described by Hollinger et al., Proc. Natl. Acad. Sci. USA 90:6444-6448 (1993) is an alternative mechanism for producing bispecific antibody fragments. The fragments comprise a VH region connected to a VL region by a linker which is too short to allow pairing between the two domains on the same chain. Accordingly, the VH and VL regions of one fragment should pair with the complementary VL and VH regions of another fragment, thereby forming two antigen-binding sites. Another strategy for producing bispecific antibody fragments using single-chain (Fv)-(sFv) dimers has also been described (see Gruber et al., J. Immunol., 152: 5368 (1994).

The invention also provides antibodies with more than two valencies. For example, trispecific antibodies can be produced.

Polyvalent Antibodies

A polyvalent antibody may be internalized (and/or catabolized) by a cell expressing an antigen, to which the antibody binds, faster than a bivalent antibody. The antibodies of the present invention may be multivalent antibodies (other than the IgM class) with three or more antigen binding sites (for example, tetravalent antibodies) that can be easily obtained by recombinant expression of a nucleic acid encoding an antibody polypeptide chains. The polyvalent antibody can comprise a dimerization domain and three or more antigen binding sites. The preferred dimerization domain comprises (or consists of) an Fc fragment or a hinge region. In this scenario, the antibody will comprise an Fc fragment and three or more antigen binding sites at N-terminus to the Fc fragment. The preferred polyvalent antibody herein comprises (or consists of) 3 to about 8, but preferably 4, antigen binding sites. The polyvalent antibody comprises at least one polypeptide chain (and preferably two polypeptide chains), wherein the polypeptide chain(s) comprise two or more variable regions. For example, the polypeptide chain(s) may comprise VD1-(X1)n-VD2-(X2)n-Fc, wherein VD1 refers to a first variable region, VD2 refers to a second variable region, Fc refers to one polypeptide chain of an Fc fragment, X1 and X2 refer to an amino acid or polypeptide, and n is 0 or 1. For example, the polypeptide chain(s) may comprise the following chain: VH—CH 1-flexible linker-VH-CH1-Fc fragment; or VH-CH1-VH-CH1-Fc fragment. The polyvalent antibody herein preferably further comprises at least 2 (and preferably 4) light chain variable region polypeptides. The polyvalent antibody herein may, for example, comprise from about 2 to about 8 light chain variable region polypeptides. In the context of the present invention, the light chain variable region polypeptides comprise a light chain variable region and, optionally, further comprise a CL region.

Pharmaceutical Compositions

In another aspect, the invention provides a pharmaceutical composition comprising a CD47/PD-L1-specific antibody as an active ingredient (or as the only active ingredient). The pharmaceutical composition may include at least one antibody that is specific for CD47 and PD-L1 and/or one or more additional binding molecules (e.g., antibodies) that target one or more of the corresponding surface receptors, as described herein. In some embodiments, the compositions are intended to improve, prevent, or treat disorders that are mediated by IgG.

"Pharmaceutical composition" means a composition comprising an anti-CD47/PD-L1 antibody of the present invention and at least one of components selected from the group consisting of pharmaceutically acceptable and pharmacologically compatible excipients, such as fillers, solvents, diluents, carriers, auxiliary, distributing agents, delivery agents, preservatives, stabilizers, emulsifiers, suspending agents, thickeners, prolonged delivery controllers, the choice and proportions of which depend on the type and route of administration and dosage. Pharmaceutical compositions of the present invention and methods of preparation thereof will be undoubtedly apparent to those skilled in the art. The pharmaceutical compositions should preferably be manufactured in compliance with the GMP (Good Manufacturing Practice) requirements. The composition may include a buffer composition, tonicity agents, stabilizers and solubilizers. Prolonged action of composition may be achieved by agents slowing down absorption of active pharmaceutical ingredient, for example, aluminum monostearate and gelatine. Examples of suitable carriers, solvents, diluents and delivery agents include water, ethanol, polyalcohols and their mixtures, oils, and organic esters for injections.

"Medicament (drug)"—is a substance or a mixture of substance as a pharmaceutical composition in the form of tablets, capsules, powders, lyophilisates, injections, infusion, ointments and other ready forms intended for restoration, improvement or modification of physiological functions in humans and animals, and for treatment and preventing of diseases, for diagnostics, anesthesia, contraception, cosmetology and others. Any method for administering peptides, proteins or antibodies which is accepted in the art may be suitably employed for an anti-CD47/PD-L1 antibody of the invention.

The term "pharmaceutically acceptable" refers to one or more compatible liquid or solid components that are suitable for administration in a mammal, preferably a human.

The term "excipient" is used herein to describe any ingredient other than the above ingredients of the invention. These are substances of inorganic or organic nature which are used in the pharmaceutical manufacturing in order to give drug products the necessary physicochemical properties.

As used herein, "buffer", "buffer composition", "buffering agent" refers to a solution, which is capable of resisting changes in pH by the action of its acid-base conjugate components, and which allows the anti-CD47/PD-L1 antibody drug to resist changes in pH. Generally, the pharmaceutical composition preferably has a pH in the range from 4.0 to 8.0. Examples of buffers used include, but are not limited to, acetate, phosphate, citrate, histidine, succinate, etc. buffer solutions.

The terms "tonic agent", "osmolyte" or "osmotic agent", as used herein, refer to an excipient that can increase the osmotic pressure of a liquid antibody formulation. "Isotonic" drug is a drug that has an osmotic pressure equivalent to that of human blood. Isotonic drugs typically have an osmotic pressure from about 250 to 350 mOsm/kg. Isotonic agents used include, but are not limited to, polyols, saccharides and sucrose, amino acids, metal salts, for example, sodium chloride, etc.

"Stabilizer" refers to an excipient or a mixture of two or more excipients that provide the physical and/or chemical stability of the active agent. Stabilizers include amino acids, for example, but are not limited to, arginine, histidine, glycine, lysine, glutamine, proline; surfactants, for example, but are not limited to, polysorbate 20 (trade name: Tween 2™), polysorbate 80 (trade name: Tween 8™), polyethylene-polypropylene glycol and copolymers thereof (trade names: Poloxamer, Pluronic, sodium dodecyl sulfate (SDS); antioxidants, for example, but are not limited to, methionine, acetylcysteine, ascorbic acid, monothioglycerol, sulfurous acid salts, etc.; chelating agents, for example, but are not limited to, ethylenediaminetetraacetic acid (EDTA), diethylenetriaminepentaacetic acid (DTPA), sodium citrate, etc.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition of the invention can be manufactured, packaged, or widely sold in the form of a single unit dose or a plurality of single unit doses in the form of a ready formulation. The term "single unit dose", as used herein, refers to discrete quantity of a pharmaceutical composition containing a predetermined quantity of an active ingredient. The amount of active ingredient is usually equal to the dosage of the active ingredient to be administered to the subject, or a convenient part of such a dosage, for example, half or one third of that dosage.

The pharmaceutical compositions according to the present invention are typically suitable for parenteral administration as sterile formulations intended for administration in a human body through the breach in skin or mucosal barriers, bypassing the gastrointestinal tract by virtue of injection, infusion and implantation. For example, parenteral administration includes, inter alia, subcutaneous, intraperitoneal, intramuscular, intrasternal, intravenous, intraarterial, intrathecal, intraventricular, intraurethral, intracranial, intrasynovial, transdermal injection or infusions; and kidney dialytic infusion techniques. Regional perfusion is also provided. Prefered embodiments include intravenous and subcutaneous routes. Any method for administering peptides or proteins, which is accepted in the art may be suitably employed for an anti-CD47/PD-L1 antibody of the invention.

Injectable formulations may be manufactured, packaged, or sold, without limitation, in unit dosage form, such as in ampoules, vials, in plastic containers, pre-filled syringes, autoinjection devices. Formulations for parenteral administration include, inter alia, suspensions, solutions, emulsions in oily or aqueous bases, pastes, and the like.

In another embodiment, the invention provides a composition for parenteral administration comprising a pharmaceutical composition which is provided in dry (i.e. powder or granular) form for reconstitution with a suitable base (e.g., sterile pyrogen-free water) prior to administration. Such formulation can be obtained by, for example, lyophilisation process, which is known in the art as freeze drying, and which involves freezing a product followed by removal of solvent from frozen material.

Antibody to CD47 and PD-L1 of the invention can also be administered intranasally or by inhalation, either alone, as a mixture with a suitable pharmaceutically acceptable excipient from an inhaler, such as a pressurised aerosol container, pump, spray, atomiser, or nebuliser, wherein a suitable propellant is used or not used, or as nasal drops, or spray.

Dosage forms for parenteral administration may be formulated to be immediate or modified release. Modified release formulations include delayed-, sustained-, pulsed-, controlled-, targeted and programmed release.

Therapeutic Use of Anti-CD47/PD-L1 Antibody of the Invention

In one aspect, an anti-CD47/PD-L1 antibody of the invention is used for treating disorders mediated by CD47 and PD-L1, for example, a disease or disorder selected from the group comprising: (HNSCC) head and neck squamous cell carcinoma, cervical cancer, cancer of unknown primary, glioblastoma, esophageal cancer, bladder cancer, TNBC (triple-negative breast cancer), CRC (colorectal cancer), hepatocellular carcinoma, melanoma, NSCLC (non-small cell lung cancer), kidney cancer, ovarian cancer, Hodgkin's lymphoma, MSI CRC (colorectal cancer with with microsatellite instability), leukemia (acute leukemia or myeloblastic leukemia), non-Hodgkin's lymphoma, multiple myeloma, myelodysplastic syndrome.

In one aspect, the subject of treatment, or patient, is a mammal, preferably a human subject. The above subject can be male or female and of any age.

In the case of a tumor (for example, cancer), the therapeutically effective amount of the antibody or fragment thereof (for example, an antibody or fragment thereof that specifically binds to CD47 and PD-L1) may reduce the number of cancer cells; reduce the initial tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. The antibody or fragment thereof may to some extent prevent growth and/or kill existing cancer cells, it may be cytostatic and/or cytotoxic. For cancer therapy, in vivo efficacy can, for example, be measured by assessing overall survival (OS), time to tumor progression (TTP), overall tumor response rate to treatment (ORR), duration of response (DR) and/or quality of life.

As used herein, the terms "co-administration", "co-administered" and "in combination with", referring to an anti-CD47/PD-L1 antibody and one or more different therapeutic agents, are expected to mean, refer to or include the following:
1) simultaneous administration of such combination of an anti-CD47/PD-L1 antibody of the invention and therapeutic agent to a patient in need of treatment, when such components are formulated together into a single dosage form which releases said components at substantially the same time to said patient,
2) substantially simultaneous administration of such combination of an anti-CD47/PD-L1 antibody of the invention and therapeutic agent to a patient in need of treatment, when such components are formulated separately in different dosage forms, the introduction of which occurs at almost the same time to the indicated patient, after what these components are released almost simultaneously specified patient,
3) sequential administration of such combination of an anti-CD47/PD-L1 antibody of the invention and therapeutic agent to a patient in need of treatment, when such components are formulated apart from each other into separate dosage forms which are taken at consecutive times by said patient with a significant time interval between each administration, whereupon said components are released at substantially different times to said patient; and
4) sequential administration of such combination of ntibodies to CD47 and PD-L1 according to this invention and therapeutic agent to a patient in need of treatment, when such components are formulated together into a single dosage form which releases said components in a controlled manner, whereupon they are concurrently, consecutively, or jointly released at the same and/or different times to said patient, where each portion may be administered by either the same or different routes.

An anti-CD47/PD-L1 antibody of the invention can be administered without further therapeutic treatment, i.e., as an independent therapy. Furthermore, treatment by an antibody of the invention may comprise at least one additional therapeutic treatment (combination therapy). In some embodiments of the invention, the anti-CD47/PD-L1 antibody may be administered in combination with or be formulated with a different cancer medicament/drug.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); beta-lapachone; lapachol; colchicines; betulinic acid; camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (e.g., cryptophycin 1 and cryptophycin 8); dolastatin; duocarmycin (including the synthetic analogues, KW-2189 and CB 1-TM1); eleutherobin; pancratistatin; sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, e.g., calicheamicin gamma II and calicheamicin omega II (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN® morpholino-doxorubicin, cyanomorpholino-doxorubicin, 2-pyrrolino-doxorubicin, doxorubicin HCl liposome injection (DOXOL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine;pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamideglycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins;mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2''-trichlorotriethylamine; trichothecenes (e.g., T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE®), and docetaxel) (TAXOTERE®); chlorambucil; 6-thioguanine; mercaptopurine; methotrexate; platinum agentssuch as cisplatin, oxaliplatin, and carboplatin; vincas, which prevent tubulin polymerization fromforming microtubules, including vinblastine (VELBAN®), vincristine (ONCOVIN®), vindesine (ELDISINE®), (FILDESIN®), and vinorelbine (NAVELBINE®); etoposide (VP16); ifosfamide; mitoxantrone; leucovorin; novantrone; edatrexate; daunomycin; aminopterin; ibandronate; topoisomerase inhibitor RFS 2000; difluorometlhylornithine (DMFO); retinoidssuch as retinoic acid, including bexarotene (TARGRETIN®); bisphosphonates such asclodronate (for example, BONEFOS® or OSTAC®), etidronate (DIDROCAL®), NE-58095, zoledronic acid/zoledronate (ZOMETA®), alendronate (FOSAMAJX®), pamidronate (AREDIA®), tiludronate (SKELID®), or risedronate (ACTONEL®); troxacitabine (1,3-dioxolane nucleoside cytosine analog); antisense oligonucleotides, particularly those that inhibit expression of genes in signaling pathways implicated in aberrant cell proliferation, such as for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECANC®); rmRH (e.g., ABARELIX®); BAY439006 (sorafenib; Bayer); SU-11248(Pfizer); perifosine, COX-2 inhibitor (e.g., celecoxib or etoricoxib), proteosome inhibitor (e.g., PS341); bortezomib (VELCADE®); CCI-779; tipifarnib (RI 1577); orafenib, ABT510; Bcl-2inhibitor such as oblimersen sodium (GENASENSE®); pixantrone; EGFR inhibitors (seedefinition below); tyrosine kinase inhibitors (see definition below); and pharmaceuticallyacceptable acids or derivatives of any of the above; as well as combinations of two or moreof the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate or inhibit hormone action on tumors, such as anti-estrogens with mixed agonist/antagonist profile, including, tamoxifen (NOLVADEX®), 4-hydroxytamoxifen, toremifene (FARESTON®), idoxifene, droloxifene, raloxifene) (EVTSTA®), trioxifene, keoxifene, and selective estrogen receptor modulators (SERMs), such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors, such as formestane and exemestane (AROMASIN®), and nonsteroidal aromatase inhibitors, such as anastrazole (AREVIIDEX®), letrozole (FEMARA®) and aminoglutethimide, and other aromatase inhibitors including vorozole (RIVISOR®), megestrol acetate (MEGASE®), fadrozole, imidazole; lutenizing hormone-releasing hormone agonists, including leuprolide (LUPRON® and ELIGARD®), goserelin, buserelin, and tripterelin; sex steroids, including progestines, such as megestrol acetate and medroxyprogesterone acetate, estrogens, such as diethylstilbestrol and premarin, and androgens/ retinoids such as fluoxymesterone, all transretionic acid and fenretinide; onapristone; anti-progesterones; estrogen receptor down-regulators (ERDs); anti-androgens, such as flutamide, nilutamide and bicalutamide; testolactone; and pharmaceutically acceptable salts, acids or derivatives of any of the above; as well as combinations of two or more of the above.

Other therapeutic agents that can be used in combination with anti-CD47/PD-L1 antibodies of the invention can be inhibitors of growth factor function, for example, such inhibitors include growth factor antibodies and growth factor receptor antibodies (for example, the anti-erbB2 antibody trastuzumab [Herceptin™], the anti-EGFR antibody panitumumab, the anti-erbB1 antibody cetuximab [Erbitux™, C225] and any growth factor or growth factor receptor antibodies disclosed by Stern et al. Critical reviews in oncology/haematology, 2005, Vol. 54, pp11-29); antiangiogenic agents such as those which inhibit the effects of vascular endothelial growth factor, [for example, the antivascular endothelial cell growth factor antibody bevacizumab (Avastin™)], anti-vascular endothelial growth factor receptor antibodies, such as anti-KDR antibodies and antiflt1 antibodies; antisense nucleotides, for example those which are directed to the targets listed above, such as ISIS 2503, an anti-ras antisense or G3139 (Genasense®), an anti bcl2 antisense; gene therapy approaches, including, for example, approaches to replace aberrant genes, such as aberrant p53 or aberrant BRCA1 or BRCA2, GDEPT (genedirected enzyme pro-drug therapy), approaches such as those using cytosine deaminase, thymidine kinase or a bacterial nitroreductase enzyme and approaches to increase patient tolerance to chemotherapy or radiotherapy, such as multi-drug resistance gene therapy; immunotherapy approaches, including, for example, treatment with Alemtuzumab (campath-1H), a monoclonal antibody directed at CD52, or treatment with antibodies directed at CD22, ex vivo and in vivo approaches to increase the immunogenicity of patient tumour cells, transfection with cytokines such as interleukin 2, interleukin 4 or granulocyte macrophage colony stimulating factor, approaches to decrease T cell anergy, such as treatment with monoclonal antibodies inhibiting CTLA-4 function, approaches using transfected immune cells, such as cytokine transfected dendritic cells, approaches using cytokine transfected tumour cell lines and approaches using anti idiotypic antibodies, adoptive T-cell transfer using T-cells that have been nonspecifically activated or targeted to a specific antigen of interest ex vivo; inhibitors of protein degradation, such as proteasome inhibitor, such as Velcade (bortezomid); biotherapeutic therapeutic approaches, for example, those which use peptides or proteins (such as antibodies or soluble external receptor domain constructions), which either sequester receptor ligands, block ligand binding to receptor or decrease receptor signalling (for example, due to enhanced receptor degradation or lowered expression levels).

Doses and Routes of Administration

The anti-CD47/PD-L1 antibody of the invention should be administered in an amount that is effective in treatment of the condition in question, i.e. in doses and during the periods of time required to achieve the desired result. A therapeutically effective amount may vary according to factors such as the specific condition being treated, the age, sex and weight of the patient, and whether the anti-CD47/PD-L1 antibody is being administered as a stand-alone treatment or in combination with one or more additional treatments.

Dosage regimens may be adjusted to provide the optimum response. For example, a single bolus may be administered, several divided doses may be administered over time or the dose may be proportionally reduced or increased as indicated by the exigencies of the therapeutic situation. Particularly useful is the manufacture of parenteral compositions in a standard dosage form for ease of administration and uniformity of dosing. A unit dosage form as used herein is intended to refer to physically discrete units suited as unitary dosages for patients/subjects to be treated; each unit contains a predetermined quantity of active compound calculated to produce the desired therapeutic effect in association with the desired pharmaceutical carrier. The specification for the standart dosage forms of the invention is typically dictated by and directly dependent on (a) the unique characteristics of a chemotherapeutic agent and specific therapeutic or prophylactic effect to be achieved, and (b) the limitations inherent in the art of compounding such an active compound for the treatment of subjects.

Thus, those skilled in the art will recognize from the disclosure herein that dosages and dosage regimens are adjusted in accordance with methods well known in the therapeutic field. That is, the maximum tolerable dose can be readily established, and the effective amount providing a detectable therapeutic effect to a patient may also be determined, as can the temporal requirements for administering each agent to provide a detectable therapeutic effect to a patient. Thus, although some doses and dosage regimens are given as examples in this document, these examples in no way limit the dosages and dosage regimens that may be necessary for the patient in the practice of the present invention.

It is to be noted that dosage values may vary with the type and severity of the condition to be alleviated and may include single or multiple doses. Furthermore, it is to be understood that for any particular subject, specific dosage regimens should be adjusted over time according to the individual need and the judgment of a medical professional administering or supervising the administration of the compositions, and that dosage ranges set forth herein are exemplary only and are not intended to limit the scope or practice of the claimed compositions. Further, the dosage regimen with the compositions of this invention may be based on a variety of factors, including the type of disease, the age, weight, sex, medical condition of the patient, the severity of the condition, the route of administration, and the particular anti-CD47/PD-L1 antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the person skilled in the art. Methods for determining appropriate dosages and regimens are well-known in the art and would be understood by a skilled artisan once provided the ideas disclosed herein.

Examples of suitable administration methods are provided above.

It is believed that a suitable dose of antibodies to CD47 and PD-L1 according to this invention will be in the range of 0.1-200 mg/kg, preferably 0.1-100 mg/kg, including about 0.5-50 mg/kg, for example about 1-20 mg/kg. The antibody to CD47 and PD-L1 may be administered, e.g., in a dose of at least 0.25 mg/kg, such as at least 0.5 mg/kg, including at least 1 mg/kg, e.g., at least 1, 5 mg/kg, such as at least 2 mg/kg, e.g., at least 3 mg/kg, including at least 4 mg/kg, e.g., at least 5 mg/kg; and for example up to a maximum of 50 mg/kg, including up to a maximum of 30 mg/kg, e.g., up to a maximum of 20 mg/kg, including up to a maximum of 15 mg/kg. The administration will typically be repeated in appropriate time intervals, such as once a week, once every two weeks, once every three weeks or once every four weeks, and for as long as deemed appropriate by a responsible physician, who may, in some cases, increase or reduce the dose if necessary.

Article of Manufacture (Products) and Kits

The following embodiment of the invention is a product that contains products used to treat cancer, for example, HNSCC, cervical cancer, cancer of unknown primary, glioblastoma, esophageal cancer, bladder cancer, TNBC, CRC, hepatocellular carcinoma, melanoma, NSCLC, kidney cancer, ovarian cancer, Hodgkin's lymphoma, MSI CRC, leukemia (acute leukemia or myeloblastic leukemia), non-Hodgkin's lymphoma, multiple myeloma, myelodysplastic syndrome. The product is a container and a label or leaflet insert in the package, which are placed on the container or enclosed in it. Suitable containers are, for example, cans, vials, syringes, etc. Containers can be made from various materials, such as glass or plastic. The container contains a composition that is effective for treatment of a particular condition and may have a sterile inlet channel (for example, the container may be an intravenous solution bag or vial with a stopper that can be punctured with a hypodermic needle). At least one active ingredient in the composition is an anti-PD-L1 antibody according to the invention. The label or leaflet in the package indicates that the composition is used to treat a particular condition. The label or package leaflet in the package should additionally contain instructions for administering the antibody composition to the patient.

The package leaflet contains typical instructions which are included into the packages of therapeutic products coining on the market, including some information on indications, frequency, dose, route of administration, contraindications and/or precautions for such therapeutic products. In one embodiment, the package insert indicates that the composition is intended to be used for treatment of cancer, for example, HNSCC, cervical cancer, cancer of unknown primary, glioblastoma, esophageal cancer, bladder cancer, TNBC, CRC, hepatocellular carcinoma, melanoma, NSCLC, kidney cancer, ovarian cancer, Hodgkin's lymphoma, MSI CRC, leukemia (acute leukemia or myeloblastic leukemia), non-Hodgkin's lymphoma, multiple myeloma, myelodysplastic syndrome.

Furthermore, the article may further comprise a second container with a pharmaceutically acceptable buffer, such as bacteriostatic water for injection (BSVI), phosphate-buffered saline, Ringer's solution and dextrose solution. Furthermore, the article may include other products necessary from a commercial point of view and from the consumer's point of view, in particular, other buffers, diluents, filters, needles, and syringes.

The invention also relates to kits that can be used for various purposes, e.g., for detection of PD-L1 in tissues, cells or body fluids of a mammal Such a kit would be useful for screening associated with PD-L1 diseases. The kit includes a specific binding agent or antibody of the invention and means for indicating the reaction of the specific binding agent or anti-PD-L1 antibody, when present. In one embodiment, the antibody is a monoclonal antibody. In one embodiment, the antibody that binds PD-L1, is labeled. In another embodiment, the antibody is an unlabeled primary antibody and the kit further comprises means for detecting the primary antibody. In one embodiment, the detecting means includes a labeled second antibody that is an anti-immunoglobulin. The antibody may be labeled with a marker selected from the group consisting of a fluorochrome, an enzyme, a radionuclide and a radiopaque material. The kit may be a kit which contains antibodies to detect and quantify PD-L1 in vitro, for example, by implementing ELISA or Western blotting. Also, as in the case of articles, the kit comprises a container and a label or package insert, located on or inside the container. The container holds a composition which comprises at least one anti-PD-L1 antibody, according to the invention. Additional containers may comprise, for example, diluents and buffers, control antibodies. The label or package leaflet in the package may contain a description of the composition as well as instructions for their use in vitro or for diagnostic purposes.

Diagnostic Use and Compositions

The anti-CD47/PD-L1 antibody of the invention is also used in diagnostic processes (e.g., in vitro, ex vivo). For example, the anti-CD47/PD-L1 antibody can be used for detecting or measuring the level of CD47 and/or PD-L1 in samples obtained from a patient (e.g., tissue sample or a sample of body fluid, such as an inflammatory exudate, blood, serum, intestinal fluid, saliva or urine). Suitable methods for detection and measurement include immunoassays, such as flow cytometry, enzyme-linked immunosorbent assay (ELISA), chemiluminescent assay, radioimmunoassay, and immunohistology. The invention further includes kits, for example, diagnostic kits comprising anti-CD47/PD-L1 antibodies described herein.

EXAMPLES

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be quite clear to those skilled in the art based on the ideas disclosed in this invention that certain changes and modifications can be made without deviating from the essence and scope of the attached variations. implementation of the invention.

Example 1

Production of Recombinant Antigens and Antibodies in Suspension Culture of Mammalian Cells Sequences of extracellular domains of human CD47 (Leu19-Val134) and PD-L1 (Phe19-Arg238) (SEQ ID NOs: 107-108) were cloned into a plasmid for producing Fc-tagged protein in mammalian cells (FIG. 1) at the SalI/NotI restriction sites. The required quantities of the plasmids were produced in $E.$ $Coli$ cells and purified using Qiagen™ kit.

The sequences of variable domains of anti-CD47 antibody (B6H12, Stanford University, US20130142786) were cloned into plasmids for producing IgG1 protein in mammalian cells. The required quantities of the plasmids were produced in $E.$ $Coli$ cells and purified using Qiagen™ kit.

Antibodies and antigens were generated in established cell line obtained from Chinese hamster ovary cells (CHO-K1). Suspension culture was conducted in flasks on orbital shaker using serum-free media (Life Technologies Corporation) and in accordance with manufacturer's guidelines. For transient expression, cells in a concentration of $2*10^6$/ml were transfected by means of linear polyethyleneimine (e.g., PEI MAX, Polysciences). DNA/PEI ratio was 1:3/1:10. In 5-7 days after transfection, cell culture was centrifuged under 2000 g for 20 min and filtered through 0.22 μm filter. Target proteins were isolated from culture liquid by affine HPLC.

Recombinant Fc proteins were isolated and purified from cell culture on Protein A column for affine HPLC. The cleared culture liquid was passed through 5 ml HiTrap rProtein A Sepharose™ FF column (GE Healthcare) equilibrated with phosphate buffered saline (PBS, pH 7.4). Then the column was washed with 5 volumes of PBS to remove non-specific bound components. Bound antigen was eluted with 0,1 M glycine buffer (pH 8). The principal protein elution peak was collected and brought to neutral pH with 1 M Tris™ buffer (pH 8). All stages were conducted under 110 cm/h flow rate. Protein was then dialyzed into PBS (pH 7.4) using SnakeSkin Dialysis Tubing technique, filtered (0.22 μm), transferred into tubes and stored at −70° C.

Figure 2:
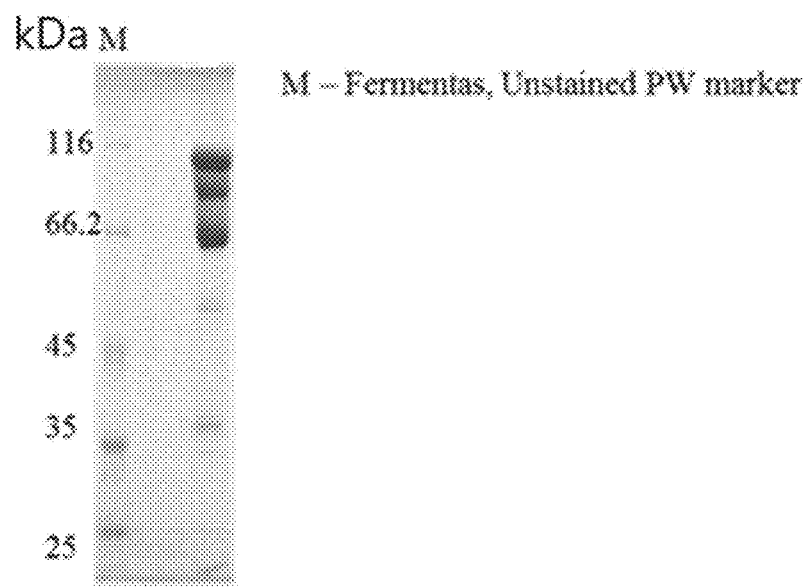
FIG. 2. SDS-gel electrophoresis in non-reducing conditions of the preparation of human CD47-Fc.

The purity of protein solution obtained was evaluated by non-reducing SDS-PAGE (12% gel) FIG. 2.

Example 2

Preparation of Full-Length Antibodies

Figure 3:
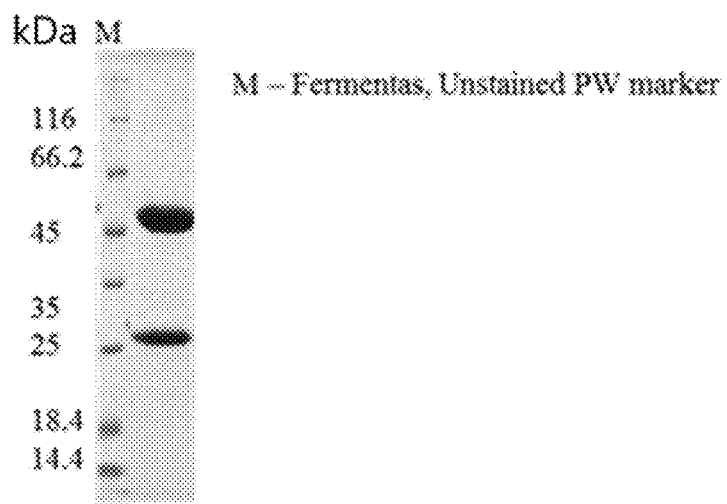
FIG. 3. SDS-gel electrophoresis in reducing conditions of the preparation of control anti-CD47 antibody B6H12 product.
Figure 4:
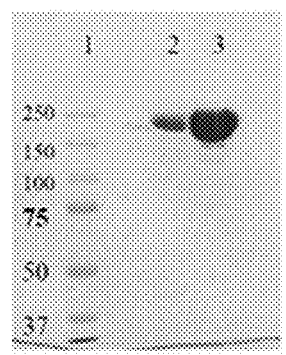
FIG. 4. SDS-gel electrophoresis in non-reducing conditions of the preparation of control anti-CD47 antibody B6H12 product.

Cloning was performed by the standard technique. PCR products comprising the genes the variable domains of the heavy and light chains of antibodies with primers containing restriction sites were produced. The variable domain of the heavy chain cloned into vector pEE-Hc IgG1 at Sal1/Nhe1 restriction sites. The variable domain of the light chain was cloned into vector pEE-CK at Sal1/BsiW1 restriction sites. Gene constructs obtained were used for transient production of proteins in CHO-T cell line. Proteins were isolated and purified according to standard methods by affinity chromatography on bacterial Protein A as described in example 1. Electrophoresis was performed in 12% denaturing PAGE supplemented with mercaptoethanol (FIG. 3) and 8% denaturing PAGE not supplemented with mercaptoethanol (FIG. 4).

Example 3

Engineering of a Naive Human Fab Phage Library MeganLib™

Total RNA of B lymphocytes from blood samples of more than one thousand individual human donors was isolated using RNeasy Mini Kit (QIAGEN™) according to the suggested protocol. RNA concentration assay was performed using Nanovue kit (GE Healthcare); the quality of isolated RNA was tested by means of 1.5% agarose gel electrophoresis.

Reverse transcription reaction was conducted using MMLV RT kit (Evrogen) according to the recommended protocol with MMuLV reverse transcriptase and random hexamer oligonucleotides as primers.

Reverse transcription products were used as a matrix in a two-stage polymerase chain reaction to obtain the genes of variable domains flanked with restriction sites; reaction was performed using oligonucleotide kit according to protocols by [J. Biol. Chem. 1999 Jun. 25; 274(26): 18218-30].

The obtained DNA product (VL-CK—VH) was treated with NheI/Eco91I restriction endonucleases and ligated into the original phagemid pH5. Ligation products were transformed into SS320 $E.$ $coli$ electrocompetent cells prepared in accordance with protocols [Methods Enzymol. 2000; 328: 333-63.]. Repertoire of combinatorial Fab phage display library MeganLib™ was $10^{11}$ transformants. Fab phage library products were prepared in accordance with the earlier described procedure [J. Mol. Biol. 1991 Dec. 5; 222(3): 581-97].

Example 4

Immunization of Llama with Human CD47 Antigen and Generation of a Phage Display Library of Llama Antibody Fragments The animal Lama Glama was immunized 5 times in succession by means of subcutaneous administration of antigen material mixed with an equal volume of complete (first injection) or incomplete (other injections) Freund's adjuvant. Recombinant human CD47 protein of Example 1 (1 mg/injection) was used as an antigen. Antigen injections were performed in the following intervals: 0, 2, 4, 5, 8 weeks. Blood samples (50 ml) were collected 5 after each injection starting from the third one. 3.8% sodium citrate was used as an anticoagulant (1:9). Blood was 2-fold diluted with a saterile saline solution. 30 ml of diluted blood solution was then layered over 15 ml of Lymphoprep™ (Axis-Shield, Norway) medium (density of 1.077 g/ml) and centrifuged for 20 min under 800 g. Mononuclear cells (lymphocytes and monocytes) were selected from plasma/Lymphoprep medium interphase zone and washed with sterile PBS.

The obtained titer of serum immunoglobulin against CD47, evaluated according to the standard protocol, turned out to be at least 1/100000, which is sufficient for preparing a library of antibodies.

Total RNA from mononuclear llama cells was isolated using RNeasy Mini Kit in accordance with the protocol (QIAGEN™). RNA concentration assay was performed using Nanovue (GE Healthcare); the quality of isolated RNA was tested by means of 1.5% agarose gel electrophoresis.

Reverse transcription reaction was conducted using MMLV RT kit (Evrogen) according to the recommended protocol with MMuLV reverse transcriptase and random hexamer primers.

Reverse transcription products were used as a matrix in a two-stage polymerase chain reaction to obtain the genes of monodomains VHH, scFv or Fab flanked with restriction sites; reaction was performed using oligonucleotide kit and protocols by [FASEB J. 2007 November; 21(13):3490-8]. The VHH gene DNA product obtained was treated with NcoI/NotI restrictases and ligated into original phagemid pscFv, which is analogous in composition to pHEN2 used in [FASEB J. 2007 November; 21 (13): 3490-8]. Ligation products were transformed into SS320 electrocompetent cells prepared in accordance with protocols [Methods Enzymol. 2000; 328: 333-63.]. The repertoires of constructed VHH-based libraries were 0,5-2*10E+8 independent transformants. The repertoires of constructed scFv/Fab-based libraries were 0,5-2*10E+9/1,2-2,5*10E+9, respectively. The phage library product was prepared in accordance with the earlier described procedure [J. Mol. Biol. 1991 Dec. 5; 222(3): 581-97].

Example 5

Selection of Phage Display Libraries of Antibody Fragments

Specific anti-CD47 phage antibodies were selected from a phage Fab, VHH, or scFv display libraries (Examples 3, 4) by conventional selection procedures described in [EMBO J. 1994 Jul. 15; 13(14):3245-60, Nat. Biotechnol. 1996 March; 14(3):309-14; J. Mol. Bio. 1.1991 Dec 5;222(3): 581-97], but using magnetic beads and KingFisher Flex device, because this technique allows performing up to 96 different schemes and variants simultaneously.

Human biotinylated PD-L1/CD47 antigen (Fc, EPEA) was purposely immobilized onto streptavidin magnetic beads (NEB) at a concentration of 10 μg/ml for the first round, 2 μg/ml for the second round, 0.4 and 0.2 μg/ml for the third round and fourth round, respectively. Antigen was incubated with the beads for 1 hour at room temperature on a rotator. The beads were then washed with PBS (pH 7.4), bead surface was blocked with a solution of 2% fat-free milk or 1% BSA in PBS (pH 7.4) for 1 hour. Human phage library MeganLib™ was diluted at a concentration of $2*10^{13}$ phage particles/ml in PBS (pH 7.4) with 2% fat-free milk and non-target antigen containing a target antigen tag, and preselected by magnetic beads containing no antigen on the surface, in order to remove nonspecific binding phages. IL-5Ra-coated magnetic beads were then incubated with MeganLib™ for 1-2 hours at room temperature.

Unbound phages were removed by several cycles of washing of magnetic beads with a solution of PBS (pH 7.4) containing 0.1% Tween-20™. Number of washing cycles was increased from round to round (3 washing cycles in the first round, 9 washing cycles in the second round, and 15 washing cycles in the fourth round). The phages bound to antigen on the surface of magnetic beads were eluted from beads with 100 mM Gly-HCl solution (pH 2.2) during 15 min under stirring, and then neutralized with 1M Tris™-HCl (pH 7.6). *E. coli* TG1 bacteria were infected with phages, grown in culture medium and then used in the next selection cycle. After three or four rounds, phagemid DNA was isolated from *E. coli* TG1 culture according to the manufacturer's (Qiagen™) protocol. Polyclonal phage enzyme immunoassay (ELISA) was used for enrichment of library against target antigens and assessment of presence of non-specifically binding phage particles.

Example 6

ELISA of Polyclonal Phage Against Specific and Nonspecific Antigens

Target antigen (CD47/PD-L1) and non-target one (with Fc-fusion protein) were immobilized onto high absorption plates (Greiner-Bio) in order to perform ELISA. Protein was added at a concentration of 1 μg/ml and 5 μg/ml, respectively, in 0.1 M $NaHCO_3$(pH 9.0) and titrated with an increment of 2 to 7 dilutions, sealed plates were then incubated overnight at 4° C. All subsequent steps were conducted in accordance with the standard ELISA protocol using a high-performance automated Tecan Freedom EVO 200-based robotic platform (Tecan). To block non-specific binding, blocking buffer comprising 2% fat-free milk or 1% BSA in PBS (pH 7.4) was added to plate wells. The plates were incubated for 1 h at room temperature. After several washing cycles with phosphate-saline buffer containing Tween 20™ (PBST), 50 μl/well of the test polyclonal phage was added. After washing, each well was coated (50 μl/well) with anti-M13 HRP-conjugated secondary antibody (Pierce-ThermoScientific) in PBST (1:7500). After 50 minute incubation at room temperature, plates were three times washed with PBST. The colorimetric signal was obtained by adding substrate solution ($H_2O_2$-0.02% and TMB in $CH_3COONa$ pH 5.5) for 10 minutes; color development was then blocked by adding 1% sulfuric acid (20 μl). The color signal was measured at 450 nm using a suitable Tecan-Sunrise plate reader (Tecan).

ELISA of polyclonal phage product showed significant enrichment after third and fourth rounds of selection on target antigen. Libraries were selected for recloning and further screening, in which the signal was observed to exceed 5 times at minimal dilution of phage libraries to non-homologous control antigens.

Example 7

Recloning of Genes of Antibody Fragments Into Expression Plasmid

Recloning of genes of antibody variable domains into an expression plasmid from phagemid vector after successful rounds of selection was carried out according to a standard protocol using restriction ligation technique.

The resulting pool of clones, enriched with VHH monodomains or scFv, specific against CD47 was recloned into the expression plasmid pET-22 (Novagen) under control of T7 promoter, which carries myc- and His6-tag sequences at the C-terminus of VHH. Fab genes for libraries comprising enriched sequences against CD47 antigen were recloned into the expression vector pLL4, under control of the lac promoter, further comprising myc- and His6-tag sequences at the C-terminus of the heavy chain CH1 domain.

Subsequently, expression vectors comprising antibody fragments were transformed into *E. coli* B121(DE3) Gold (Stratagene) for generation of antibody fragments by secretion into the culture medium and conducting of comparative analysis of affinity of variable antibody fragments from display libraries to antigen by ELISA using Mabnext Flow Chart platform.

Example 8. Analysis of Specific Binding of scFv or VHH Monodomain to Human CD47-Fc ELISA was used to measure the binding of specific test antibody fragments of Example 4 to human CD47-Fc. ELISA well plates (Nunc ImmunoMaxisorp™) were covered with 50 μl/well of human CD47-Fc (Biocad) (0.5 μg/ml in 1× coating carbonate buffer), sealed, and incubated overnight at 4° C. All further stages were performed in accordance with standard ELISA protocols with a high-performance automated platform based on robotic systems such as GenetixQ-pix2xt (Molecular Devices) and Tecan Freedom EVO 200 (Tecan). Non-specific binding was blocked by adding a blocking buffer BB (200 μl 0.5% fat-free milk in PBS). Plates were incubated on a shaker for 1 h at room temperature. After washing with PBS-Tween™, each cell was coated with 100 μl of cell supernatant containing the test antibody fragment. The plates were incubated on a shaker for 1 hour at room temperature; further, each plate well was 5 times washed with PBS-Tween™ buffer. After washing, mouse anti-MYC IgG clone 9E10 (ThermoFisher Scientific) (50 μl/well) was added to PBS-Tween™ (1:5000). The plates were shaken in rotation shaker (50 min at room temperature) and then 5 times washed with PBS-Tween™ buffer as described above. After washing, anti-mouse IgG HRP conjugate (ThermoFisher Scientific) (50 μl/well) was added to PBS-Tween™ (1:10000). The plates were shaken in rotation shaker (50 min at room temperature) and then 5 times washed with PBS-Tween™ buffer as described above. Colorimetric signal was obtained by adding TMB (50 μl/well) until saturated (average of 10-12 min); further color development was blocked by adding a stop solution (25 μl/well, 1% sulfuric acid). Color signal was measured at 450 nm using a suitable Tecan-Sunrise plate reader (Tecan). Antibody binding was proportional to the signal produced. Clones in which the colour signal exceeded the background signal more than 5 times were tested in a competitive ELISA assay to identify antagonistic specific antibody fragments blocking the interaction between SIRP-Fc ligand (BIOCAD) and human CD47-Fc receptor under conditions analogous to those described in [WO2016048188 A8] and under a 4-times reduced signal compared to a control that does not comprise the test antibody fragments.

Screening of 2400 clones resulted in 265 scFv and VHH clones demonstrating said 5-fold exceeding in the signal over the background. Said panel of positive clones produced 27 antagonistic clones capable of blocking the interaction between SIRP-Fc ligand (BIOCAD) and human CD47-Fc receptor. The nucleotide sequence of positive clone genes was determined by Sanger sequencing on 3130×1 Genetic Analyzer (Applied Biosystems). Six exemplary VHH monodomain clones were obtained differing in sequence by at least 1 amino acid, but having CDR regions, each at least 90% homologous to the others, thus indicating that they originated from one parental clone by virtue of in vivo maturation in an immunized llama (Table 1).

TABLE 1

Sequences of CD47-specific binding VHH monodomains to human CD47.

| Clone name | Amino acid sequence | OD units, initial screening for CD47-Fc | OD units, binding on CD47 proprietary | OD units, competitive screening to SIRP-Fc |
|---|---|---|---|---|
| BCD106-02_L.Alecto.VHHSel2_MP1_H10_78 | QVKLEESGGGLVQPG GSLRLSCAASRSISSIN AMNWYRQAPGKRRE WVAQITGEGITNYRD SVKGRFTITSDNAKNT MYLQMNSLKPEDTAV YYCNAFVIHTTSEVY WGQGTLVTVSS SEQ ID NO: 109 | 0.4 | 0.448 | 0.095 |
| BCD106-02_L.Alecto.VHHSel2_MP1_G5_37 | AVQLVDSGGGLVQPG GSLRLSCAASRSIFSIN AMNWYRQAPGNRRE WVAQITDEGITNYVD SVKGRFTITRDNAKNT MYLQMNSLKPEDTAV YYCNAFVITTTSEIYW GQGTTVTVSS SEQ ID NO: 110 | 0.166 | 0.426 | 0.143 |

TABLE 1-continued

Sequences of CD47-specific binding VHH monodomains to human CD47.

| Clone name | Amino acid sequence | OD units, initial screening for CD47-Fc | OD units, binding on CD47 proprietary | OD units, competitive screening to SIRP-Fc |
|---|---|---|---|---|
| BCD106-02_L. Alecto. VHHSel2_ MP1_ G7_53 | QVKLEESGGGLVQPG GSLTLSCAASGIISSIN AMNWYRQAPGKRRE WVAQITGEGITNCRDS WKGRFSITSDSANNT MYLQMNNLKPDDTD VYYCNAFVIHTTSEIY WGLGTTVTVSS SEQ ID NO: 111 | 0.319 | 0.498 | 0.088 |
| BCD106-02_L. Alecto. VHHSel2_ MP1_ F10_76 | DVQLVESGGGLVQPG GSLRLSCAASRNIFSIN AMNWYRQAPGKRRE WVAQITSEGITNYVDS VKGRFTITRDNAKNT MYLQMNSLKPEDTAV YYCNAFVITASSEVY WGQGTTVTVSS SEQ ID NO: 112 | 0.213 | 0.312 | 0.114 |
| BCD106-02_L. Alecto. VHHSel2_ MP1_ C7_49 | AVQLVDSGGGLVQPG GSLRLSCAASRSIFSIN AMNWYRQAPGNRRE WVAQITDEGITNYVD SVKGRFTITRDNAKNT MYLQMNSLKPEDTAV YYCNAFVITTTSEIYW GQGTTVTVSS SEQ ID NO: 113 | 0.127 | 0.379 | 0.14 |
| BCD106-02_L. Alecto. VHHSel2_ MP1_ B9_64 | DVQLVESGGGLVQPG GSLTLSCAASRNIFRIN AMNWYRQAPGKRRE WVAPITSEGITNYVDS VKGRFTITRDNAKNT MYLQMNSLKPEDTAV YYCNACLITASSEVY WGQGTLVTVSS SEQ ID NO: 114 | 0.129 | 0.24 | 0.188 |
| Negative control antigen + conjugate | — | 0.021 | 0.024 | 0.481 |

Example 9

Analysis of Specific Binding of Fabs to Human CD47-Fc

Fab production was produced according to the standard technique: bacterial cells were transformed with expression vectors containing Fab genes, and subsequent addition of inducer, which triggers transcription of lac operon, in the medium, during culturing resulting transformants, causes expression of Fabs.

ELISA was then conducted to search for Fabs binding human CD47.

B6H12 Fab with a published sequence (see Example 1) was used as a positive control. To test specific binding, ELISA well plates (medium binding, Greiner bio one) were covered with 50 µl/well of CD47 Fc lama (0.2 µg/ml in 1× carbonate buffer), sealed and incubated overnight at 4° C. All further stages were performed in accordance with standard ELISA protocols with a high-performance automated platform based on robotic systems such as Genetix Qpix2xt (Molecular Devices) and Tecan Freedom EVO 200 (Tecan). Non-specific binding was blocked by adding a blocking buffer BB (200 µl 0.5% fat-free milk in PBS). The plates were incubated for 1 h at room temperature. After washing with PBS-Tween™, each cell was coated with 60 µl/well of cell supernatant containing the test Fab. Plates were incubated for 1 hour at room temperature; each plate well was then 3 times washed with PBS-Tween™ buffer. After washing, each well was coated (50 µl/well) with anti-human Fab HRP-conjugated secondary antibody (Pierce-ThermoScientific) in PBS-Tween™ (1:7500). The plates were incubated for 1 hour at room temperature and three times washed with PBS-Tween™ buffer, as described above. Colorimetric signal was obtained by adding TMB (50 µl/well) until saturated (15 min); further color development was blocked by adding a stop solution (25 µl/well, 1% sulfuric acid). Color signal was measured at 450 nm using a suitable Tecan-Sunrise plate reader (Tecan). Antibody binding was proportional to the signal produced. Clones in which a colour signal exceeded the signal from control antibody were tested by ELISA against non-specific binding.

Example 10

Analysis of Non-Specific Binding of Fabs to Various Human Antigens

Secondary screening is aimed at selecting Fab-producing clones that interact with the full-length CD47 antigen and do not interact with non-specific antigens, and also compete with the ligand (CD47) for binding to SIRPa.

ELISA was used to analyse non-specific binding of the test Fabs to other antigens. Analysis was performed as described above, but 3DHer3-H6E, INFα2b, PD-L1-Fc-lama (2.5 µg/ml in 1× carbonate buffer) were used as antigens for immobilization. CD47 FE and CD47 Fc lama (0.2 µg/ml in 1× carbonate buffer) were used as specific binding controls. All further stages were conducted in accordance with the standard ELISA protocol with a high-performance automated platform based on robotic systems such as Genetix Qpix2xt (Molecular Device) and Tecan Freedom EVO 200 (Tecan).

Competitive ELISA was used to test pre-selected anti-human CD47 specific Fabs on the ability to block interaction with the SIRPα receptor. Fab with a published sequence (see Example 1) was used as a positive control of the antagonist.

ELISA well plates (high binding, Greiner bio one) were covered with 50 µl/well of SIRPa (0.5 µg/ml in 1× carbonate buffer) and incubated overnight at 4° C. All further stages were performed in accordance with standard ELISA protocols with a high-performance automated platform based on robotic systems such as Genetix Qpix2xt (Molecular Devices) and Tecan Freedom EVO 200 (Tecan). Non-specific binding was blocked by adding a blocking buffer BB (200 µl 0.5% fat-free milk in PBS). Th plates were incubated for 1 h at room temperature.

In parallel, cell supernatant comprising the test Fab and CD47 Fc lama (at a final concentration of 1 µg/ml in PBS-Tween™) was mixed at a 1:1 ratio in non-absorbent plates, incubated for 45 minutes at room temperature.

After washing the SIRPa receptor-containing plate to remove BB, a mixture of Fab and CD47 Fc lama was transferred to the plate, incubated for 45 minutes at room temperature. Each plate well was then three times washed with PBS-Tween™ buffer, 50 µl/well of anti-human Fab HRP-conjugated secondary antibody (Pierce-ThermoScientific) was added to PBS-Tween™ (1:7500). The plates were incubated for 45 min at room temperature and 3 times washed with PBS-Tween™, as described above. Colorimetric signal was obtained by adding TMB (50 µl/well) until saturated (average of 15 min); further color development was blocked by adding a stop solution (25 µl/well, 1% sulfuric acid). Color signal was measured at 450 nm using a suitable Tecan-Sunrise plate reader (Tecan). Fab binding was inversely proportional to the colour signal produced. Clones that showed blocking at the level of the control Fab were noted as positive and used in further assays. The genes of variable domains of positive clones were sequenced according to standard protocols on Applied Biosystems 3130 Genetic Analyzer (Applied Biosystems) and analyzed.

Example 11

Comparative Screening of Anti-CD47 Antibody Fragments by the Kinetic Dissociation Constant koff (kdis)

VHH antibody fragments were measured to provide an example of analysis of kinetic parameters of interaction of antibody fragments that specifically bind to CD47 receptor. Dissociation constant ($k_{dis}$)-based comparative screening for VHH fragments was performed using Octet Red 96 and ARG2 amino-reactive biosensors (Pall-ForteBio). Affinity constants can be calculated based on the exact protein concentration in the test solution, and, since cell growth media were used as a protein solution and protein concentrations were not measured, the candidates were compared to each other by using the dissociation constant thereof. Biosensors were pre-rehydrated for an hour in water. After activating biosensors, CD47-Fc at a concentration of 10 µg/ml in acetate buffer pH4 was non-specifically (by NH2 groups) immobilized onto the biosensor. The sensors were then immersed into wells containing cell growth medium with specific VHHs (from about 1 µg of VHH in 1 ml of medium), where the complex was associated. The sensors were then immersed in a buffer solution, where the subsequent stage of dissociation of the complex took place. 1/10 of the volume of 10× working buffer was added to the test specimens in E. Coli growth medium containing anti-CD47 VHH fragments. The obtained curves were analyzed using OctetDataAnalysis (version 7.0) according to the standard procedure with 1:1 interaction model.

The results of koff screening of anti-CD47 VHH candidates are shown in Table 2. Specific binding of all VHH fragments to human CD47 was demonstrated; candidate BCD106-02_L.Alecto.VHHSel2_MP1_C7_49 was selected based on predominant kdis for further study and recloning to obtain bispecific antibodies.

TABLE 2

Kinetic dissociation constants of VHH with CD47-Fc

| No | Clone name | kdis1l/s) |
|----|---|---|
| 1 | BCD106-02_L.Alecto.VHHSel2_MP1_B9_64 | 8.00E-03 |
| 2 | BCD106-02_L.Alecto.VHHSel2_MP1_C7_49 | 5.00E-03 |
| 3 | BCD106-02_L.Alecto.VHHSel2_MP1_F10_76 | 1.00E-02 |
| 4 | BCD106-02_L.Alecto.VHHSel2_MP1_G5_37 | 6.00E-03 |
| 5 | BCD106-02_L.Alecto.VHHSel2_MP1_G7_53 | 8.00E-03 |
| 6 | BCD106-02_L.Alecto.VHHSel2_MP1_H10_78 | 6.00E-03 |
| 7 | BCD106-02_L.Alecto.VHHSel2_MP1_B9_64 | 8.00E-03 |

Example 12

Figure 7:
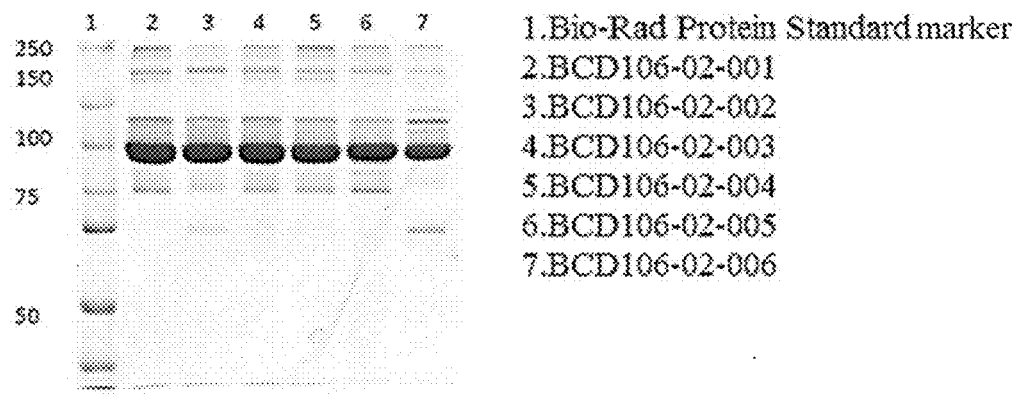
FIG. 7. SDS-gel electrophoresis in non-reducing conditions of anti-PD-L1/anti-CD47 preparations of bispecific antibodies based on anti-CD47 scFv fragments.
Figure 8:
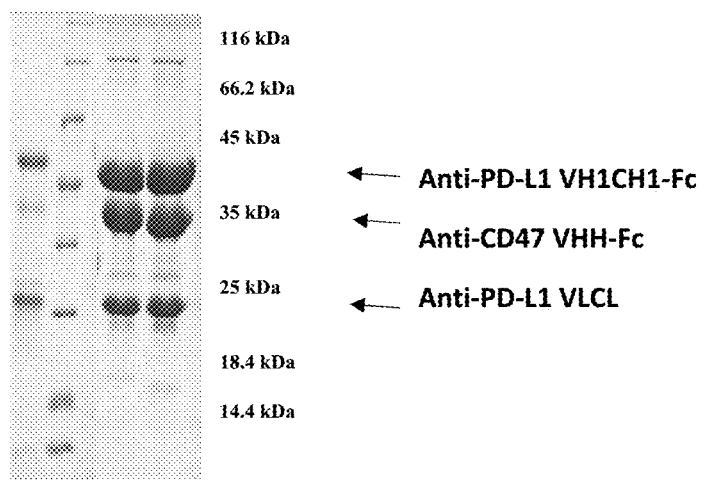
FIG. 8. SDS-gel electrophoresis in reducing conditions of preparations of anti-PD-L1/anti-CD47 bispecific antibodies based on anti-CD47 VHH fragments.

Obtaining Constructs and Production of Asymmetric Bispecific Anti-CD47/PD-L1 Antibodies The sequences of all variable domains of optimized scFv fragments, and the sequences of genes for the synthesis of wild-type and mutant variants of the variable domain VHH of candidate BCD106-02-VHH_C7-49 (Table 3) and the genes of variable domains of light and heavy chains of anti-PD-L1 antibody (BCD135, original human antibody from BIOCAD) were obtained de novo by calculation using proprietary computer algorithms and PCR synthesis from oligonucleotides obtained on ASM-2000 (Novosibirsk) synthesizers according to the standard protocol. Long scFv genes were derived from VH and VL genes by using two-step PCR synthesis from single-stranded DNA molecules. After PCR synthesis, DNA fragments fractionated on agarose gel were purified on QIAquick™ Gel Extraction Kit (Qiagen™) columns. The scFv and VHH genes were individually ligated into plasmid pEE-Fc(knob), whereas the variable heavy chain domain of aPD-L1-specific antibody was individually ligated into plasmid pEE-Fc(hole). pEE- Fc(knob) contains human IgG1 Fc with mutations S354C+T366W, and pEE-Fc(hole) contains human IgG1 Fc with mutations Y349C+T366S+L368A providing heterodimerization of these Fc portions with each other, under a minimum degree of homodimerization [Nat Biotechnol. 1998 July; 16(7):677-81.], with co-transient expression in CHO-EBNA cells with the aPD-L1 light chain variable domain, analogously cloned into pEE-Clambda. After ligation-independent cloning by a modified LIC method [Aslanidis C, de Jong PI Ligation-independent cloning of PCR products (LIC-PCR). Nucleic Acids Res. 1990;18:6069-6074]), DNA was transformed into E. coli. Constructs with correct sequences pEE-Fc(knob)-scFv or pEE-Fc(knob)-VHH were co-transfected with pEE-BCD135-VH-299P-HC-hole and pEE-BCD135-01 4LG VL hzau CL to obtain the so-called asymmetric bispecific antibodies (see FIG. 6). The figure shows schematic models of asymmetric bispecific antibodies, A-based on anti-CD47 scFv and anti-PD-L1 Fab binding fragments, B-based on anti-CD47 VHH and anti-PD-L1 Fab binding fragments. The resulting genetic constructs were used for producing proteins in the CHO-T cell line, according to Example 2. After purification, the antibodies were highly homogeneous in composition, the production yields of bispecific antibodies ranged from 60 to 260 mg/ml of culture medium. FIG. 7 shows examples of purified bispecific antibodies based on anti-CD47 scFv fragments. FIG. 8 shows examples of purified bispecific antibodies based on anti-CD47 VHH fragments. The antibody variant containing the sequence VHH47Opt3 indicated in Table 3 generated an extremely low antibody yield and was excluded from further tests.

Table 3. Amino acid sequence of wild-type/mutant variants of anti-CD47 VHH from BCD106-02-VHH_C7_49 clone and variable domains of anti-PD-L1 BCD135. Gray indicates anti-CD47 VHH positions with mutations other than those of the wild type.

TABLE 3

Amino acid sequences of wild-type/mutant variants of anti-CD47 VHH from BCD106-02-VHH_C7_49 clone and variable domains of anti-PD-L1 BCD135. Gray indicates anti-CD47 VHH positions with mutations other than those of the wild type.

| Name | Amino acid sequences of anti-CD47-VHH variable domain |
|---|---|
| Wild VHH47 | SEQ ID NO: 115<br>AVQLVDSGGGLVQPGGSLRLSCAASRSIFSINAMNWYRQPPGNRR<br>EWVAQITDEGITNYVDSVKGRFTITRDNAKNTMYLQMNSLKPEDTA<br>VYYCNAFVITTTSEIYWGQGTTVTVSS |
| VHH47Opt1 | SEQ ID NO: 116<br>AVQLVDSGGGLVQPGGSLRLSCAASRSIFSINAMNWYRQAPGKGT<br>EWVAQITDEGITNYVDSVKGRFTITRDNAKNTMYLQMNSLKPEDTA<br>VYYCNAFVITTTSEIYWGQGTTVTVSS |
| VHH47Opt2 | SEQ ID NO: 117<br>QVQLVESGGGLVQPGGSLRLSCAASRSIFSINAMNWYRQAPGKGT<br>EWVAQITDEGITNYVDSVKGRFTISRDNAKNTLYLQMNSLRAEDTA<br>VYYCNAFVITTTSEIYWGQGTTVTVSS |
| VHH47Opt3 | SEQ ID NO: 118<br>QVQLVESDGGLVQPGGSLRLSCAASRFTFSINAMNWVRQAPGKGL<br>EWVSQITDEGITNYVDSVKGRFTISRDNAKNTLYLQMNSLRAEDTA<br>VYYCAAFVITTTSEIYWGQGTLVTVSS |
| | Amino acid sequences of anti-PD-L1 variable domains |
| VH(BCD135) | SEQ ID NO: 119<br>EVQLVESGGGVVRPGGSLRLSCAASGFTFDDYAMSWVRQAPGKGL<br>EWVSDISWSGSNTNYADSVKGRFTISRDNAKNSLYLQMNSLRAED<br>TALYHCARAPLLLAMTFGVGSWGQGTLVTVSS |
| VL(BCD135) | SEQ ID NO: 120<br>QTVVTQEPSLSVSPGGTVTLTCGLSSGTVTAINYPGWYQQTPGQAP<br>RTLIYNTNTRHSGVPDRFSGSISGNKAALTITGAQAEDEADYYCALY<br>MGNGGHMFGGGTKLTVL |

Example 13. Analysis of Interaction of Anti-PD-L1/Anti-CD47 PD-L1-Bispecific Antibodies with Human PD-L1/CD47 Antigens on OctetRED96™

Analysis of interaction of PD-L1-bispecific antibodies with human PD-L1/CD47 antigens was performed on Octet-tRed 96™ (Pall-ForteBio™). AR2G biosensors were pre-rehydrated for an hour in mQ. After activating biosensors, PD-L1-Fc or CD47-Fc at a concentration of 25 μg/ml in acetate buffer pH4 were nonspecifically (by NH2 groups) immobilized onto the biosensor. The sensors were then immersed in wells containing anti-PD-L1/anti-CD47 antibody solutions (10 μg/ml), where the antibody-antigen complex was associated. The sensors were then immersed in a buffer solution for a subsequent dissociation step. Binding curves, after subtracting a reference signal, were analyzed using Octet Data Analysis™ software (Version 8.2) in accordance with the standard procedure and using 1:1 interaction model.

The results of analyzes are shown in Table 4. Thus, one may conclude that the antibodies have high affinity, where affinity to the PD-L1 antigen in antibodies of this format has nM values, whereas the affinity to the CD47 antigen has subnM values. Such binding is considered sufficient for the antibody to be able to interact with receptors on target cells, for subsequent testing both in vitro and in vivo therapeutic activity.

TABLE 4

Kinetic dissociation constants of anti-CD47/anti-PD-L1 bispecific antibodies.

| Candidate name | Response (CD47 FcL) | kD (M) (CD47 FcL) | kon(1/Ms) (CD47 FcL) | kdis(1/s) (CD47 FcL) | Response (PD-L1-Fc human) | kD (M) (PD-L1-Fc human) | kon(1/Ms) (PD-L1-Fc human) | kdis(1/s) (PD-L1-Fc human) |
|---|---|---|---|---|---|---|---|---|
| BCD106-02-001 | 0.7313 | 1.45E−08 | 9.88E+04 | 1.43E−03 | 3.1828 | 1.35E−09 | 3.24E+05 | 4.38E−04 |
| BCD106-02-002 | 0.412 | 4.59E−08 | 1.4100E+05 | 6.44E−03 | 3.0283 | 1.24E−09 | 3.65E+05 | 4.52E−04 |
| BCD106-02-003 | 0.4481 | 2.90E−08 | 1.65E+05 | 4.77E−03 | 3.1756 | 1.21E−09 | 3.71E+05 | 4.50E−04 |
| BCD106-02-004 | 0.4398 | 3.09E−08 | 1.60E+05 | 4.93E−03 | 3.0586 | 1.30E−09 | 3.55E+05 | 4.61E−04 |
| BCD106-02-005 | 0.413 | 1.77E−08 | 1.53E+05 | 2.70E−03 | 3.0494 | 1.31E−09 | 3.35E+05 | 4.40E−04 |
| BCD106-02-006 | 1.2762 | 5.81E−10 | 2.73E+05 | 1.58E−04 | 2.9262 | 1.04E−09 | 3.98E+05 | 4.14E−04 |
| BCD106-02-013 | 0.7682 | 5.88E−10 | 1.13E+06 | 6.62E−04 | 2.6744 | .75E−09 | 2.38E+05 | 4.16E−04 |
| PD-L1-VHH-VHH47O pt1 | 0.0882 | 4.65E−09 | 6.66E+04 | 3.10E−04 | 0.1621 | 6.90E−10 | 1.17E+06 | 8.09E−04 |
| PD-L1-VHH-VHH47O pt2 | 0.2332 | 3.65E−09 | 8.02E+04 | 2.93E−04 | 0.175 | 7.64E−10 | 1.09E+06 | 8.36E−04 |

Example 14

Analysis of Interactions of Anti-PD-L1/Anti-CD47 Bispecific Antibodies with Cynomolgus Monkey CD47 and PD-L1 Receptors on Forte Bio Octet RED 384

Experimental study of antibody affinity to animal CD47/PD-L1 antigens was performed on Forte Bio Octert RED 384. Antibodies at a concentration of 20 µg/ml were immobilized onto AR2G sensors (Forte Bio) according to the standard protocol and manufacturer's instructions. Analysis was conducted at 30° C. using PBS comprising 0.1% Tween 20 and 0.1% BSA as a working buffer. After baseline recording, the sensors were immersed into wells containing antigen solution (animal CD47, and PD-L1) for 300 seconds, where the complex was associated. Complex dissociation in buffer solution was then detected for 600 seconds.

The binding curves, after subtracting a reference signal, were analyzed using Octet Data Analysis (Version 9.0) software in accordance with the standard procedure and using 1:1 Global interaction model. Anti-CD47 antibodies specifically bind to cynomolgus monkey antigen CD47 and PD-L1. Table 5 and Table 6.

TABLE 5

Kinetic values of interaction of antibodies against cynomolgus monkey antigen (CD-47).

| Name | KD (M) | KD Error | kon(1/Ms) | kon Error | kdis(1/s) | kdis Error |
|---|---|---|---|---|---|---|
| BCD106-02-001 | 6.32E−09 | 3.69E−11 | 1.88E+05 | 9.64E+02 | 1.18E−03 | 3.28E−06 |
| BCD106-02-006 | 6.99E−10 | 3.99E−12 | 8.64E+05 | 3.61E+03 | 6.04E−04 | 2.34E−06 |
| BCD106-02-013 | 3.06E−10 | 3.56E−11 | 5.31E+04 | 1.60E+02 | 1.63E−05 | 1.89E−06 |

TABLE 6

Kinetic values of interaction of antibodies to cynomolgus monkey antigen (PD-L1).

| Name | KD (M) | KD Error | kon(1/Ms) | kon Error | kdis(1/s) | kdis Error |
|---|---|---|---|---|---|---|
| BCD106-02-001 | 8.75E−10 | 6.01E−12 | 1.67E+06 | 1.07E+04 | 1.46E−03 | 3.55E−06 |
| BCD106-02-006 | 7.27E−10 | 6.40E−12 | 1.73E+06 | 1.34E+04 | 1.26E−03 | 5.25E−06 |
| BCD106-02-013 | 1.34E−09 | 1.02E−11 | 1.65E+06 | 1.19E+04 | 2.21E−03 | 5.66E−06 |

Example 15

Analysis of Non-Specific Binding of Anti-PD-L1/anti-CD47 Bispecific Antibodies to an Antigen Panel on Forte Bio Octet RED 384

Experimental study of nonspecific binding was performed on a panel of non-specific his-tagged antigens. Anti-hIgG Fc Capture (AHC) biosensors pre-rehydrated for 10 minutes in PBS containing 0.1% Tween-20™ and 0.1% BSA as a working buffer were used for the measurements.

Antibodies at a concentration of 30 µg/ml were immobilized onto Anti-hIgG Fc Capture (AHC) sensors (Forte Bio). The analysis was conducted at 30° C. using PBS comprising 0.1% Tween 20™ and 0.1% BSA as a working buffer. After the baseline was prescribed in the buffer solution, the sensors were immersed in the wells with a solution of non-specific antigens for 300 seconds, where the complex was associated. Then the dissociation of the complex in the buffer solution was detected for 600 seconds.

The binding curves (after subtracting a reference signal) were analyzed using OctetDataAnalysis (version 9.0) according to the standard procedure using 1:1 Global interaction model. anti-PD-L1/anti-CD47 bispecific antibodies do not non-specifically bind to the panel of antigens.

Example 16

Analysis of Interaction of Anti-PD-L1/Anti-CD47 Bispecific Antibodies with a FcγRIIIa Panel on Forte Bio Octet RED 384

Experimental study of antibody affinity to the panel of Fc-binding proteins was performed on Forte Bio Octert RED 384 using streptavidin (SAX) biosensors pre-hydrated for 30 minutes in PBS containing 0.1% Tween-20™ and 0.1% BSA.

Biotinylated Fc-binding Avi-tagged proteins FcγRIIIa-F158 and FcγRIIIa-V158 at a concentration of 5 µg/ml in FSB kinetic buffer containing 0.1% Tween-20™ and 0.1% BSA pH 7.4 were immobilized onto streptavidin (SAX) sensors, with fixation of $t_{RecLoad\_}$ time necessary to achieve a signal level of 0.4 nm. After baseline recording, the sensors were immersed into wells containing antibody solution for 60 seconds, where the complex was associated. The complex dissociation in buffer solution was then detected for 150 seconds.

The binding curves (after subtracting a reference signal) were analyzed using OctetDataAnalysis (version 9.0) according to the standard procedure using 2:1 Global interaction model. anti-PD-L1/anti-CD47 bispecific antibodies specifically bind to Fc-binding proteins FcγRIIIa-F158 and FcγRIIIa-V158. Table 7 and Table 8.

TABLE 7

Kinetic values of interaction of antibodies BCD-106 (02-001, 03-006, 02-013) against FcγRIIIa-F158.

| Name | KD (M) | KD Error | kdis(1/s) | kdis Error | kon(1/Ms) | kon Error |
|---|---|---|---|---|---|---|
| BCD106-02-001 | 1.61E−06 | 9.86E−07 | 6.27E−08 | 1.04E−07 | 1.73E+05 | 1.19E+04 |
| BCD106-02-006 | 1.47E−06 | 1.73E−07 | 6.03E−08 | 8.40E−08 | 1.35E+05 | 1.67E+04 |
| BCD106-02-013 | 1.30E−06 | 2.00E−06 | 3.79E−08 | 1.88E−07 | 2.22E+05 | 1.55E+04 |

TABLE 8

Kinetic values of interaction of antibodies BCD-106 (02-001, 03-006, 02-013) against FcγRIIIa-V158.

| Name | KD (M) | KD Error | kdis(1/s) | kdis Error | kon(1/Ms) | kon Error |
|---|---|---|---|---|---|---|
| BCD106-02-001 | 9.32E−07 | 1.62E−07 | 2.86E−08 | 1.86E−08 | 2.33E+05 | 5.72E+04 |
| BCD106-02-006 | 4.63E−06 | <1.0E−12 | 1.07E−06 | 5.25E−07 | 4.75E+04 | 8.58E+03 |
| BCD106-02-013 | 3.73E−07 | 1.45E−07 | 1.83E−09 | 1.07E−08 | 6.10E+05 | 5.77E+04 |

Example 17

Analysis of Interaction of Anti-PD-L1/Anti-CD47 Bispecific Antibodies with a FcRn on Forte Bio Octet RED 384

Experimental study of antibody affinity to the panel of Fc-binding proteins was performed on Forte Bio Octert RED 384 using streptavidin (SAX) biosensors pre-hydrated for 30 minutes in PBS containing 0.1% Tween-20™ and 0.1% BSA.

Biotinylated Avi-tagged FcRn at a concentration of 5 µg/ml in PBS kinetic buffer containing 0.1% Tween-20™ pH 6 was immobilized onto streptavidin (SAX) sensors, with fixation of $t_{RecLoad\_}$ time necessary to achieve a signal level of 0.4 nm. After baseline recording in buffer solution, the sensors were immersed into wells containing antibody solution in PBS kinetic buffer containing 0.1% Tween-20™ pH 6 for 60 seconds, where the complex was associated. Dissociation of the complex in PBS kinetic buffer containing 0.1% Tween-20™ and 0.1% BSA pH 7.4 was then detected for 150 seconds.

The binding curves (after subtracting a reference signal) were analyzed using OctetDataAnalysis (version 9.0) according to the standard procedure using 2:1 Global interaction model. anti-PD-L1/anti-CD47 bispecific antibodies specifically bind to FcRn. Table 9.

TABLE 9

Kinetic values of interaction of antibodies BCD-106 (02-001, 03-006, 02-013) against FcRn.

| Name | KD (M) | KD Error | kdis(1/s) | kdis Error | kon(1/Ms) | kon Error |
|---|---|---|---|---|---|---|
| BCD106-02-001 | 1.61E−06 | 9.86E−07 | 6.27E−08 | 1.04E−07 | 1.73E+05 | 1.19E+04 |
| BCD106-02-006 | 1.47E−06 | 1.73E−07 | 6.03E−08 | 8.40E−08 | 1.35E+05 | 1.67E+04 |
| BCD106-02-013 | 1.30E−06 | 2.00E−06 | 3.79E−08 | 1.88E−07 | 2.22E+05 | 1.55E+04 |

Example 18

Analysis of Ability of Anti-PD-L1/anti-CD47 Bispecific Antibodies PD-L1 to Induce Antibody-Dependent Cellular Cytotoxicity on PD-L1/CD47 Positive Cells In order to perform ADCC (antibody-dependent cellular cytotoxicity), MDA-MB-231 cell line expressing PD-L1/CD47 receptors on its surface, and peripheral blood mononuclear cells (PBMCs) were used.

Obtaining Peripheral Blood Mononuclear Cells

PBMCs were obtained by fractionating venous blood cells from healthy donors in a density gradient. After isolation, the cells were cultured in RPMI-1640 medium containing 10% FBS at a concentration of 2-5×10$^6$ cells/ml for 18-24 hours at 37° C. and 5% $CO_2$.

Preparation of Target Cells

MDA-MB-231 cells were cultured in DMEM medium containing 10% FBS (fetal bovine serum) at 37° C. and 5% $CO_2$. Cells were removed from the plastic surface using trypsin, and resuspended in DMEM containing 10% FBS. Calcein AM was added to a concentration of 5 µM. After 30 minutes, the cells were twice washed from excess Calcein AM with DMEM containing 10% FBS. A suspension of target cells at a concentration of 10$^5$ cells/ml was prepared in DMEM containing 10% FBS.

Preparation of Dilutions of Test Antibodies

All test antibodies were diluted with DMEM medium containing 10% FBS to a concentration of 10 µg/ml. A series of serial dilutions with an increment of 5 was prepared. The concentrations of the test antibodies were (ng/ml): 10000; 2000; 400; 80; 16; 3.2; 0.64; 0.128; 0.0256; 0.

Preparation of PBMC

Mononuclear lymphocytes were collected from vials, and centrifuged under 200×g for 5 minutes. A suspension of cells at a concentration of 5×10$^6$ cells/ml was prepared in DMEM medium containing 10% FBS.

Conducting ADCC Assay

50 µl/well of the test antibodies were added to wells of a 96-well plate. 100 µl/well of the target cell suspension was added to the wells containing the antibodies. The plate was Incubated at 37° C. and 5% $CO_2$ for 15-20 minutes. 50 µl/well of PBMC suspension was added to the wells containing the antibodies and target cells. 50 µl/well of DMEM medium containing 10% FBS, 100 µl of target cell suspension and 50 µl of PBMC suspension were added to three wells (a control of maximum lysis, "KL"). The plate was Incubated at 37° C. and 5% $CO_2$ for 3.5-4 hours. 30 minutes before the end of incubation, lysis buffer was added to the KL wells.

After incubation, the plates were centrifuged under 200×g for 10 minutes. Supernatant fluid was transferred to new 96-well plates. Fluorescence was measured in relative fluorescence units at excitation/emission wavelength of 485/538 nm by using a plate fluorimeter.

ADCC efficacy was calculated by the formula:

$$ADCC\ (\%) = \frac{\text{The value of luminescence in the hole } (RLU) - \text{The average value, } K\ (RLU)}{\text{Average value } KL\ (RLU) - \text{Average Value } K\ (RLU)} \cdot 100,$$

where

K—control of spontaneous lysis of target cells in the presence of effector cells (50 µl/well of DMEM medium containing 10% FBS+100 µl/well of target cells+50 µl/well of PBMC)

KL—control of maximum lysis of target cells (50 µl/well of DMEM medium containing 10% FBS+100 µl/well of target cells+50 µl/well of PBMCs+lysis buffer).

Figure 9:
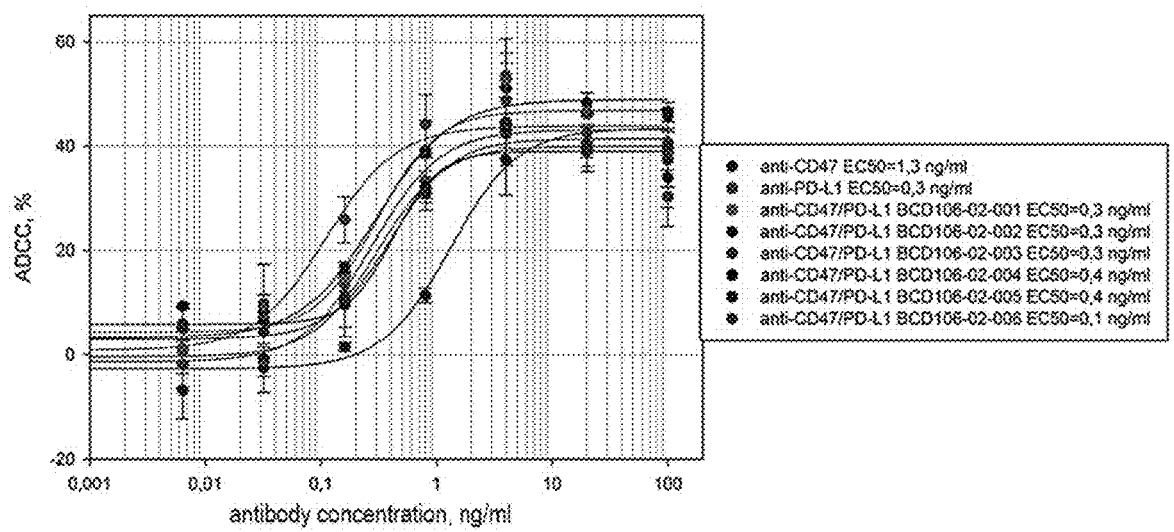
FIG. 9. The dependence of the cytotoxic effect on the concentration of the anti-PD-L1/anti-CD47 bispecific antibodies studied FIG. 10. Dependence of cytotoxic effect on the concentration of anti-PD-L1/anti-CD47 bispecific antibodies studied.
Figure 10:
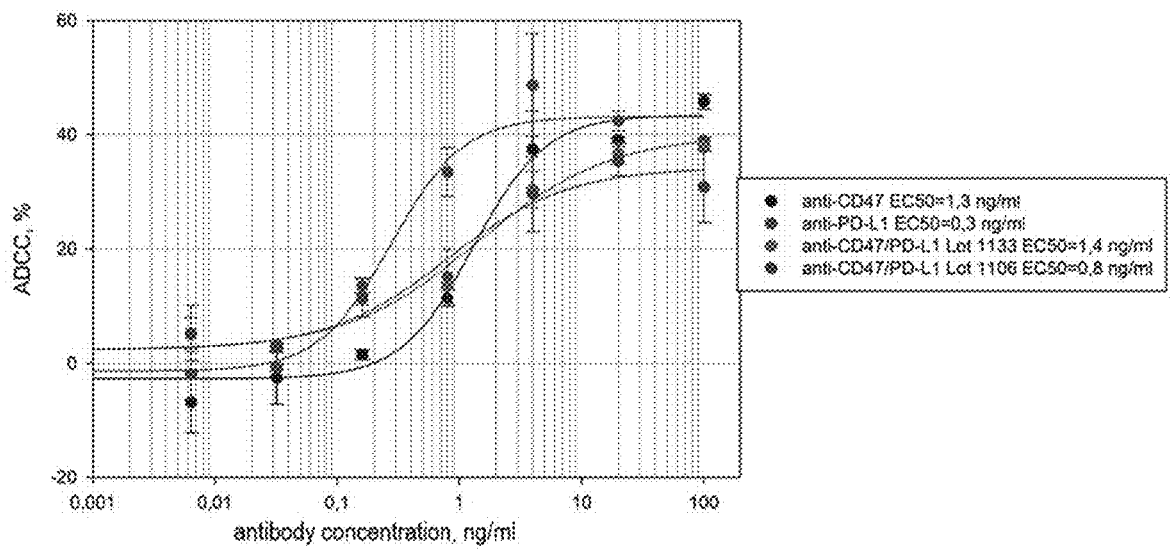

The results are shown in FIGS. 9 and 10.

According to the data obtained, all anti-CD47/PD-L1 antibodies show EC50 values that are comparable to or exceeding those of a control monospecific anti-CD47 antibody (clone B6H12).

Example 19

Comparison of Activity of Anti-PD-L1/Anti-CD47 Bispecific Antibodies Against CD47/PD-L1 in a Test on Stimulation of Phagocytosis by Human Macrophage Cells In order to perform ADCP (Antibody-Dependent Cellular Phagocytosis), MDA-MB-231 cell line having PD-L1/CD47 receptors on its surface, and human macrophage cells were used.

Obtaining Human Macrophages

Peripheral blood mononuclear cells (PBMCs) were isolated from the venous blood of healthy donors by density gradient separation. Human blood monocytes were isolated using a kit for isolating a fraction of human CD14-positive human cells (Miltenyi Biotec). Wells of a 24-well plate were used to culture 350,000 monocytes/well in 700 µl of RPMI-1640 containing 10% FBS, 100 ng/ml of GM-CSF (Peprotech) at 37° C. and 5% $CO_2$ for 3 days. On the 4th day of culture, the medium was replaced with a new medium containing 700 µl of RPMI-1640 containing 10% FBS, 100 ng/ml GM-CSF (Peprotech), 50 ng/ml of IFNγ (Peprotech) and 10 ng/ml of LPS (Sigma) per well, cells were cultured at 37° C. and 5% $CO_2$ for another 3 days.

Preparation of Target Cells

MDA-MB-231 cells were cultured in DMEM medium containing 10% FBS (fetal bovine serum) at 37° C. and 5% $CO_2$. Cells were removed from the plastic surface by trypsin, and resuspended in DMEM containing 10% FBS. Calcein AM was added to a concentration of 5 μM. After 30 minutes, the cells were twice washed from excess Calcein AM with DMEM containing 10% FBS. A suspension of target cells at a concentration of $10^5$ cells/ml was prepared in DMEM containing 10% FBS.

Conducting ADCP Assay

Medium was selected from plate wells containing macrophages, 500 μl of RPMI-1640 medium containing 10% FBS and 20 μg/ml of the test antibodies was added to the wells. 500 μl/well of the target cell suspension was added to the wells. The plate was Incubated at 37° C. and 5% $CO_2$ for 3 hours. Medium was then selected, the cells were removed from the plastic surface by TrypLE Express reagent, and stained with fluorescently-labeled anti-CD14 antibodies. The suspension of stained cells was analyzed on a flow cytofluorometer.

ADCP efficacy was calculated by the formula:

$$ADCP\text{ efficacy} = \frac{\text{Calcein}^+ \, CD14^+}{CD14^+} \times 100\%,$$

where

Calcein$^+$ CD14$^+$ is the number of CD14-positive cells containing calcein dye.

CD14$^+$ is the number of all CD14-positive cells

Figure 11:
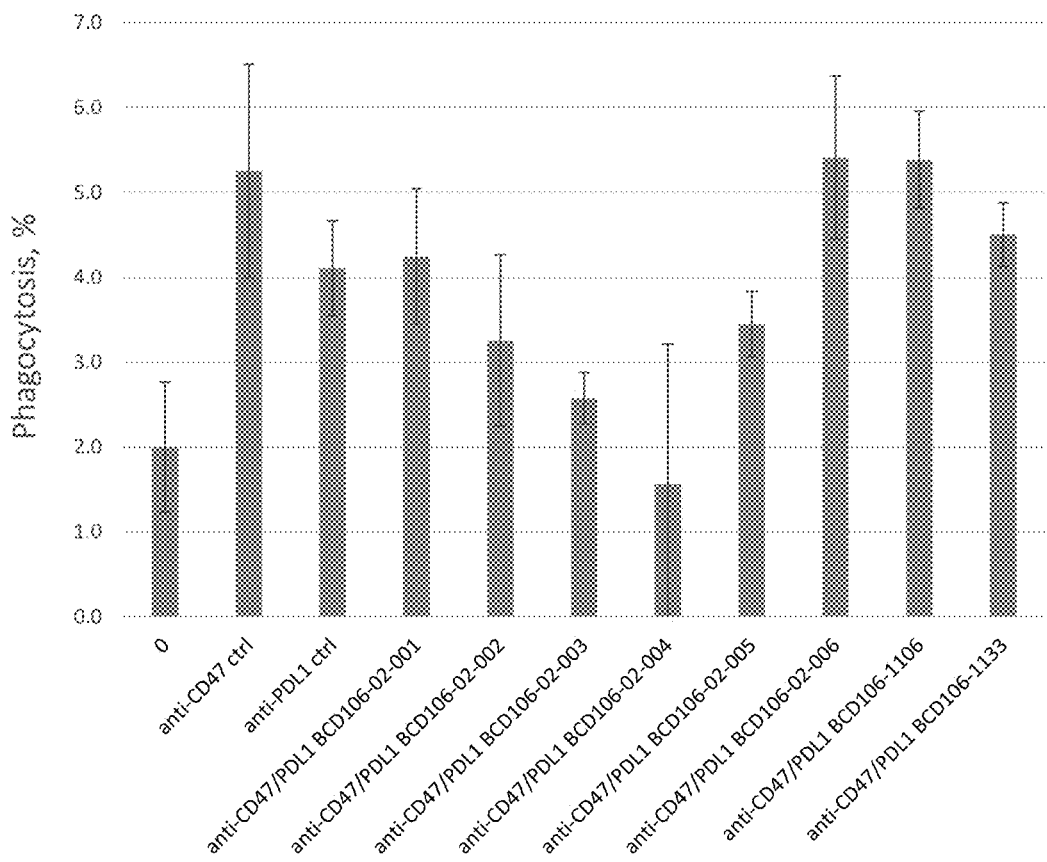
FIG. 11. Efficacy of phagocytosis of MDA-MB-231 cell lines by human macrophages in the presence of anti-PD-L1/anti-CD47 bispecific antibodies.
Figure 12:
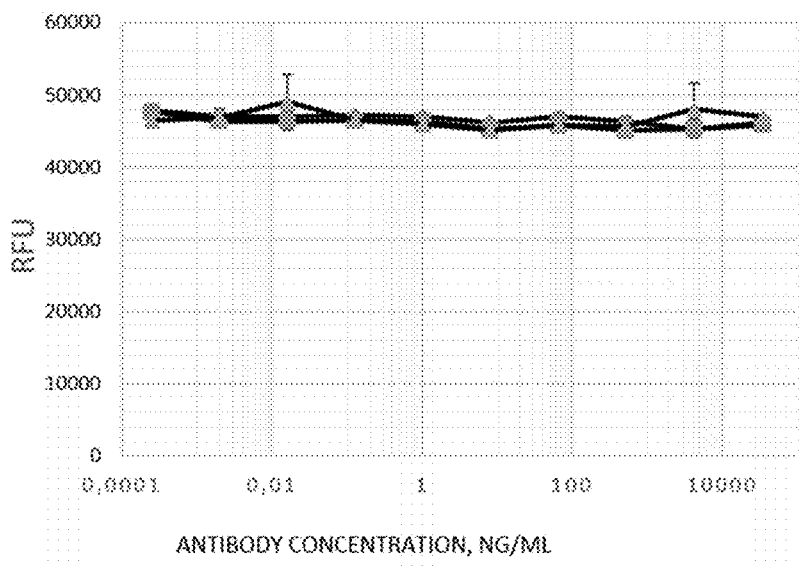
FIG. 12. Dependence of the level of fluorescence on the concentration of anti-PD-L1/anti-CD47 bispecific antibodies.
Figure 13:
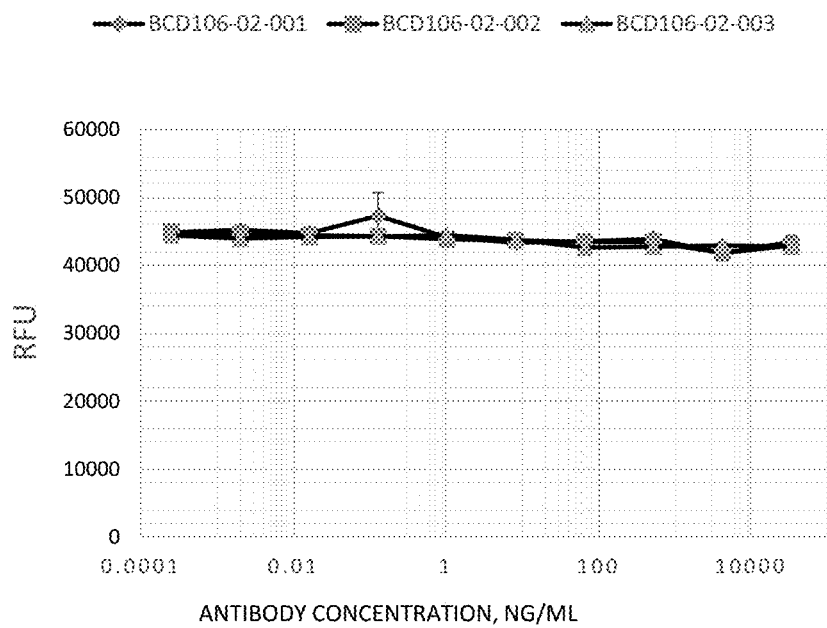
FIG. 13. Dependence of the level of fluorescence on the concentration of anti-PD-L1/anti-CD47 bispecific antibodies.
Figure 14:
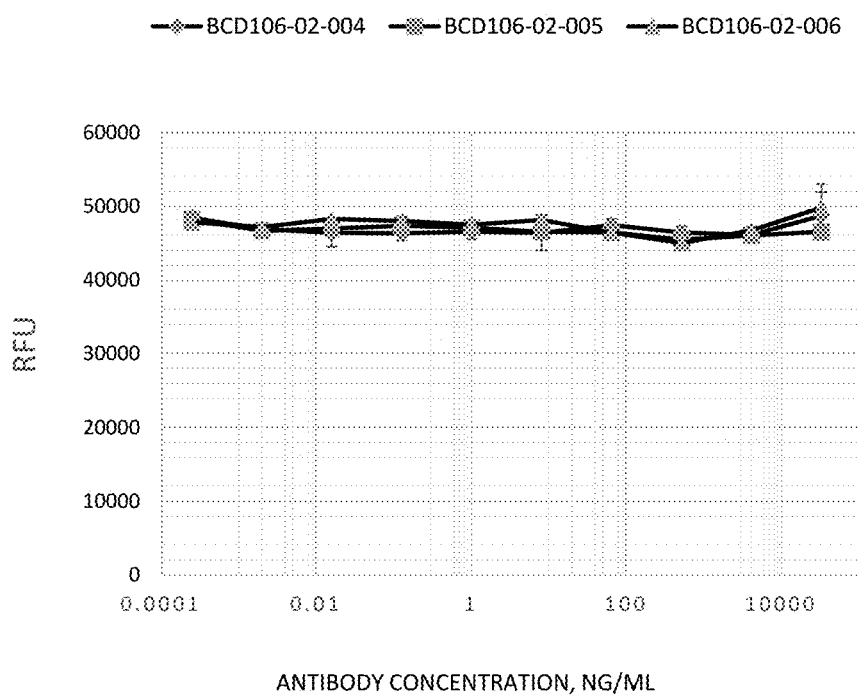
FIG. 14. Dependence of the level of fluorescence on the concentration of anti-PD-L1/anti-CD47 bispecific antibodies.
Figure 15:
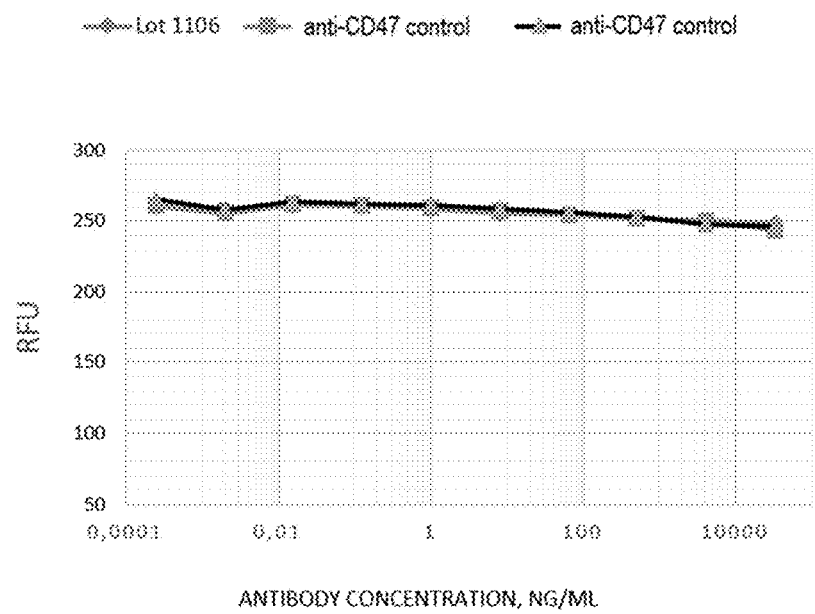
FIG. 15. Dependence of the level of fluorescence on the concentration of anti-PD-L1/anti-CD47 bispecific antibodies.
Figure 16:
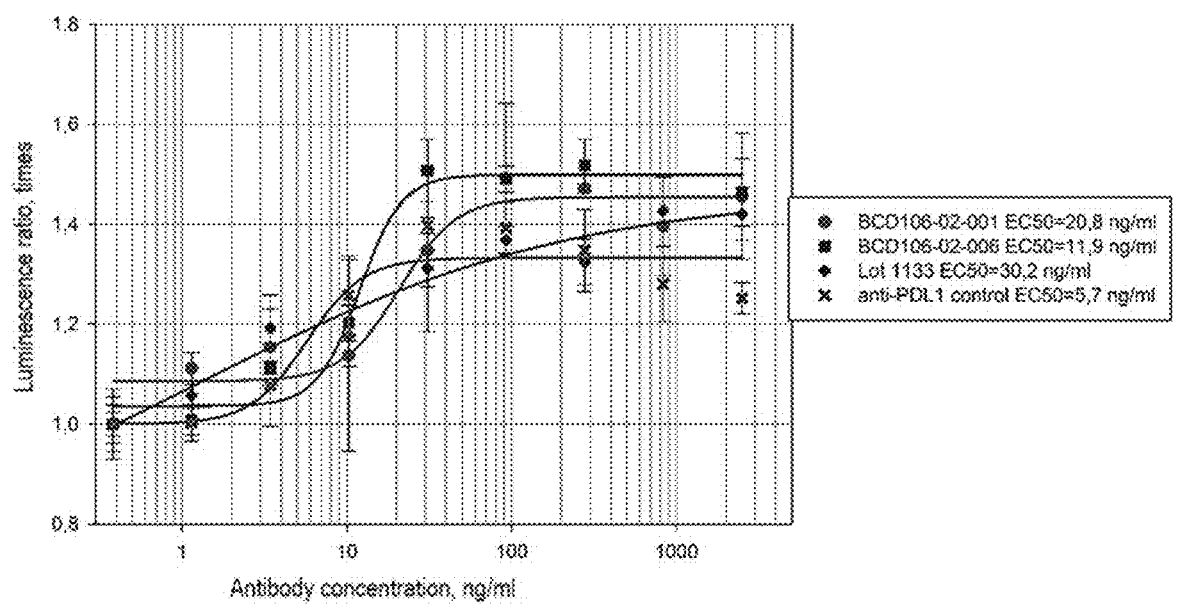
FIG. 16. Anti-PD-L1 activity of anti-PD-L1/CD47 bispecific antibodies. The vertical axis shows the luminescence ratio of the wells with the aHTH-CD47/PD-L1 antibodies tested against the luminescence of the wells without the addition of antibodies.

The results are shown in FIG. 11.

According to the data obtained, a number of anti-CD47/PD-L1 antibodies show efficacy in stimulating the phagocytosis of MDA-MB-231 cell lines by human macrophages, which is comparable to that of a control monospecific anti-CD47 antibody (clone B6H12).

Example 20

Comparison of Influence of Anti-PD-L1/Anti-CD47 Bispecific Antibody Candidates on Human Erythrocyte Hemagglutination Human erythrocytes were used to analyze the ability of antibodies to cause hemagglutination.

Preparation of Erythrocyte Suspension

Blood sample was taken from a healthy donor's vein into a vacuum heparin tube. 9 ml of blood was transferred into a 50 ml centrifuge tube. Blood was diluted to 30 ml with DPBS without Ca2+ and Mg2+ at room temperature. The suspension was centrifuged under 800 g for 10 minutes, the supernatant was decanted. The cell washing procedure was repeated twice with DPBS without Ca2+ and Mg2+ and centrifugation. 300 μl of cell pellet was then resuspended in 30 ml of DPBS, resulting in a 1% erythrocyte suspension.

Conducting Hemagglutination Assay

Test antibodies were diluted in DPBS to a concentration of 20 μg/ml. 100 μl of antibody dilutions and erythrocyte suspensions were mixed in a 96 well round-bottom plate. The plate was incubated in a CO2 incubator for 16 hours at 37° C. Results were documented visually using an arbitrary 4 cross scale. Significantly positive result is 2 crosses and above. The results are shown in table 10.

TABLE 10

Hemagglutination reaction in the presence of anti-CD47/PD-L1 antibodies.

| Antibody | Antibody concentration, ng/ml | | | | | | | | | | | |
|---|---|---|---|---|---|---|---|---|---|---|---|---|
| | 10000 | 5000 | 2500 | 1250 | 625 | 313 | 156 | 78 | 39 | 19.5 | 9.77 | 0 |
| anti-CD47/PD-L1 BCD106-02-001 | — | — | — | — | — | — | — | — | — | — | — | — |
| anti-CD47/PD-L1 BCD106-02-002 | — | — | — | — | — | — | — | — | — | — | — | — |
| anti-CD47/PD-L1 BCD106-02-003 | — | — | — | — | — | — | — | — | — | — | — | — |
| anti-CD47/PD-L1 BCD106-02-004 | — | — | — | — | — | — | — | — | — | — | — | — |
| anti-CD47/PD-L1 BCD106-02-005 | — | — | — | — | — | — | — | — | — | — | — | — |
| anti-CD47/PD-L1 BCD106-02-006 | — | — | — | — | — | — | — | — | — | — | — | — |
| anti-CD47/PD-L1 BCD106-1106 | — | — | — | — | — | — | — | — | — | — | — | — |
| anti-CD47/PD-L1 BCD106-1133 | — | — | — | — | — | — | — | — | — | — | — | — |
| anti-CD47 ctrl | 3+ | 3+ | 3+ | 3+ | 2+ | 1+ | — | — | — | — | — | — |
| anti-PD-L1 ctrl | — | — | — | — | — | — | — | — | — | — | — | — |

"—" indicates absence of agglutination.

According to the data obtained, none of the anti-CD47/PD-L1 antibodies cause hemagglutination, whereas the reference anti-CD47 monoclonal antibody (clone B6H12) cause significant agglutination due to the bivalent nature of the antibody, and, consequently, the ability to interact with two CD47 molecules located on different erythrocytes.

Example 21

Analysis of Complement-Dependent Cytotoxicity (CDC) of Bispecific Anti-CD47/PD-L1 Antibodies In order to perform CDC analysis (Complement-Dependent Cytotoxicity), MDA-MB-231 cell line containing PD-L1 and CD47 receptors on its surface was used as target cells.

Preparation of Target Cells

The MDA-MB-231 culture was cultured in DMEM culture medium supplemented with 10% fetal bovine serum (FBS).

Cells were removed from the plastic surface by trypsin and suspended in DMEM medium containing 0.1% BSA at a concentration of $1 \times 10^6$ cells/ml.

Preparation of Dilutions of Test Antibodies

All test anti-CD47/PD-L1 antibodies were diluted with DMEM medium containing 0.1% BSA to a concentration of 100 μg/ml. A series of serial dilutions with an increment of 8 was prepared. The concentrations of the test antibodies were (ng/ml): 100000; 12500; 1562.5; 195.3; 24.4; 3.05; 0.38; 0.04; 0.005.

Conducting CDC Test

Human complement was thawed and dissolved 1:4 in DMEM medium containing 0.1% BSA.

50 μl/well of each dilution of the test antibodies were added to the wells of a 96-well plate, 50 μl/well of medium supplemented with 0.1% BSA for each antibody specimen—cell control, 150 μl/well of DMEM medium containing 0.1% BSA-medium control.

50 μl/well of a suspension of MDA-MB-231 cells was added to each well containing the test antibodies and a cell control.

50 μl/well of the diluted complement was poured into all wells containing the test antibodies and a cell control. The plate was shaken for 2-4 minutes on an orbital shaker at room temperature, placed in a $CO_2$ incubator for 2-3 hours at 37° C.

15 μl of Alamar Blue reagent was added to the wells of the test plate. The plates were shaken for 10-20 minutes at room temperature on an orbital shaker. The plates were further incubated in a $CO_2$ incubator for 18-24 hours.

The plates were shaken for 10-20 minutes at room temperature on an orbital shaker.

Fluorescence was measured using relative fluorescence units at excitation/emission wavelength of 544/590 nm by using a plate fluorimeter. The fluorescence signal obtained is proportional to the number of viable cells. The results are shown in FIGS. 12-15.

According to the data obtained, the test antibodies do not cause complement-dependent cytotoxicity (CDC) of the MDA-MB-231 cell line.

Example 22

Analysis of Antagonistic Activity of Anti-PD-L1/Anti-CD47 Bispecific Antibodies Towards a Cell Culture Carrying PD-L1 Membrane Receptor In order to analyze the antagonistic activity of anti-PD-L1/CD47 antibodies against the PD-L1 receptor, the ability of said antibodies to reactivate a luciferase signal in Jurkat-PD1-NFAT-Luc reporter cell line during co-culture with PD-L1-producing cells was evaluated.

Preparation of PD-L1 Producing Cells

The MDA-MB-231 culture was cultured in DMEM culture medium supplemented with 10% fetal bovine serum (FBS).

Cells were removed from the plastic surface by trypsin and suspended at a concentration of $1*10^5$ cells/ml in DMEM medium containing 10% FBS and 20 ng/ml of interferon gamma 200 μl/well of the cell suspension was then added to the wells of a white 96-well plate and incubated for 48 hours in a $CO_2$ incubator at 37° C. and 5% $CO_2$.

Preparation of Dilutions of Test Antibodies

All the tested anti-CD47/PD-L1 antibodies were diluted with RPMI-1640 medium containing 10% FBS to a concentration of 5 μg/ml. A series of serial dilutions with an increment of 3 was prepared. The concentrations of the test antibodies were (ng/ml): 2500; 833.3; 277.7; 92.5; 30.8; 10.2; 3.4; 1.1.

Preparation of Jurkat-PD1-NFAT-Luc Cells

On the day of the experiment, a suspension of Jurkat-PD1-NFAT-Luc cells at a concentration of $2.5*10^6$ cells/ml in RPMI-1640 medium containing 10% FBS was prepared.

Preparation of a Solution of Activating Antibodies

On the day of the experiment, a 10-fold mixture of activating antibodies was prepared (4 μg/ml of anti-CD3; 4 μg/ml of anti-CD28; 16 μg/ml of anti-mouse in RPMI-1640 medium containing 10% FBS).

Conducting Test

Growth medium was removed from a plate containing MDA-MB-231 cells. 40 μl/well of antibody dilutions were added to the wells containing the cells. 40 μl/well of RPMI 1640 medium containing 10% FBS was added to control wells (cells without the test antibodies, cells without test and activating antibodies), and Incubated at room temperature for 30 minutes.

40 μl/well of Jurkat-PD1-NFAT-Luc cell suspension was then added to all wells. Then, 10 μl/well of a 10-fold solution of activating antibodies was added to all wells, except for the control wells "cells without test and activating antibodies". Cells were incubated for 6 hours in a $CO_2$ incubator at 37° C. and 5% $CO_2$.

The luciferase Substrate One-Glo Luciferase Assay System "Promega" was introduced into all wells at a ratio of 1:1 (90 μl/well). After 5-10 minutes, luminescence level was measured using a plate reader.

According to the data obtained, the test anti-PD-L1/anti-CD47 bispecific antibodies, as well as a control anti-PD-L1 monospecific antibody, are antagonists of the PD-L1-dependent signaling pathway, and, therefore, can stimulate T-cell dependent cytotoxicity towards cells carrying the PD-L1 receptor.

Figure 17:
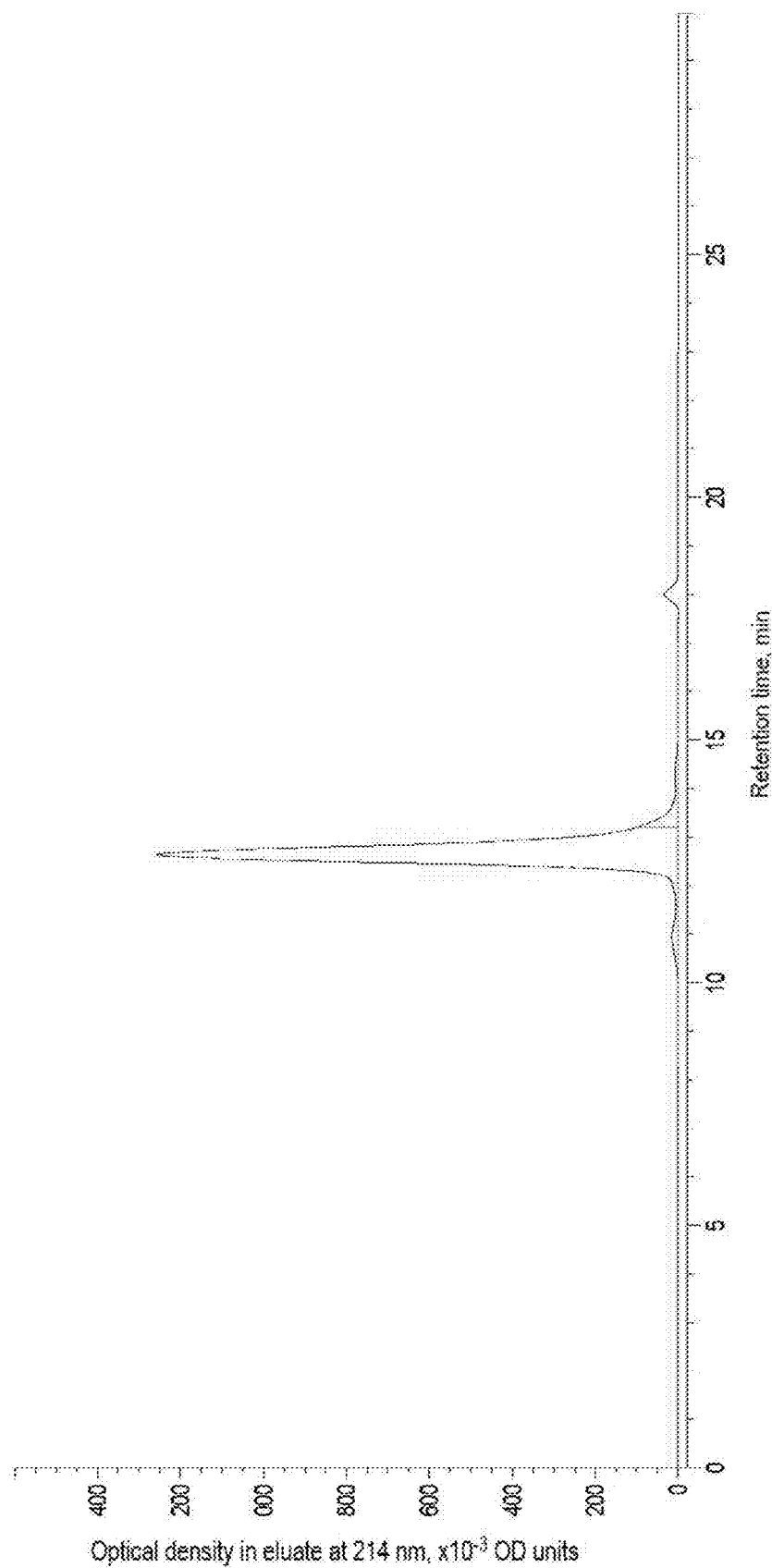
FIG. 17. Gel filtration profile for assessing the aggregation homogeneity of anti-PD-L1/anti-CD47 bispecific antibodies.

Example 25. Analysis of Homogeneity of Anti-PD-L1/anti-CD47 Bispecific Antibody Products Homogeneity of bispecific antibodies was analyzed by size-exclusion HPLC (SEC HPLC) with a UV detector. Chromatography was performed on a HPLC system (Agilent) on column Tosoh TSK-Gel G3000SWXL, 7.8 mm×30 cm, order no. 08541 with precolumn Tosoh TSKgel Guard SWXL, 6.0 mm×4.0 cm, with a particle diameter of 7 μm, order no. 08543. Detection was performed at wavelengths of 220 and 280 nm. FIG. 17 shows an examplary HPLC profile of product BCD106-02-013, based on VHH47Opt2 (see Example 12). According to the results of the test, one may conclude that molecule BCD106-02-013 generates a product that is 93% homogeneous in monomer's aggregation composition and is applicable for subsequent tests in vitro and in vivo.

What is claimed is:

1. A bispecific monoclonal antibody or its antigen-binding fragment, which specifically binds to CD47 and PD-L1, comprising a binding site to CD47, and at least one binding site to PD-L1, characterized in that the binding site to CD47 includes one of:

a) (i) a heavy chain variable domain that comprises CDR1, CDR2 and CDR3 sequences, wherein CDR1 comprises SEQ ID NO: 1, wherein CDR2 comprises SEQ ID NO: 6 or 7, wherein CDR3 comprises SEQ ID NO: 17, and (ii) a light chain variable domain comprising the sequences CDR1, CDR2, CDR3, wherein:
CDR1 comprises SEQ ID NO: 22, CDR2 comprises SEQ ID NO: 36, and CDR3 comprises SEQ. ID NO: 50;

CDR1 comprises SEQ ID NO: 25, CDR2 comprises SEQ ID NO: 38, and CDR3 comprises SEQ. ID NO: 53;
CDR1 comprises SEQ ID NO: 29, CDR2 comprises SEQ ID NO: 48, and CDR3 comprises SEQ. ID NO: 64;
CDR1 comprises SEQ ID NO: 28, CDR2 comprises SEQ ID NO: 40, and CDR3 comprises SEQ. ID NO: 56;
CDR1 comprises SEQ ID NO: 23, CDR2 comprises SEQ ID NO: 37, and CDR3 comprises SEQ. ID NO: 51;
CDR1 comprises SEQ ID NO: 30, CDR2 comprises SEQ ID NO: 42, and CDR3 comprises SEQ. ID NO: 58;
CDR1 comprises SEQ ID NO: 24, CDR2 comprises SEQ ID NO: 43, and CDR3 comprises SEQ. ID NO: 59; or
CDR1 comprises SEQ ID NO: 32, CDR2 comprises SEQ ID NO: 45, and CDR3 comprises SEQ. ID NO: 61;
b) (i) a heavy chain variable domain comprising the sequences CDR1, CDR2, CDR3, where CDR1 comprises SEQ. ID NO: 1, where CDR2 comprises SEQ. ID NO: 8, SEQ. ID NO: 9, SEQ. ID NO: 11, or SEQ. ID NO: 12, where CDR3 comprises SEQ. ID NO: 17; and
(ii) a light chain variable domain comprising the sequences CDR1, CDR2, CDR3, where CDR1 comprises SEQ ID NO: 32, CDR2 comprises SEQ ID NO: 45, and CDR3 comprises SEQ. ID NO: 61; and
c) wherein the binding site to CD47 is an anti-CD47 VHH variable domain, comprising a heavy chain variable domain comprising CDR1, CDR2 and CDR3, wherein CDR1 comprises SEQ. ID NO: 2 or SEQ ID NO: 4, CDR2 comprises SEQ. ID NO: 10 or SEQ. ID NO: 15, and CDR3 comprises SEQ. ID NO: 18 or SEQ ID NO: 20; and the binding site to PD-L1 comprises:
a heavy chain variable domain that comprises CDR1, CDR2, CDR3 sequences, wherein CDR1 comprises SEQ ID NO: 5, wherein CDR2 comprises SEQ ID NO: 16 and wherein CDR3 comprises SEQ ID NO: 21; and
a light chain variable domain that comprises CDR1, CDR2, CDR3 sequences, wherein CDR1 comprises SEQ ID NO: 35, wherein CDR2 comprises SEQ ID NO: 49 and wherein CDR3 comprises SEQ ID NO: 65.

2. The antibody according to claim 1, characterized in that the binding site to CD47 includes the heavy chain variable domain that comprises sequences that are at least 90% homologous to a sequence selected from the group of SEQ ID NO: 66-80, and a light chain variable domain that comprises sequences that are at least 90% homologous to the sequences selected from the group of SEQ ID NOs: 89-106.

3. The antibody according to claim 1, characterized in that the binding site to CD47 includes the heavy chain variable domain that comprises a sequence selected from the group of SEQ ID NOs: 66-80, and a light chain variable domain that comprises the sequences selected from the group of SEQ ID NOs: 89-106.

4. The antibody according to claim 1, characterized in that:
(i) the binding site to CD47 is a Fab, scFv, scFab, or VHH mono-domains; or
(ii) the binding site to PD-L1 is a Fab, scFv, or scFab.

5. The antibody according to claim 1, characterized in that the antibody causes antibody-dependent cellular cytotoxicity, macrophage-mediated phagocytosis, and/or T cell-mediated cytotoxicity of the ratio of cells bearing CD47 and/or PD-L1 antigens on the surface.

6. The antibody according to claim 1, characterized in that the antibody comprises an Fc fragment comprising at least one mutation or modification that increases antibody-dependent cell-mediated cytotoxicity (ADCC) and/or complement-dependent cytotoxicity (CDC) compared to the same antibody without the mutation or the modification.

7. A nucleic acid that encodes the antibody according to claim 1.

8. The nucleic acid according to claim 7, wherein the nucleic acid is DNA.

9. An expression vector comprising the nucleic acid according to claim 7.

10. A method of obtaining a host cell to produce a monoclonal antibody which specifically binds to CD47 and PD-L1, including the transformation of the cell with the expression vector according to claim 9.

11. A host cell for obtaining a monoclonal antibody which specifically binds to CD47 and PD-L1, comprising the nucleic acid according to claim 7.

12. A method of obtaining a monoclonal antibody which specifically binds to CD47 and PD-L1, comprising the cultivation of the host cell according to claim 11 in culture medium under conditions sufficient to obtain the specified antibody followed by isolation and purification of the obtained antibody.

13. A pharmaceutical composition comprising the antibody according to claim 1, in combination with one or several pharmaceutically acceptable excipients.

* * * * *